US010105427B2

(12) United States Patent
Lauer et al.

(10) Patent No.: US 10,105,427 B2
(45) Date of Patent: Oct. 23, 2018

(54) EPIDERMAL GROWTH FACTOR RECEPTOR VARIANT III-MESOTHELIN FUSIONS AND METHODS OF USING THE SAME

(71) Applicant: Aduro Biotech, Inc., Berkeley, CA (US)

(72) Inventors: Peter M. Lauer, Albany, CA (US); William G. Hanson, Walnut Creek, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 0 days.

(21) Appl. No.: 15/097,178

(22) Filed: Apr. 12, 2016

(65) Prior Publication Data

US 2016/0346369 A1 Dec. 1, 2016

Related U.S. Application Data

(60) Provisional application No. 62/243,397, filed on Oct. 19, 2015, provisional application No. 62/146,559, filed on Apr. 13, 2015.

(51) Int. Cl.

| | |
|---|---|
| ***A61K 38/00*** | (2006.01) |
| ***A61K 39/00*** | (2006.01) |
| ***C07K 14/735*** | (2006.01) |
| ***C12N 15/62*** | (2006.01) |

(52) U.S. Cl.

CPC .... *A61K 39/0011* (2013.01); *C07K 14/70535* (2013.01); *C12N 15/62* (2013.01); *A61K 38/00* (2013.01); *A61K 2039/523* (2013.01)

(58) Field of Classification Search

CPC ............................ A61K 38/00; A61K 39/0011

See application file for complete search history.

(56) References Cited

U.S. PATENT DOCUMENTS

| | | | |
|---|---|---|---|
| 5,830,702 | A | 11/1998 | Portnoy et al. |
| 6,051,237 | A | 4/2000 | Paterson |
| 6,224,868 | B1 | 5/2001 | Wong et al. |
| 6,565,852 | B1 | 5/2003 | Paterson |
| 7,588,930 | B2 | 9/2009 | Paterson et al. |
| 9,200,057 | B2 * | 12/2015 | Lauer ................ A61K 39/0011 |
| 9,663,557 | B2 * | 5/2017 | Lauer .................. C07K 14/195 |
| 9,808,516 | B2 | 11/2017 | Brockstedt et al. |
| 2004/0197343 | A1 | 10/2004 | Dubensky et al. |
| 2004/0228877 | A1 | 11/2004 | Dubensky et al. |
| 2005/0037010 | A1 | 2/2005 | Monahan et al. |
| 2007/0207170 | A1 | 9/2007 | Dubensky et al. |
| 2008/0286781 | A1 | 11/2008 | Monahan et al. |
| 2011/0245480 | A1 | 10/2011 | Dubensky, Jr. et al. |
| 2012/0264625 | A1 | 10/2012 | Monahan et al. |
| 2014/0037662 | A1 | 2/2014 | Lauer et al. |
| 2014/0186387 | A1 | 7/2014 | Lauer et al. |
| 2014/0315314 | A1 | 10/2014 | Dubensky, Jr. et al. |
| 2014/0356366 | A1 | 12/2014 | Cheong et al. |
| 2016/0074491 | A1 | 3/2016 | Lauer et al. |
| 2016/0324945 | A1 | 11/2016 | Brockstedt et al. |
| 2018/0085446 | A1 | 3/2018 | Brockstedt et al. |

FOREIGN PATENT DOCUMENTS

| | | | |
|---|---|---|---|
| EP | 2808035 | A1 | 12/2014 |
| WO | WO 2004/006837 | | 1/2004 |
| WO | WO 2004/018999 | A2 | 3/2004 |
| WO | WO 2004/112825 | | 12/2004 |
| WO | WO 2007/103225 | A2 | 9/2007 |
| WO | WO2007103225 | A2 * | 9/2007 |
| WO | WO 2007/117371 | | 10/2007 |
| WO | WO 2012/068360 | A1 | 5/2012 |
| WO | WO 2014/106123 | A1 | 7/2014 |
| WO | WO 2016/168198 | A1 | 10/2016 |
| WO | WO 2016/168214 | A2 | 10/2016 |

OTHER PUBLICATIONS

Le et al. (Clin. Cancer Res. Feb. 1, 2012; 18 (3): 858-68).*

Arlen et al.; "Strategies for the development of PSA-based vaccines for the treatment of advanced prostate cancer," *Expert Rev Vaccines*, 2(4):483-493 (2003).

Le et al.; "Next-Generation Cancer Vaccine Approaches: Integrating Lessons Learned From Current Successes With Promising Biotechnologic Advances," Journal of the National Comprehensive Cancer Network : *JNCCN*. 11 (7): 766-772 (2013).

Shahabi et al.; "Development of a Listeria monocytogenes based vaccine against prostate cancer," *Cancer Immunol Immunother*., 57(9):1301-1313 (2008).

Wesikirch et al.; "Listeria monocytogenes: a potent vaccine vector for neoplastic and infectious disease," *Immunol Rev.*,158:159-169 (1997).

Brockstedt, et al., "Listeria-based cancer vaccines that segregate immunogenicity from toxicity," *PNAS*, Sep. 21, 2004, vol. 101, No. 38, pp. 13832-13837 and slides.

Camilli, et al.,"Dual roles of plcA in *Listeria monocytogenes* pathogenesis," *Molecular Microbiology*, Apr. 1993: 8(1), pp. 143-157.

Eisenhauer, et al., "New response evaluation criteria in solid tumours: Revised RECIST guideline (version 1.1)," *European Journal of Cancer*, 45(2009), pp. 228-247.

(Continued)

*Primary Examiner* — Stephen L Rawlings

(74) *Attorney, Agent, or Firm* — Hamilton, Brook, Smith & Reynolds, P.C.

(57) ABSTRACT

Provided herein are compositions and methods for eliciting an immune response in a subject. In particular, the present disclosure is directed to fusion proteins comprising an epidermal growth factor receptor variant III (EGFRvIII) polypeptide and a mesothelin polypeptide, and methods of eliciting an immune response using host cells comprising nucleic acid molecules encoding said fusion proteins. In some embodiments, the nucleic acid molecules can encode an EGFRvIII-mesothelin fusion protein comprising an amino acid sequence that is at least i) 90% identical, ii) 95% identical, or iii) 99% identical to EGFRvIIIx5-mesothelin$_{35-622}$ as set forth in SEQ ID NO:8.

20 Claims, 5 Drawing Sheets

Specification includes a Sequence Listing.

(56) References Cited

OTHER PUBLICATIONS

Lauer, et al., "Constitutive Activation of the PrfA Regulon Enhances the Potency of Vaccines Based on Live-Attenuated and Killed but Metabolically Active *Listeria monocytogenes* Strains," *Infection and Immunity*, Aug. 2008, p. 3742-3753.
Lauer, et al., "Construction, Characterization, and Use of Two *Listeria monocytogenes* Site-Specific Phage Integration Vectors," *Journal of Bacteriology*, Aug. 2002, pp. 4177-4186.
Notification of Transmittal of the International Search Report and the Written Opinion of the International Searching Authority, or the Declaration for International Application No. PCT/US2016/027136, dated Jun. 28, 2016.
Sinnathamby, et al., "Priming and Activation of Human Ovarian and Breast Cancer-specific CD8+ T Cells by Polyvalent *Listeria monocytogenes*-based Vaccines," *Journal of Immunotherapy*, Oct. 2009, vol. 32, Issue 8, pp. 856-869.
Toes, et al., "Discrete Cleavage Motifs of Constitutive and Immunoproteasomes Revealed by Quantitative Analysis of Cleavage Products," *J.Exp. Med.*, vol. 194, No. 1, Jul. 2, 2001, pp. 1-12.
Wolchok, et al., "Guidelines for the Evaluation of Immune Therapy Activity in Solid Tumors: Immune-Related Response Criteria," *Clin. Cancer Res*. 2009; 15(23) Dec. 1, 2009, pp. 7412-7420.
Ayyoub, M., et al., "SSX Antigens as Tumor Vaccine Targets in Human Sarcoma," *Cancer Immunity*, vol. 3: 13 (2003).
Cecco, S., et al., "Cancer Vaccines in Phase II/III Clinical Trials: State of the Art and Future Perspectives," *Current Cancer Drug Targets*, vol. 11: 85-102 (2011).
Fujio, K., et al., "A Vaccine Strategy with Multiple Prostatic Acid Phosphatase-fused Cytokines for Prostate Cancer Treatment," *Oncology Reports*, vol. 33: 1585-1592 (2015).
Gurel, B., et al., "NKX3.1 as a Marker of Prostatic Origin in Metastatic Tumors," *Am J Surg Pathol*, 34(8):1097-1105 (2010).
Invitation to Pay Additional Fees for International Application No. PCT/US2016/027167, entitled: "Immunogenic Fusion Proteins for the Treatment of Cancer," dated Aug. 10, 2016.
Notice of Allowance for U.S. Appl. No. 15/097,271, entitled: "Immunogenic Fusion Proteins for the Treatment of Cancer," dated Nov. 16, 2016.
Notification of Transmittal of the International Search Report and the Written Opinion of the International Searching Authority, or the Declaration for International Application No. PCT/US2016/027167, entitled: "Immunogenic Fusion Proteins for the Treatment of Cancer," dated Oct. 20, 2016.
Smith, H.A. and McNeel, D. G., "The SSX Family of Cancer-Testis Antigens as Target Proteins for Tumor Therapy", *Clinical and Developmental Immunology*, vol. 2010: 18 pages (2010).
U.S. Appl. No. 15/097,271, filed Apr. 12, 2016; Notice of Allowance dated Jun. 30, 2017.
Examination Report for Australian Appl. No. 2016247894, titled "Immunogenic Fusion Proteins for the Treatment of Cancer," consisting of 4 pages, dated Apr. 13, 2018.

* cited by examiner

| Ln | Strain | Antigen cassette | ActA |
|---|---|---|---|
| 1 | Lm11 | none | - |
| 2 | CRS-207 | $Mesothelin_{35-622}$ | 1.45 |
| 3 | ADU-214 | EGFRvIIIx5-$Mesothelin_{35-622}$ | 74.98 |

SEQUENCE LISTING

```
<160> NUMBER OF SEQ ID NOS: 32

<210> SEQ ID NO 1
<211> LENGTH: 2744
<212> TYPE: DNA
<213> ORGANISM: Artificial Sequence
<220> FEATURE:
<223> OTHER INFORMATION: actAp-ActAN100*-EGFRvIIIx5-mesothelin35-622
```

nucleotide sequence

<400> SEQUENCE: 1

```
gggaagcagt tggggttaac tgattaacaa atgttagaga aaaattaatt ctccaagtga     60
tattcttaaa ataattcatg aatatttttt cttatattag ctaattaaga agataattaa    120
ctgctaatcc aatttttaac ggaataaatt agtgaaaatg aaggccgaat tttccttgtt    180
ctaaaaaggt tgtattagcg tatcacgagg agggagtata agtgggatta aatagattta    240
tgcgtgcgat gatggtagtt ttcattactg ccaactgcat tacgattaac cccgacataa    300
tatttgcagc gacagatagc gaagattcca gtctaaacac agatgaatgg gaagaagaat    360
acgaaactgc acgtgaagta agttcacgtg atattgagga actagaaaaa tcgaataaag    420
tgaaaaatac gaacaaagca gaccaagata ataaacgtaa agcaaaagca gagaaaggtg    480
gatccgcaag caaagtattg ccagctagtc gtgcattaga ggagaaaaag gggaattacg    540
tggtgacgga tcatggatcg tgtgccgatg gctcagtaaa gactagtgcg agcaaagtgg    600
cccctgcatc acgagcactt gaagagaaaa aaggaaacta tgttgtgacc gatcatggta    660
gctgcggaga tggttcaatt aaattatcaa aagtcttacc agcatctaga gctttagagg    720
aaaagaaggg taactatgtc gtaacagatc atggaagttg tgctgacgga agtgttaaag    780
cgtcgaaagt agctccagct tctcgcgcat tagaagaaaa gaaaggcaat tatgttgtaa    840
cagaccatgg tagttgtggt gatggctcga tcaaattgtc aaaagttcta ccggcttctc    900
gtgcgctaga agagaagaaa ggaaattacg tagttacaga ccacggctct tgcgcggatg    960
gttccgttaa acaattgcgt acattagcag gtgaaacagg tcaagaagca gcaccacttg   1020
acggtgtatt aacgaatcca ccaaatatat caagtttaag tccacgtcaa ttattaggtt   1080
ttccatgtgc agaagtttca ggtttaagta cagaacgtgt ccgtgagtta gcagttgcat   1140
tagcacaaaa aaacgttaaa ttatctacag aacagttacg ttgtttagcc catagattaa   1200
gcgaaccacc agaagactta gatgcacttc ctttagacct tcttttattc ttaaatccag   1260
atgcattttc aggaccacaa gcatgtacac gtttttttag tcgaattaca aaagccaatg   1320
ttgatttatt acctcgtggg gctcctgaaa gacaacgttt attacctgct gcattagcat   1380
gctggggtgt tcgcggtagc ttattaagtg aagccgatgt tcgtgcttta gggggtttag   1440
catgtgattt acctggtcgt ttcgttgcag aatcagcaga agtgttatta ccgagattag   1500
tttcatgccc aggaccttta gatcaagatc aacaagaggc agctagagca gctcttcaag   1560
gaggaggccc accatatggc ccaccaagta catggagtgt ttctacaatg gatgcgttaa   1620
gaggtttatt accggtttta ggacaaccaa ttattcgtag tattccacaa ggcattgtag   1680
cagcatggcg tcaacgtagt tctcgtgatc cgtcttggcg acaaccagaa cgtacaattc   1740
tacgtccaag atttcgtaga gaagtagaaa aaacggcgtg tcctagtggc aaaaaagcac   1800
gtgaaattga tgaaagttta atttttata aaaaatggga attagaagca tgtgtcgatg   1860
cagcattact agctacacaa atggatcgtg ttaatgctat tccattcaca tatgaacaat   1920
tagatgtttt aaagcataaa ttagacgaat tatatccaca aggttatcca gaatcagtta   1980
ttcaacattt aggttactta tttttaaaaa tgagtccaga agacatacgc aaatggaatg   2040
ttacaagttt agaaacatta aaagcgcttt tagaagttaa caaaggtcat gaaatgagtc   2100
cacaagttgc tacgttaatt gatagattcg ttaaaggccg tggtcaatta gataaagata   2160
ctttagatac attaacagca ttttatcctg gctacttatg cagtttatca ccagaagaat   2220
taagttccgt tccaccgagt agtatctggg cagttcgtcc gcaagattta gatacatgcg   2280
```

acccacgtca attagatgtt ttatatccaa aagcaagatt agctttccaa aatatgaacg 2340
gtagtgaata tttcgtaaaa attcaatcct ttttaggtgg tgcaccaact gaagatctaa 2400
aagcattaag ccaacaaaat gtaagtatgg atttagctac gtttatgaaa ttacgtacag 2460
atgcagttct accattaaca gttgcagaag ttcaaaaatt attaggtcca cacgtagaag 2520
gattaaaagc agaagaacgt caccgtccag ttcgcgattg gattttacgt caacgtcaag 2580
atgatttaga tacattaggt ttaggtttac aaggcggtat tccgaatgga tatttagtgt 2640
tagatttatc ggttcaagaa gcattaagtg gtacaccgtg tttattaggt ccaggtccag 2700
ttttaacagt gttagcatta ttattagcca gtacattagc ttaa 2744

<210> SEQ ID NO 2
<211> LENGTH: 221
<212> TYPE: DNA
<213> ORGANISM: Artificial Sequence
<220> FEATURE:
<223> OTHER INFORMATION: actA promoter nucleotide sequence

<400> SEQUENCE: 2
gggaagcagt tggggttaac tgattaacaa atgttagaga aaaattaatt ctccaagtga 60
tattcttaaa ataattcatg aatatttttt cttatattag ctaattaaga agataattaa 120
ctgctaatcc aatttttaac ggaataaatt agtgaaaatg aaggccgaat tttccttgtt 180
ctaaaaaggt tgtattagcg tatcacgagg agggagtata a 221

<210> SEQ ID NO 3
<211> LENGTH: 258
<212> TYPE: DNA
<213> ORGANISM: Artificial Sequence
<220> FEATURE:
<223> OTHER INFORMATION: ActAN100* nucleotide sequence sequence

<400> SEQUENCE: 3
gtgggattaa atagatttat gcgtgcgatg atggtagttt tcattactgc caactgcatt 60
acgattaacc ccgacataat atttgcagcg acagatagcg aagattccag tctaaacaca 120
gatgaatggg aagaagaata cgaaactgca cgtgaagtaa gttcacgtga tattgaggaa 180
ctagaaaaat cgaataaagt gaaaaatacg aacaaagcag accaagataa taaacgtaaa 240
gcaaaagcag agaaaggt 258

<210> SEQ ID NO 4
<211> LENGTH: 63
<212> TYPE: DNA
<213> ORGANISM: Artificial Sequence
<220> FEATURE:
<223> OTHER INFORMATION: EGFRvIII nucleotide sequence sequence
<220> FEATURE:
<221> NAME/KEY: misc_feature
<222> LOCATION: 33,42
<223> OTHER INFORMATION: n = A, T, C or G

<400> SEQUENCE: 4
ccdgcwwswm ghgcdytwga rgaraaraar ggnaaytayg tngtdacvga ycaygghwsb 60 tgy 63

<210> SEQ ID NO 5
<211> LENGTH: 486
<212> TYPE: DNA
<213> ORGANISM: Artificial Sequence
<220> FEATURE:

```
<223> OTHER INFORMATION: EGFRvIIIx5 nucleotide sequence

<400> SEQUENCE: 5

gcaagcaaag tattgccagc tagtcgtgca ttagaggaga aaaaggggaa ttacgtggtg     60

acggatcatg gatcgtgtgc cgatggctca gtaaagacta gtgcgagcaa agtggcccct    120

gcatcacgag cacttgaaga gaaaaaagga aactatgttg tgaccgatca tggtagctgc    180

ggagatggtt caattaaatt atcaaaagtc ttaccagcat ctagagcttt agaggaaaag    240

aagggtaact atgtcgtaac agatcatgga agttgtgctg acggaagtgt taaagcgtcg    300

aaagtagctc cagcttctcg cgcattagaa gaaaagaaag gcaattatgt tgtaacagac    360

catggtagtt gtggtgatgg ctcgatcaaa ttgtcaaaag ttctaccggc ttctcgtgcg    420

ctagaagaga agaaaggaaa ttacgtagtt acagaccacg gctcttgcgc ggatggttcc    480

gttaaa                                                               486


<210> SEQ ID NO 6
<211> LENGTH: 1764
<212> TYPE: DNA
<213> ORGANISM: Artificial Sequence
<220> FEATURE:
<223> OTHER INFORMATION: Mesothelin35-622 nucleotide sequence

<400> SEQUENCE: 6

cgtacattag caggtgaaac aggtcaagaa gcagcaccac ttgacggtgt attaacgaat     60

ccaccaaata tatcaagttt aagtccacgt caattattag gttttccatg tgcagaagtt    120

tcaggtttaa gtacagaacg tgtccgtgag ttagcagttg cattagcaca aaaaaacgtt    180

aaattatcta cagaacagtt acgttgttta gcccatagat taagcgaacc accagaagac    240

ttagatgcac ttcctttaga ccttctttta ttcttaaatc cagatgcatt ttcaggacca    300

caagcatgta cacgtttttt tagtcgaatt acaaaagcca atgttgattt attacctcgt    360

ggggctcctg aaagacaacg tttattacct gctgcattag catgctgggg tgttcgcggt    420

agcttattaa gtgaagccga tgttcgtgct ttaggggggtt tagcatgtga tttacctggt    480

cgtttcgttg cagaatcagc agaagtgtta ttaccgagat tagtttcatg cccaggacct    540

ttagatcaag atcaacaaga ggcagctaga gcagctcttc aaggaggagg cccaccatat    600

ggcccaccaa gtacatggag tgtttctaca atggatgcgt taagaggttt attaccggtt    660

ttaggacaac caattattcg tagtattcca caaggcattg tagcagcatg gcgtcaacgt    720

agttctcgtg atccgtcttg gcgacaacca gaacgtacaa ttctacgtcc aagatttcgt    780

agagaagtag aaaaaacggc gtgtcctagt ggcaaaaaag cacgtgaaat tgatgaaagt    840

ttaatttttt ataaaaaatg ggaattagaa gcatgtgtcg atgcagcatt actagctaca    900

caaatggatc gtgttaatgc tattccattc acatatgaac aattagatgt tttaaagcat    960

aaattagacg aattatatcc acaaggttat ccagaatcag ttattcaaca tttaggttac   1020

ttatttttaa aaatgagtcc agaagacata cgcaaatgga atgttacaag tttagaaaca   1080

ttaaaagcgc ttttagaagt taacaaaggt catgaaatga gtccacaagt tgctacgtta   1140

attgatagat tcgttaaagg ccgtggtcaa ttagataaag atactttaga tacattaaca   1200

gcattttatc ctggctactt atgcagttta tcaccagaag aattaagttc cgttccaccg   1260

agtagtatct gggcagttcg tccgcaagat ttagatacat gcgacccacg tcaattagat   1320

gttttatatc caaaagcaag attagctttc caaaatatga acggtagtga atatttcgta   1380

aaaattcaat cctttttagg tggtgcacca actgaagatc taaaagcatt aagccaacaa   1440
```

```
aatgtaagta tggatttagc tacgtttatg aaattacgta cagatgcagt tctaccatta   1500

acagttgcag aagttcaaaa attattaggt ccacacgtag aaggattaaa agcagaagaa   1560

cgtcaccgtc cagttcgcga ttggatttta cgtcaacgtc aagatgattt agatacatta   1620

ggtttaggtt tacaaggcgg tattccgaat ggatatttag tgttagattt atcggttcaa   1680

gaagcattaa gtggtacacc gtgtttatta ggtccaggtc cagttttaac agtgttagca   1740

ttattattag ccagtacatt agct                                          1764
```

```
<210> SEQ ID NO 7
<211> LENGTH: 2256
<212> TYPE: DNA
<213> ORGANISM: Artificial Sequence
<220> FEATURE:
<223> OTHER INFORMATION: EGFRvIIIx5-Mesothelin35-622 nucleotide sequence
      sequence

<400> SEQUENCE: 7

gcaagcaaag tattgccagc tagtcgtgca ttagaggaga aaaaggggaa ttacgtggtg     60

acggatcatg gatcgtgtgc cgatggctca gtaaagacta gtgcgagcaa agtggcccct    120

gcatcacgag cacttgaaga gaaaaaagga aactatgttg tgaccgatca tggtagctgc    180

ggagatggtt caattaaatt atcaaaagtc ttaccagcat ctagagcttt agaggaaaag    240

aagggtaact atgtcgtaac agatcatgga agttgtgctg acggaagtgt taaagcgtcg    300

aaagtagctc cagcttctcg cgcattagaa gaaaagaaag gcaattatgt tgtaacagac    360

catggtagtt gtggtgatgg ctcgatcaaa ttgtcaaaag ttctaccggc ttctcgtgcg    420

ctagaagaga agaaaggaaa ttacgtagtt acagaccacg gctcttgcgc ggatggttcc    480

gttaaacaat tgcgtacatt agcaggtgaa acaggtcaag aagcagcacc acttgacggt    540

gtattaacga atccaccaaa tatatcaagt ttaagtccac gtcaattatt aggttttcca    600

tgtgcagaag tttcaggttt aagtacagaa cgtgtccgtg agttagcagt tgcattagca    660

caaaaaaacg ttaaattatc tacagaacag ttacgttgtt tagcccatag attaagcgaa    720

ccaccagaag acttagatgc acttccttta gaccttcttt tattcttaaa tccagatgca    780

ttttcaggac cacaagcatg tacacgtttt tttagtcgaa ttacaaaagc caatgttgat    840

ttattacctc gtggggctcc tgaaagacaa cgtttattac ctgctgcatt agcatgctgg    900

ggtgttcgcg gtagcttatt aagtgaagcc gatgttcgtg ctttaggggg tttagcatgt    960

gatttacctg gtcgtttcgt tgcagaatca gcagaagtgt tattaccgag attagtttca   1020

tgcccaggac ctttagatca agatcaacaa gaggcagcta gagcagctct tcaaggagga   1080

ggcccaccat atggcccacc aagtacatgg agtgtttcta caatggatgc gttaagaggt   1140

ttattaccgg ttttaggaca accaattatt cgtagtattc cacaaggcat tgtagcagca   1200

tggcgtcaac gtagttctcg tgatccgtct tggcgacaac cagaacgtac aattctacgt   1260

ccaagatttc gtagagaagt agaaaaaacg gcgtgtccta gtggcaaaaa agcacgtgaa   1320

attgatgaaa gtttaatttt ttataaaaaa tgggaattag aagcatgtgt cgatgcagca   1380

ttactagcta cacaaatgga tcgtgttaat gctattccat tcacatatga acaattagat   1440

gttttaaagc ataaattaga cgaattatat ccacaaggtt atccagaatc agttattcaa   1500

catttaggtt acttattttt aaaaatgagt ccagaagaca tacgcaaatg gaatgttaca   1560

agtttagaaa cattaaaagc gcttttagaa gttaacaaag gtcatgaaat gagtccacaa   1620

gttgctacgt taattgatag attcgttaaa ggccgtggtc aattagataa agatacttta   1680
```

```
gatacattaa cagcatttta tcctggctac ttatgcagtt tatcaccaga agaattaagt   1740

tccgttccac cgagtagtat ctgggcagtt cgtccgcaag atttagatac atgcgaccca   1800

cgtcaattag atgttttata tccaaaagca agattagctt tccaaaatat gaacggtagt   1860

gaatatttcg taaaaattca atccttttta ggtggtgcac caactgaaga tctaaaagca   1920

ttaagccaac aaaatgtaag tatggattta gctacgttta tgaaattacg tacagatgca   1980

gttctaccat taacagttgc agaagttcaa aaattattag gtccacacgt agaaggatta   2040

aaagcagaag aacgtcaccg tccagttcgc gattggattt tacgtcaacg tcaagatgat   2100

ttagatacat taggtttagg tttacaaggc ggtattccga atggatattt agtgttagat   2160

ttatcggttc aagaagcatt aagtggtaca ccgtgtttat taggtccagg tccagtttta   2220

acagtgttag cattattatt agccagtaca ttagct                             2256
```

<210> SEQ ID NO 8
<211> LENGTH: 840
<212> TYPE: PRT
<213> ORGANISM: Artificial Sequence
<220> FEATURE:
<223> OTHER INFORMATION: ADU-214 fusion protein amino acid sequence

<400> SEQUENCE: 8

```
Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Ala Ser Lys Val Leu Pro Ala Ser
                85                  90                  95

Arg Ala Leu Glu Glu Lys Lys Gly Asn Tyr Val Val Thr Asp His Gly
            100                 105                 110

Ser Cys Ala Asp Gly Ser Val Lys Thr Ser Ala Ser Lys Val Ala Pro
        115                 120                 125

Ala Ser Arg Ala Leu Glu Glu Lys Lys Gly Asn Tyr Val Val Thr Asp
    130                 135                 140

His Gly Ser Cys Gly Asp Gly Ser Ile Lys Leu Ser Lys Val Leu Pro
145                 150                 155                 160

Ala Ser Arg Ala Leu Glu Glu Lys Lys Gly Asn Tyr Val Val Thr Asp
                165                 170                 175

His Gly Ser Cys Ala Asp Gly Ser Val Lys Ala Ser Lys Val Ala Pro
            180                 185                 190

Ala Ser Arg Ala Leu Glu Glu Lys Lys Gly Asn Tyr Val Val Thr Asp
        195                 200                 205

His Gly Ser Cys Gly Asp Gly Ser Ile Lys Leu Ser Lys Val Leu Pro
    210                 215                 220

Ala Ser Arg Ala Leu Glu Glu Lys Lys Gly Asn Tyr Val Val Thr Asp
225                 230                 235                 240

His Gly Ser Cys Ala Asp Gly Ser Val Lys Gln Leu Arg Thr Leu Ala
                245                 250                 255
```

```
Gly Glu Thr Gly Gln Glu Ala Ala Pro Leu Asp Gly Val Leu Thr Asn
            260                 265                 270

Pro Pro Asn Ile Ser Ser Leu Ser Pro Arg Gln Leu Leu Gly Phe Pro
        275                 280                 285

Cys Ala Glu Val Ser Gly Leu Ser Thr Glu Arg Val Arg Glu Leu Ala
    290                 295                 300

Val Ala Leu Ala Gln Lys Asn Val Lys Leu Ser Thr Glu Gln Leu Arg
305                 310                 315                 320

Cys Leu Ala His Arg Leu Ser Glu Pro Pro Glu Asp Leu Asp Ala Leu
                325                 330                 335

Pro Leu Asp Leu Leu Leu Phe Leu Asn Pro Asp Ala Phe Ser Gly Pro
            340                 345                 350

Gln Ala Cys Thr Arg Phe Phe Ser Arg Ile Thr Lys Ala Asn Val Asp
        355                 360                 365

Leu Leu Pro Arg Gly Ala Pro Glu Arg Gln Arg Leu Leu Pro Ala Ala
    370                 375                 380

Leu Ala Cys Trp Gly Val Arg Gly Ser Leu Leu Ser Glu Ala Asp Val
385                 390                 395                 400

Arg Ala Leu Gly Gly Leu Ala Cys Asp Leu Pro Gly Arg Phe Val Ala
                405                 410                 415

Glu Ser Ala Glu Val Leu Leu Pro Arg Leu Val Ser Cys Pro Gly Pro
            420                 425                 430

Leu Asp Gln Asp Gln Gln Glu Ala Ala Arg Ala Ala Leu Gln Gly Gly
        435                 440                 445

Gly Pro Pro Tyr Gly Pro Pro Ser Thr Trp Ser Val Ser Thr Met Asp
    450                 455                 460

Ala Leu Arg Gly Leu Leu Pro Val Leu Gly Gln Pro Ile Ile Arg Ser
465                 470                 475                 480

Ile Pro Gln Gly Ile Val Ala Ala Trp Arg Gln Arg Ser Ser Arg Asp
                485                 490                 495

Pro Ser Trp Arg Gln Pro Glu Arg Thr Ile Leu Arg Pro Arg Phe Arg
            500                 505                 510

Arg Glu Val Glu Lys Thr Ala Cys Pro Ser Gly Lys Lys Ala Arg Glu
        515                 520                 525

Ile Asp Glu Ser Leu Ile Phe Tyr Lys Lys Trp Glu Leu Glu Ala Cys
    530                 535                 540

Val Asp Ala Ala Leu Leu Ala Thr Gln Met Asp Arg Val Asn Ala Ile
545                 550                 555                 560

Pro Phe Thr Tyr Glu Gln Leu Asp Val Leu Lys His Lys Leu Asp Glu
                565                 570                 575

Leu Tyr Pro Gln Gly Tyr Pro Glu Ser Val Ile Gln His Leu Gly Tyr
            580                 585                 590

Leu Phe Leu Lys Met Ser Pro Glu Asp Ile Arg Lys Trp Asn Val Thr
        595                 600                 605

Ser Leu Glu Thr Leu Lys Ala Leu Leu Glu Val Asn Lys Gly His Glu
    610                 615                 620

Met Ser Pro Gln Val Ala Thr Leu Ile Asp Arg Phe Val Lys Gly Arg
625                 630                 635                 640

Gly Gln Leu Asp Lys Asp Thr Leu Asp Thr Leu Thr Ala Phe Tyr Pro
                645                 650                 655

Gly Tyr Leu Cys Ser Leu Ser Pro Glu Glu Leu Ser Ser Val Pro Pro
            660                 665                 670

Ser Ser Ile Trp Ala Val Arg Pro Gln Asp Leu Asp Thr Cys Asp Pro
```

```
        675                 680                 685

Arg Gln Leu Asp Val Leu Tyr Pro Lys Ala Arg Leu Ala Phe Gln Asn
    690                 695                 700

Met Asn Gly Ser Glu Tyr Phe Val Lys Ile Gln Ser Phe Leu Gly Gly
705                 710                 715                 720

Ala Pro Thr Glu Asp Leu Lys Ala Leu Ser Gln Gln Asn Val Ser Met
                725                 730                 735

Asp Leu Ala Thr Phe Met Lys Leu Arg Thr Asp Ala Val Leu Pro Leu
            740                 745                 750

Thr Val Ala Glu Val Gln Lys Leu Leu Gly Pro His Val Glu Gly Leu
        755                 760                 765

Lys Ala Glu Glu Arg His Arg Pro Val Arg Asp Trp Ile Leu Arg Gln
    770                 775                 780

Arg Gln Asp Asp Leu Asp Thr Leu Gly Leu Gly Leu Gln Gly Gly Ile
785                 790                 795                 800

Pro Asn Gly Tyr Leu Val Leu Asp Leu Ser Val Gln Glu Ala Leu Ser
                805                 810                 815

Gly Thr Pro Cys Leu Leu Gly Pro Gly Pro Val Leu Thr Val Leu Ala
            820                 825                 830

Leu Leu Leu Ala Ser Thr Leu Ala
        835                 840


<210> SEQ ID NO 9
<211> LENGTH: 21
<212> TYPE: PRT
<213> ORGANISM: Artificial Sequence
<220> FEATURE:
<223> OTHER INFORMATION: EGFRvIII amino acid sequence

<400> SEQUENCE: 9

Pro Ala Ser Arg Ala Leu Glu Glu Lys Lys Gly Asn Tyr Val Val Thr
 1               5                  10                  15

Asp His Gly Ser Cys
            20


<210> SEQ ID NO 10
<211> LENGTH: 162
<212> TYPE: PRT
<213> ORGANISM: Artificial Sequence
<220> FEATURE:
<223> OTHER INFORMATION: EGFRvIIIx5 amino acid sequence

<400> SEQUENCE: 10

Ala Ser Lys Val Leu Pro Ala Ser Arg Ala Leu Glu Glu Lys Lys Gly
 1               5                  10                  15

Asn Tyr Val Val Thr Asp His Gly Ser Cys Ala Asp Gly Ser Val Lys
            20                  25                  30

Thr Ser Ala Ser Lys Val Ala Pro Ala Ser Arg Ala Leu Glu Glu Lys
        35                  40                  45

Lys Gly Asn Tyr Val Val Thr Asp His Gly Ser Cys Gly Asp Gly Ser
    50                  55                  60

Ile Lys Leu Ser Lys Val Leu Pro Ala Ser Arg Ala Leu Glu Glu Lys
65                  70                  75                  80

Lys Gly Asn Tyr Val Val Thr Asp His Gly Ser Cys Ala Asp Gly Ser
                85                  90                  95

Val Lys Ala Ser Lys Val Ala Pro Ala Ser Arg Ala Leu Glu Glu Lys
            100                 105                 110
```

```
Lys Gly Asn Tyr Val Val Thr Asp His Gly Ser Cys Gly Asp Gly Ser
        115                 120                 125

Ile Lys Leu Ser Lys Val Leu Pro Ala Ser Arg Ala Leu Glu Glu Lys
    130                 135                 140

Lys Gly Asn Tyr Val Val Thr Asp His Gly Ser Cys Ala Asp Gly Ser
145                 150                 155                 160

Val Lys


<210> SEQ ID NO 11
<211> LENGTH: 588
<212> TYPE: PRT
<213> ORGANISM: Artificial Sequence
<220> FEATURE:
<223> OTHER INFORMATION: Mesothelin35-622 amino acid sequence

<400> SEQUENCE: 11

Arg Thr Leu Ala Gly Glu Thr Gly Gln Glu Ala Ala Pro Leu Asp Gly
 1               5                  10                  15

Val Leu Thr Asn Pro Pro Asn Ile Ser Ser Leu Ser Pro Arg Gln Leu
            20                  25                  30

Leu Gly Phe Pro Cys Ala Glu Val Ser Gly Leu Ser Thr Glu Arg Val
        35                  40                  45

Arg Glu Leu Ala Val Ala Leu Ala Gln Lys Asn Val Lys Leu Ser Thr
    50                  55                  60

Glu Gln Leu Arg Cys Leu Ala His Arg Leu Ser Glu Pro Pro Glu Asp
65                  70                  75                  80

Leu Asp Ala Leu Pro Leu Asp Leu Leu Leu Phe Leu Asn Pro Asp Ala
                85                  90                  95

Phe Ser Gly Pro Gln Ala Cys Thr Arg Phe Phe Ser Arg Ile Thr Lys
            100                 105                 110

Ala Asn Val Asp Leu Leu Pro Arg Gly Ala Pro Glu Arg Gln Arg Leu
        115                 120                 125

Leu Pro Ala Ala Leu Ala Cys Trp Gly Val Arg Gly Ser Leu Leu Ser
    130                 135                 140

Glu Ala Asp Val Arg Ala Leu Gly Gly Leu Ala Cys Asp Leu Pro Gly
145                 150                 155                 160

Arg Phe Val Ala Glu Ser Ala Glu Val Leu Leu Pro Arg Leu Val Ser
                165                 170                 175

Cys Pro Gly Pro Leu Asp Gln Asp Gln Gln Glu Ala Ala Arg Ala Ala
            180                 185                 190

Leu Gln Gly Gly Gly Pro Pro Tyr Gly Pro Pro Ser Thr Trp Ser Val
        195                 200                 205

Ser Thr Met Asp Ala Leu Arg Gly Leu Leu Pro Val Leu Gly Gln Pro
    210                 215                 220

Ile Ile Arg Ser Ile Pro Gln Gly Ile Val Ala Ala Trp Arg Gln Arg
225                 230                 235                 240

Ser Ser Arg Asp Pro Ser Trp Arg Gln Pro Glu Arg Thr Ile Leu Arg
                245                 250                 255

Pro Arg Phe Arg Arg Glu Val Glu Lys Thr Ala Cys Pro Ser Gly Lys
            260                 265                 270

Lys Ala Arg Glu Ile Asp Glu Ser Leu Ile Phe Tyr Lys Lys Trp Glu
        275                 280                 285

Leu Glu Ala Cys Val Asp Ala Ala Leu Leu Ala Thr Gln Met Asp Arg
    290                 295                 300

Val Asn Ala Ile Pro Phe Thr Tyr Glu Gln Leu Asp Val Leu Lys His
```

```
305                 310                 315                 320

Lys Leu Asp Glu Leu Tyr Pro Gln Gly Tyr Pro Glu Ser Val Ile Gln
                325                 330                 335

His Leu Gly Tyr Leu Phe Leu Lys Met Ser Pro Glu Asp Ile Arg Lys
            340                 345                 350

Trp Asn Val Thr Ser Leu Glu Thr Leu Lys Ala Leu Leu Glu Val Asn
        355                 360                 365

Lys Gly His Glu Met Ser Pro Gln Val Ala Thr Leu Ile Asp Arg Phe
    370                 375                 380

Val Lys Gly Arg Gly Gln Leu Asp Lys Asp Thr Leu Asp Thr Leu Thr
385                 390                 395                 400

Ala Phe Tyr Pro Gly Tyr Leu Cys Ser Leu Ser Pro Glu Glu Leu Ser
                405                 410                 415

Ser Val Pro Pro Ser Ser Ile Trp Ala Val Arg Pro Gln Asp Leu Asp
            420                 425                 430

Thr Cys Asp Pro Arg Gln Leu Asp Val Leu Tyr Pro Lys Ala Arg Leu
        435                 440                 445

Ala Phe Gln Asn Met Asn Gly Ser Glu Tyr Phe Val Lys Ile Gln Ser
    450                 455                 460

Phe Leu Gly Gly Ala Pro Thr Glu Asp Leu Lys Ala Leu Ser Gln Gln
465                 470                 475                 480

Asn Val Ser Met Asp Leu Ala Thr Phe Met Lys Leu Arg Thr Asp Ala
                485                 490                 495

Val Leu Pro Leu Thr Val Ala Glu Val Gln Lys Leu Leu Gly Pro His
            500                 505                 510

Val Glu Gly Leu Lys Ala Glu Glu Arg His Arg Pro Val Arg Asp Trp
        515                 520                 525

Ile Leu Arg Gln Arg Gln Asp Asp Leu Asp Thr Leu Gly Leu Gly Leu
    530                 535                 540

Gln Gly Gly Ile Pro Asn Gly Tyr Leu Val Leu Asp Leu Ser Val Gln
545                 550                 555                 560

Glu Ala Leu Ser Gly Thr Pro Cys Leu Leu Gly Pro Gly Pro Val Leu
                565                 570                 575

Thr Val Leu Ala Leu Leu Leu Ala Ser Thr Leu Ala
            580                 585


<210> SEQ ID NO 12
<211> LENGTH: 88
<212> TYPE: PRT
<213> ORGANISM: Artificial Sequence
<220> FEATURE:
<223> OTHER INFORMATION: ActAN100* amino acid sequence

<400> SEQUENCE: 12

Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser
```

85

<210> SEQ ID NO 13
<211> LENGTH: 63
<212> TYPE: DNA
<213> ORGANISM: Artificial Sequence
<220> FEATURE:
<223> OTHER INFORMATION: EGFRvIII nucleotide sequence 1

<400> SEQUENCE: 13
ccagctagtc gtgcattaga ggagaaaaag gggaattacg tggtgacgga tcatggatcg 60
tgt 63

<210> SEQ ID NO 14
<211> LENGTH: 63
<212> TYPE: DNA
<213> ORGANISM: Artificial Sequence
<220> FEATURE:
<223> OTHER INFORMATION: EGFRvIII nucleotide sequence 2

<400> SEQUENCE: 14
cctgcatcac gagcacttga agagaaaaaa ggaaactatg ttgtgaccga tcatggtagc 60
tgc 63

<210> SEQ ID NO 15
<211> LENGTH: 63
<212> TYPE: DNA
<213> ORGANISM: Artificial Sequence
<220> FEATURE:
<223> OTHER INFORMATION: EGFRvIII nucleotide sequence 3

<400> SEQUENCE: 15
ccagcatcta gagctttaga ggaaaagaag ggtaactatg tcgtaacaga tcatggaagt 60
tgt 63

<210> SEQ ID NO 16
<211> LENGTH: 63
<212> TYPE: DNA
<213> ORGANISM: Artificial Sequence
<220> FEATURE:
<223> OTHER INFORMATION: EGFRvIII nucleotide sequence 4

<400> SEQUENCE: 16
ccagcttctc gcgcattaga agaaaagaaa ggcaattatg ttgtaacaga ccatggtagt 60
tgt 63

<210> SEQ ID NO 17
<211> LENGTH: 63
<212> TYPE: DNA
<213> ORGANISM: Artificial Sequence
<220> FEATURE:
<223> OTHER INFORMATION: EGFRvIII nucleotide sequence 5

<400> SEQUENCE: 17
ccggcttctc gtgcgctaga agagaagaaa ggaaattacg tagttacaga ccacggctct 60
tgc 63

<210> SEQ ID NO 18
<211> LENGTH: 231
<212> TYPE: DNA
<213> ORGANISM: Artificial Sequence
<220> FEATURE:
<223> OTHER INFORMATION: hly promoter nucleotide sequence

<400> SEQUENCE: 18

```
tcctttgatt agtatattcc tatcttaaag ttacttttat gtggaggcat taacatttgt     60

taatgacgtc aaaaggatag caagactaga ataaagctat aaagcaagca tataatattg    120

cgtttcatct ttagaagcga atttcgccaa tattataatt atcaaaagag aggggtggca    180

aacggtattt ggcattatta ggttaaaaaa tgtagaagga gagtgaaacc c            231
```

<210> SEQ ID NO 19
<211> LENGTH: 1323
<212> TYPE: DNA
<213> ORGANISM: Artificial Sequence
<220> FEATURE:
<223> OTHER INFORMATION: LLO441 nucleotide sequence

<400> SEQUENCE: 19

```
atgaaaaaaa taatgctagt ttttattaca cttatattag ttagtctacc aattgcgcaa     60

caaactgaag caaaggatgc atctgcattc aataaagaaa attcaatttc atccatggca    120

ccaccagcat ctccgcctgc aagtcctaag acgccaatcg aaaagaaaca cgcggatgaa    180

atcgataagt atatacaagg attggattac aataaaaaca atgtattagt ataccacgga    240

gatgcagtga caaatgtgcc gccaagaaaa ggttacaaag atggaaatga atatattgtt    300

gtggagaaaa agaagaaatc catcaatcaa aataatgcag acattcaagt tgtgaatgca    360

atttcgagcc taacctatcc aggtgctctc gtaaaagcga attcggaatt agtagaaaat    420

caaccagatg ttctccctgt aaaacgtgat tcattaacac tcagcattga tttgccaggt    480

atgactaatc aagacaataa aatagttgta aaaaatgcca ctaaatcaaa cgttaacaac    540

gcagtaaata cattagtgga aagatggaat gaaaaatatg ctcaagctta tccaaatgta    600

agtgcaaaaa ttgattatga tgacgaaatg gcttacagtg aatcacaatt aattgcgaaa    660

tttggtacag catttaaagc tgtaaataat agcttgaatg taaacttcgg cgcaatcagt    720

gaagggaaaa tgcaagaaga agtcattagt tttaaacaaa tttactataa cgtgaatgtt    780

aatgaaccta caagaccttc cagatttttc ggcaaagctg ttactaaaga gcagttgcaa    840

gcgcttggag tgaatgcaga aaatcctcct gcatatatct caagtgtggc gtatggccgt    900

caagtttatt tgaaattatc aactaattcc catagtacta aagtaaaagc tgcttttgat    960

gctgccgtaa gcggaaaatc tgtctcaggt gatgtagaac taacaaatat catcaaaaat   1020

tcttccttca aagccgtaat ttacggaggt tccgcaaaag atgaagttca aatcatcgac   1080

ggcaacctcg gagacttacg cgatattttg aaaaaaggcg ctacttttaa tcgagaaaca   1140

ccaggagttc ccattgctta tacaacaaac ttcctaaaag acaatgaatt agctgttatt   1200

aaaaacaact cagaatatat tgaaacaact tcaaaagctt atacagatgg aaaaattaac   1260

atcgatcact ctggaggata cgttgctcaa ttcaacattt cttgggatga agtaaattat   1320

gat                                                                 1323
```

<210> SEQ ID NO 20
<211> LENGTH: 441
<212> TYPE: PRT
<213> ORGANISM: Artificial Sequence
<220> FEATURE:
<223> OTHER INFORMATION: LLO441 amino acid sequence

<400> SEQUENCE: 20

```
Met Lys Lys Ile Met Leu Val Phe Ile Thr Leu Ile Leu Val Ser Leu
 1               5                  10                  15
```

```
Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430
```

```
Ile Ser Trp Asp Glu Val Asn Tyr Asp
        435                 440


<210> SEQ ID NO 21
<211> LENGTH: 1266
<212> TYPE: DNA
<213> ORGANISM: Artificial Sequence
<220> FEATURE:
<223> OTHER INFORMATION: LLO441 PEST nucleotide sequence

<400> SEQUENCE: 21

atgaaaaaaa taatgctagt ttttattaca cttatattag ttagtctacc aattgcgcaa     60

caaactgaag caaaggatgc atctgcattc aatacgccaa tcgaaaagaa acacgcggat    120

gaaatcgata agtatataca aggattggat tacaataaaa acaatgtatt agtataccac    180

ggagatgcag tgacaaatgt gccgccaaga aaaggttaca aagatggaaa tgaatatatt    240

gttgtggaga aaaagaagaa atccatcaat caaaataatg cagacattca agttgtgaat    300

gcaatttcga gcctaaccta tccaggtgct ctcgtaaaag cgaattcgga attagtagaa    360

aatcaaccag atgttctccc tgtaaaacgt gattcattaa cactcagcat tgatttgcca    420

ggtatgacta atcaagacaa taaaatagtt gtaaaaaatg ccactaaatc aaacgttaac    480

aacgcagtaa atacattagt ggaaagatgg aatgaaaaat atgctcaagc ttatccaaat    540

gtaagtgcaa aaattgatta tgatgacgaa atggcttaca gtgaatcaca attaattgcg    600

aaatttggta cagcatttaa agctgtaaat aatagcttga atgtaaactt cggcgcaatc    660

agtgaaggga aaatgcaaga agaagtcatt agttttaaac aaatttacta taacgtgaat    720

gttaatgaac ctacaagacc ttccagattt ttcggcaaag ctgttactaa agagcagttg    780

caagcgcttg gagtgaatgc agaaaatcct cctgcatata tctcaagtgt ggcgtatggc    840

cgtcaagttt atttgaaatt atcaactaat tcccatagta ctaaagtaaa agctgctttt    900

gatgctgccg taagcggaaa atctgtctca ggtgatgtag aactaacaaa tatcatcaaa    960

aattcttcct tcaaagccgt aatttacgga ggttccgcaa aagatgaagt tcaaatcatc   1020

gacggcaacc tcggagactt acgcgatatt ttgaaaaaag gcgctacttt taatcgagaa   1080

acaccaggag ttcccattgc ttatacaaca aacttcctaa aagacaatga attagctgtt   1140

attaaaaaca actcagaata tattgaaaca acttcaaaag cttatacaga tggaaaaatt   1200

aacatcgatc actctggagg atacgttgct caattcaaca tttcttggga tgaagtaaat   1260

tatgat                                                               1266


<210> SEQ ID NO 22
<211> LENGTH: 422
<212> TYPE: PRT
<213> ORGANISM: Artificial Sequence
<220> FEATURE:
<223> OTHER INFORMATION: LLO441 PEST amino acid sequence

<400> SEQUENCE: 22

Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Thr
            20                  25                  30

Pro Ile Glu Lys Lys His Ala Asp Glu Ile Asp Lys Tyr Ile Gln Gly
        35                  40                  45

Leu Asp Tyr Asn Lys Asn Asn Val Leu Val Tyr His Gly Asp Ala Val
    50                  55                  60
```

```
Thr Asn Val Pro Pro Arg Lys Gly Tyr Lys Asp Gly Asn Glu Tyr Ile
65                  70                  75                  80

Val Val Glu Lys Lys Lys Lys Ser Ile Asn Gln Asn Asn Ala Asp Ile
                85                  90                  95

Gln Val Val Asn Ala Ile Ser Ser Leu Thr Tyr Pro Gly Ala Leu Val
            100                 105                 110

Lys Ala Asn Ser Glu Leu Val Glu Asn Gln Pro Asp Val Leu Pro Val
        115                 120                 125

Lys Arg Asp Ser Leu Thr Leu Ser Ile Asp Leu Pro Gly Met Thr Asn
    130                 135                 140

Gln Asp Asn Lys Ile Val Val Lys Asn Ala Thr Lys Ser Asn Val Asn
145                 150                 155                 160

Asn Ala Val Asn Thr Leu Val Glu Arg Trp Asn Glu Lys Tyr Ala Gln
                165                 170                 175

Ala Tyr Pro Asn Val Ser Ala Lys Ile Asp Tyr Asp Asp Glu Met Ala
            180                 185                 190

Tyr Ser Glu Ser Gln Leu Ile Ala Lys Phe Gly Thr Ala Phe Lys Ala
        195                 200                 205

Val Asn Asn Ser Leu Asn Val Asn Phe Gly Ala Ile Ser Glu Gly Lys
    210                 215                 220

Met Gln Glu Glu Val Ile Ser Phe Lys Gln Ile Tyr Tyr Asn Val Asn
225                 230                 235                 240

Val Asn Glu Pro Thr Arg Pro Ser Arg Phe Phe Gly Lys Ala Val Thr
                245                 250                 255

Lys Glu Gln Leu Gln Ala Leu Gly Val Asn Ala Glu Asn Pro Pro Ala
            260                 265                 270

Tyr Ile Ser Ser Val Ala Tyr Gly Arg Gln Val Tyr Leu Lys Leu Ser
        275                 280                 285

Thr Asn Ser His Ser Thr Lys Val Lys Ala Ala Phe Asp Ala Ala Val
    290                 295                 300

Ser Gly Lys Ser Val Ser Gly Asp Val Glu Leu Thr Asn Ile Ile Lys
305                 310                 315                 320

Asn Ser Ser Phe Lys Ala Val Ile Tyr Gly Gly Ser Ala Lys Asp Glu
                325                 330                 335

Val Gln Ile Ile Asp Gly Asn Leu Gly Asp Leu Arg Asp Ile Leu Lys
            340                 345                 350

Lys Gly Ala Thr Phe Asn Arg Glu Thr Pro Gly Val Pro Ile Ala Tyr
        355                 360                 365

Thr Thr Asn Phe Leu Lys Asp Asn Glu Leu Ala Val Ile Lys Asn Asn
    370                 375                 380

Ser Glu Tyr Ile Glu Thr Thr Ser Lys Ala Tyr Thr Asp Gly Lys Ile
385                 390                 395                 400

Asn Ile Asp His Ser Gly Gly Tyr Val Ala Gln Phe Asn Ile Ser Trp
                405                 410                 415

Asp Glu Val Asn Tyr Asp
            420
```

<210> SEQ ID NO 23
<211> LENGTH: 1245
<212> TYPE: DNA
<213> ORGANISM: Artificial Sequence
<220> FEATURE:
<223> OTHER INFORMATION: LLO441 26 nucleotide sequence

<400> SEQUENCE: 23

```
atgaaaaaaa taatgctagt ttttattaca cttatattag ttagtctacc aattgcgcaa     60
caaactgaag caaaggatgc atctgcattc aataaagaag aaatcgataa gtatatacaa    120
ggattggatt acaataaaaa caatgtatta gtataccacg gagatgcagt gacaaatgtg    180
ccgccaagaa aaggttacaa agatggaaat gaatatattg ttgtggagaa aaagaagaaa    240
tccatcaatc aaaataatgc agacattcaa gttgtgaatg caatttcgag cctaacctat    300
ccaggtgctc tcgtaaaagc gaattcggaa ttagtagaaa atcaaccaga tgttctccct    360
gtaaaacgtg attcattaac actcagcatt gatttgccag gtatgactaa tcaagacaat    420
aaaatagttg taaaaaatgc cactaaatca aacgttaaca acgcagtaaa tacattagtg    480
gaaagatgga atgaaaaata tgctcaagct tatccaaatg taagtgcaaa aattgattat    540
gatgacgaaa tggcttacag tgaatcacaa ttaattgcga aatttggtac agcatttaaa    600
gctgtaaata atagcttgaa tgtaaacttc ggcgcaatca gtgaagggaa aatgcaagaa    660
gaagtcatta gttttaaaca aatttactat aacgtgaatg ttaatgaacc tacaagacct    720
tccagatttt tcggcaaagc tgttactaaa gagcagttgc aagcgcttgg agtgaatgca    780
gaaaatcctc ctgcatatat ctcaagtgtg gcgtatggcc gtcaagttta tttgaaatta    840
tcaactaatt cccatagtac taaagtaaaa gctgcttttg atgctgccgt aagcggaaaa    900
tctgtctcag gtgatgtaga actaacaaat atcatcaaaa attcttcctt caaagccgta    960
atttacggag gttccgcaaa agatgaagtt caaatcatcg acggcaacct cggagactta   1020
cgcgatattt tgaaaaaagg cgctactttt aatcgagaaa caccaggagt tcccattgct   1080
tatacaacaa acttcctaaa agacaatgaa ttagctgtta ttaaaaacaa ctcagaatat   1140
attgaaacaa cttcaaaagc ttatacagat ggaaaaatta acatcgatca ctctggagga   1200
tacgttgctc aattcaacat ttcttgggat gaagtaaatt atgat                   1245
```

<210> SEQ ID NO 24
<211> LENGTH: 415
<212> TYPE: PRT
<213> ORGANISM: Artificial Sequence
<220> FEATURE:
<223> OTHER INFORMATION: LLO441 26 amino acid sequence

<400> SEQUENCE: 24

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Glu Ile Asp Lys Tyr Ile Gln Gly Leu Asp Tyr Asn Lys Asn Asn
        35                  40                  45

Val Leu Val Tyr His Gly Asp Ala Val Thr Asn Val Pro Pro Arg Lys
    50                  55                  60

Gly Tyr Lys Asp Gly Asn Glu Tyr Ile Val Val Glu Lys Lys Lys Lys
65                  70                  75                  80

Ser Ile Asn Gln Asn Asn Ala Asp Ile Gln Val Val Asn Ala Ile Ser
                85                  90                  95

Ser Leu Thr Tyr Pro Gly Ala Leu Val Lys Ala Asn Ser Glu Leu Val
            100                 105                 110

Glu Asn Gln Pro Asp Val Leu Pro Val Lys Arg Asp Ser Leu Thr Leu
        115                 120                 125

Ser Ile Asp Leu Pro Gly Met Thr Asn Gln Asp Asn Lys Ile Val Val
    130                 135                 140
```

```
Lys Asn Ala Thr Lys Ser Asn Val Asn Asn Ala Val Asn Thr Leu Val
145                 150                 155                 160

Glu Arg Trp Asn Glu Lys Tyr Ala Gln Ala Tyr Pro Asn Val Ser Ala
                165                 170                 175

Lys Ile Asp Tyr Asp Asp Glu Met Ala Tyr Ser Glu Ser Gln Leu Ile
            180                 185                 190

Ala Lys Phe Gly Thr Ala Phe Lys Ala Val Asn Asn Ser Leu Asn Val
        195                 200                 205

Asn Phe Gly Ala Ile Ser Glu Gly Lys Met Gln Glu Glu Val Ile Ser
    210                 215                 220

Phe Lys Gln Ile Tyr Tyr Asn Val Asn Val Asn Glu Pro Thr Arg Pro
225                 230                 235                 240

Ser Arg Phe Phe Gly Lys Ala Val Thr Lys Glu Gln Leu Gln Ala Leu
                245                 250                 255

Gly Val Asn Ala Glu Asn Pro Pro Ala Tyr Ile Ser Ser Val Ala Tyr
            260                 265                 270

Gly Arg Gln Val Tyr Leu Lys Leu Ser Thr Asn Ser His Ser Thr Lys
        275                 280                 285

Val Lys Ala Ala Phe Asp Ala Ala Val Ser Gly Lys Ser Val Ser Gly
    290                 295                 300

Asp Val Glu Leu Thr Asn Ile Ile Lys Asn Ser Ser Phe Lys Ala Val
305                 310                 315                 320

Ile Tyr Gly Gly Ser Ala Lys Asp Glu Val Gln Ile Ile Asp Gly Asn
                325                 330                 335

Leu Gly Asp Leu Arg Asp Ile Leu Lys Lys Gly Ala Thr Phe Asn Arg
            340                 345                 350

Glu Thr Pro Gly Val Pro Ile Ala Tyr Thr Thr Asn Phe Leu Lys Asp
        355                 360                 365

Asn Glu Leu Ala Val Ile Lys Asn Asn Ser Glu Tyr Ile Glu Thr Thr
    370                 375                 380

Ser Lys Ala Tyr Thr Asp Gly Lys Ile Asn Ile Asp His Ser Gly Gly
385                 390                 395                 400

Tyr Val Ala Gln Phe Asn Ile Ser Trp Asp Glu Val Asn Tyr Asp
                405                 410                 415
```

<210> SEQ ID NO 25
<211> LENGTH: 21
<212> TYPE: PRT
<213> ORGANISM: Artificial Sequence
<220> FEATURE:
<223> OTHER INFORMATION: EGFRvIII amino acid sequence

<400> SEQUENCE: 25

```
Pro Ala Ser Arg Ala Leu Glu Glu Lys Lys Gly Asn Tyr Val Val Thr
 1               5                  10                  15

Asp His Gly Ser Cys
            20
```

<210> SEQ ID NO 26
<211> LENGTH: 13
<212> TYPE: PRT
<213> ORGANISM: Artificial Sequence
<220> FEATURE:
<223> OTHER INFORMATION: cleaver sequence

<400> SEQUENCE: 26

```
Ala Ser Lys Val Leu Ala Asp Gly Ser Val Lys Thr Ser
 1               5                  10
```

<210> SEQ ID NO 27
<211> LENGTH: 11
<212> TYPE: PRT
<213> ORGANISM: Artificial Sequence
<220> FEATURE:
<223> OTHER INFORMATION: cleaver sequence

<400> SEQUENCE: 27

Ala Ser Lys Val Ala Gly Asp Gly Ser Ile Lys
1 5 10

<210> SEQ ID NO 28
<211> LENGTH: 11
<212> TYPE: PRT
<213> ORGANISM: Artificial Sequence
<220> FEATURE:
<223> OTHER INFORMATION: cleaver sequence

<400> SEQUENCE: 28

Leu Ser Lys Val Leu Ala Asp Gly Ser Val Lys
1 5 10

<210> SEQ ID NO 29
<211> LENGTH: 11
<212> TYPE: PRT
<213> ORGANISM: Artificial Sequence
<220> FEATURE:
<223> OTHER INFORMATION: cleaver sequence

<400> SEQUENCE: 29

Ala Ser Lys Val Ala Gly Asp Gly Ser Ile Lys
1 5 10

<210> SEQ ID NO 30
<211> LENGTH: 11
<212> TYPE: PRT
<213> ORGANISM: Artificial Sequence
<220> FEATURE:
<223> OTHER INFORMATION: cleaver sequence

<400> SEQUENCE: 30

Leu Ser Lys Val Leu Ala Asp Gly Ser Val Lys
1 5 10

<210> SEQ ID NO 31
<211> LENGTH: 300
<212> TYPE: DNA
<213> ORGANISM: Artificial Sequence
<220> FEATURE:
<223> OTHER INFORMATION: ActAN100 nucleotide sequence

<400> SEQUENCE: 31
gtgggattaa atagatttat gcgtgcgatg atggtagttt tcattactgc caactgcatt 60
acgattaacc ccgacataat atttgcagcg acagatagcg aagattccag tctaaacaca 120
gatgaatggg aagaagaaaa aacagaagag cagccaagcg aggtaaatac gggaccaaga 180
tacgaaactg cacgtgaagt aagttcacgt gatattgagg aactagaaaa atcgaataaa 240
gtgaaaaata cgaacaaagc agacctaata gcaatgttga aagcaaaagc agagaaaggt 300

<210> SEQ ID NO 32
<211> LENGTH: 100
<212> TYPE: PRT
<213> ORGANISM: Artificial Sequence
<220> FEATURE:

```
<223> OTHER INFORMATION: ActAN100 amino acid sequence

<400> SEQUENCE: 32

Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100
```

EPIDERMAL GROWTH FACTOR RECEPTOR VARIANT III-MESOTHELIN FUSIONS AND METHODS OF USING THE SAME

RELATED APPLICATIONS

This application claims the benefit of U.S. Provisional Application No. 62/146,559, filed on Apr. 13, 2015, and U.S. Provisional Application No. 62/243,397, filed on Oct. 19, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 53161000002SUBSEQUENCELISTING.txt; created Jun. 28, 2016, 45 KB in size.

TECHNICAL FIELD

Provided herein are compositions and methods for eliciting an immune response in a subject. In particular, the present disclosure is directed to fusion proteins comprising an epidermal growth factor receptor variant III (EGFRvIII) polypeptide and a mesothelin polypeptide, and methods of eliciting an immune response using host cells comprising nucleic acid molecules encoding said fusion proteins.

BACKGROUND

Lung cancer is the number one cause of cancer mortality globally and has an estimated incidence of 1.3 million new cases every year. In the U.S. it is the second most commonly diagnosed cancer, over 200,000 people are diagnosed annually with this disease and it is the leading cause of cancer-related deaths, with almost 160,000 people estimated to succumb to the disease each year. Approximately 80% to 85% of the newly diagnosed cases of lung cancer are non-small cell lung cancer (NSCLC) (adenocarcinoma, squamous carcinoma and large cell carcinoma) and 15% to 20% are small cell lung carcinoma. Surgical resection is the most consistent and successful option for cure, but requires completely resectable cancer, which is not feasible for most patients since 70% of patients present with unresectable and/or non-curable disease.

Advances in cancer diagnosis and treatment during the last several decades have provided substantial improvements in outcomes, but some tumors, such as NSCLC, remain difficult to diagnose at an early disease stage and overall survival (OS) continues to be poor for patients who first present with advanced disease or who progress after initial treatment. Additional therapies are needed for these patients

SUMMARY OF THE INVENTION

Disclosed herein are fusion proteins comprising an epidermal growth factor receptor variant III (EGFRvIII) polypeptide fused to a mesothelin polypeptide. In some embodiments, the fusion proteins can comprise one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35-622}$ as set forth in SEQ ID NO:11.

Also provided are nucleic acid molecules encoding the disclosed fusion proteins. In some embodiments, the nucleic acid molecules can comprise one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6.

Disclosed herein are host cells comprising the disclosed nucleic acid molecules. In some embodiments, the host cells can comprise a nucleic acid molecule comprising one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6.

Methods of eliciting an immune response in a subject are also provided. In some embodiments, the methods can comprise administering to the subject a composition comprising a host cell, wherein the host cell comprises a nucleic acid molecule encoding an EGFRvIII-mesothelin fusion protein. In some aspects, the nucleic acid molecule can comprise one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6.

Also disclosed are methods of increasing expression of a mesothelin polypeptide comprising expressing in a host cell a nucleic acid molecule comprising an EGFRvIII polynucleotide and a mesothelin polynucleotide encoding the mesothelin polypeptide. In some embodiments, the nucleic acid molecule can comprise one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6.

Methods of treating cancer in a subject in need of treatment are also provided. In some embodiments, the methods can comprise administering to the subject a therapeutically effective amount of a composition comprising a host cell, wherein the host cell comprises a nucleic acid molecule encoding an EGFRvIII-mesothelin fusion protein. In some embodiments, the nucleic acid molecule can encode a fusion protein comprising one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35-622}$ as set forth in SEQ ID NO:11. In some aspects, the nucleic acid molecule can comprise one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the $mesothelin_{35-622}$ polynucleotide as set forth in SEQ ID NO:6.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 1A and FIG. 1B, illustrates an exemplary schematic of (A) EGFRvIIIx5-$mesothelin_{35-622}$ (also referred to herein as ADU-214) and (B) CRS-207 (shown for reference).

FIG. 3A and FIG. 3B, illustrate an antigen-specific T cell immune response in vaccinated mice. (A) ADU-214 induced robust mesothelin-specific T cell mediated immune responses in Balb/c mice. (B) ADU-214 induced robust EGFRvIII-specific CD8+ T cell immune responses in C3H/HeN mice.

DETAILED DESCRIPTION OF THE INVENTION

Figure 1:
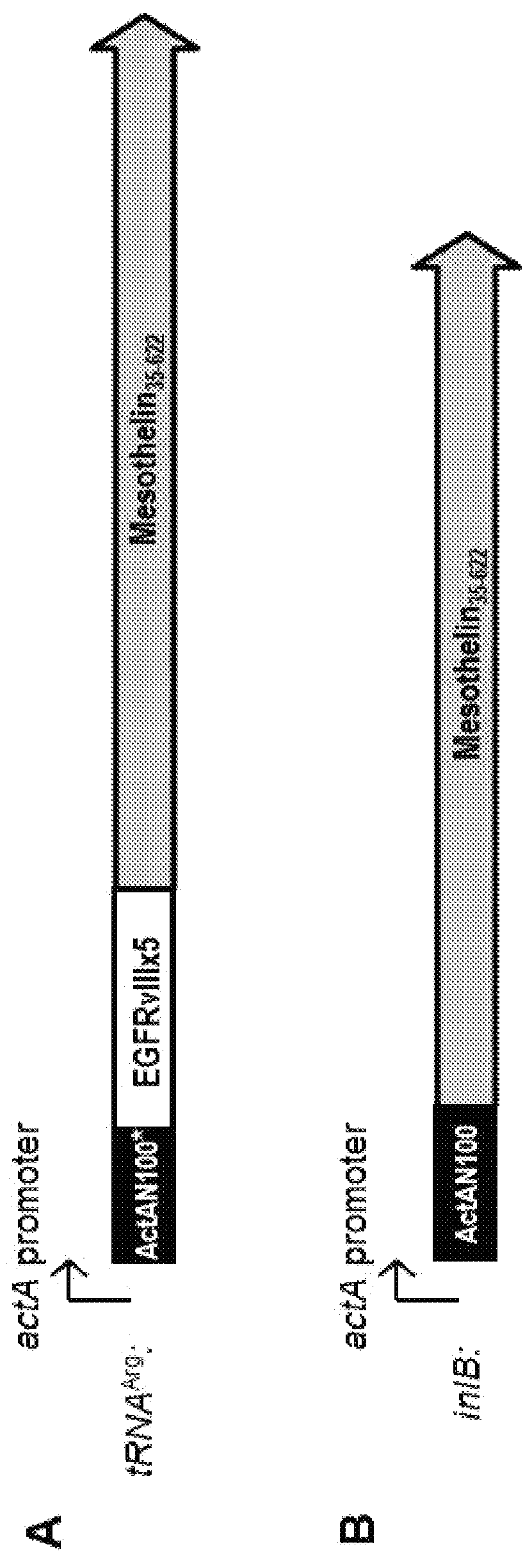
FIG. 1, comprising

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

The following abbreviations are used throughout the disclosure: EGFRvIII (Epidermal Growth Factor Receptor variant III neoantigen junction region); EGFRvIIIx5 (5 copies of EGFRvIII); Meso (mesothelin); ADU-214 (EGFRvIIIx5-$Mesothelin_{35-622}$); Lm (*Listeria monocytogenes*); LADD (double-deleted *Listeria monocytogenes*).

The delta symbol (Δ or ".DELTA.") refers to a deletion. For example, "Δ actA" (or ".DELTA.actA") means that all, or part, of the actA gene is deleted.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have malignancy expressing one or more, and preferably each of, EGFRvIII and mesothelin. In certain embodiments, the subject is suffering from lung cancer, and preferably advanced (stage Mb) or metastatic (stage IV) non-small cell lung cancer (NSCLC) adenocarcinoma.

The terms "percent identical," "sequence identity," and "percent identity" as used herein refers to the percent of amino acids that are the same (i.e. identical) between two or more polypeptides. Sequence identity between two or more polypeptides can be determined by aligning the amino acid sequences of the polypeptides and scoring the number of positions in the aligned polypeptides that contain the same amino acid residue and comparing that to the number of positions in the aligned polypeptides that differ. Polypeptides can differ at a position, for example, by containing a different amino acid (i.e. substitution or mutation) or by lacking an amino acid (i.e. amino acid insertion or amino acid deletion in one or both of the polypeptides). Sequence identity can be calculated by dividing the number of positions that contain the same amino acid residue by the total number of amino acid residues in the polypeptide. Percent identity, for example, can be calculated by dividing the number of positions that contain the same amino acid residue by the total number of amino acid residues in the polypeptide and multiplying by 100.

"Immunogenic fragment thereof" includes portions of fusion proteins that are able to elicit an immunogenic response in a subject. In some aspects, the immunogenic fragment comprises, consists of, or consists essentially of EGFRvIII-mesothelin. In other aspects, the immunogenic fragment comprises, consists of, or consists essentially of signal sequence(s)-EGFRvIII-mesothelin.

As used herein, "fusion protein" refers to a protein made from the joining of two or more polypeptides. Fusion proteins can be generated by chemically conjugating the polypeptides. Preferably, fusion proteins are generated by genetic fusion, in which nucleic acid molecules encoding the individual polypeptides are joined in-frame, such that transcription and translation of the nucleic acid molecules generates a single protein comprising the individual polypeptides. The disclosed fusion proteins may have one or more linker residues between the polypeptides.

As used herein, "signal sequence" refers to polypeptide sequences, and nucleotide sequences encoding the same, that function to drive secretion of the fusion protein. The signal sequence is operably linked to the polypeptide(s) comprising the fusion protein and is translational reading frame with the polypeptide(s) comprising the fusion protein. "Signal sequences" can also be referred to as "secretory signal sequences."

As used herein, "operably linked" refers to the juxtaposition of control sequences, such as a promoter ribosome binding site in a manner that the normal function of the components is maintained. "Control sequences" typically refer to DNA sequences necessary for the expression of an operably linked coding sequence in the host organism. The control sequences can include a promoter, a ribosome binding site and, optionally, a Shine/Dalgarno sequence. Thus, a coding sequence "operably linked" to an encoded signal sequence refers to a configuration wherein the coding sequence is joined to the signal sequence in such a manner that the signal peptide is processed by the host cell and the processed protein is secreted. A signal sequence operably linked to a promoter is joined to the promoter in such a manner that the transcription and translation of the secretion signal sequence is controlled by the promoter, ribosome binding site, and Shine/Dalgarno sequence if required.

As used herein "i) 90% identical, ii) 95% identical, or iii) 99% identical" encompasses at least 90% identical, 91% identical, 92% identical, 93% identical, 94% identical, 95% identical, 96% identical, 97% identical, 98% identical, 99% identical, or 100% identical to the reference item (e.g., a biological sequence).

For EGFRvIII polypeptides and immunogenic fusion proteins containing the same, any sequence variability described herein must occur outside of amino acid residues 7 to 14 of SEQ ID NO:9 (EEKKGNYV). In other words, sequence variability can occur in amino acid residues 1 to 6 of SEQ ID NO:9 (PASRAL) or immunogenic fusion proteins containing the same and/or amino acid residues 15 to 21 of SEQ ID NO:9 (VTDHGSC) or immunogenic fusion proteins containing the same. For example, an EGFRvIII polypeptide comprising an amino acid sequence at least 90% identical to SEQ ID NO:9, encompasses amino acid sequences that are 90% identical, 91% identical, 92% identical, 93% identical, 94% identical, 95% identical, 96% identical, 97% identical, 98% identical, 99% identical, or 100% identical to SEQ ID NO:9, wherein the variability occurs in amino acid residues 1 to 6 or 15 to 21 of SEQ ID NO:9. Accordingly, each EGFRvIII polypeptide and immunogenic fusion protein containing the same will contain amino acid residues 7 to 14 of SEQ ID NO:9 (EEKKGNYV).

EGFRvIII polypeptides can be adjusted in length to include shorter portions of SEQ ID NO:9. For example, in some embodiments, the EGFRvIII polypeptide can comprise, consist, of, or consist essentially of an amino acid sequence at least 90% identical to amino acid residues 6 to 18 of SEQ ID NO:9. In some embodiments, the one or more copies of EGFRvIII polypeptide can comprise, consist, of, or consist essentially of an amino acid sequence at least 90% identical to amino acid residues 6 to 14 of SEQ ID NO:9. As described above, the variability in these shorter polypeptides will occur in amino acid residues 1 to 6 or 15 to 21 of SEQ ID NO:9. Accordingly, for an amino acid sequence at least 90% identical to amino acid residues 6 to 18 of SEQ ID NO:9, the variability can occur at amino acid residue 6 or 15 to 18 of SEQ ID NO:9. For an amino acid sequence at least 90% identical to amino acid residues 6 to 14 of SEQ ID NO:9, the variability can occur at amino acid residue 6.

The disclosed fusion proteins can comprise, consist of, or consist essentially of an EGFRvIII antigen and a mesotehlin antigen. The antigens described herein may include a sequence that is a MHC class I epitope or a MHC class II epitope from the full-length protein sequence. In one embodiment, a described EGFRvIII polynucleotide comprises a sequence encoding at least one MHC class I epitope or at least one MHC class II epitope. Similarly, the EGFRvIII polypeptides described herein include at least one MHC class I epitope or at least one MHC class II epitope. In one embodiment, a described mesothelin polynucleotide comprises a sequence encoding at least one MHC class I epitope or at least one MHC class II epitope. Similarly, the mesothelin polypeptides described herein include at least one MHC class I epitope or at least one MHC class II epitope.

EGFR is a receptor tyrosine kinase critical for cell growth and survival. The EGFR gene is frequently overexpressed or mutated in human cancers, including head and neck, colon, pancreas, breast, ovary, kidney, and malignant gliomas. EGFR receptor variant III (EGFRvIII) results from a 267 amino acid deletion of exons 2 to 7 and the fusion of exon 1 with exon 8, yielding a tumor-specific peptide with a novel glycine at the junction. EGFRvIII exhibits constitutive, ligand-independent signaling.

Mesothelin is a glycosylphosphatidylinositol-linked cell surface glycoprotein that is present on normal mesothelial cells lining the pleura, peritoneum, and pericardium. Mesothelin is also a tumor-associated antigen that is highly expressed by several human tumors, including pancreatic adenocarcinomas, mesothelioma, NSCLC, and ovarian cancers.

The predictive algorithm "BIMAS" ranks potential HLA binding epitopes according to the predictive half-time dissociation of peptide/HLA complexes. The "SYFPEITHI" algorithm ranks peptides according to a score that accounts for the presence of primary and secondary HLA-binding anchor residues. Both computerized algorithms score candidate epitopes based on amino acid sequences within a given protein that have similar binding motifs to previously published HLA binding epitopes. Other algorithms can also be used to identify candidates for further biological testing.

Exemplary nucleotide and amino acid sequences of the fusion proteins and antigen portions of said fusion proteins, as well as nucleic acid molecules encoding the same, are provided in Table 2.

Fusion Proteins

Disclosed herein are fusion proteins comprising an epidermal growth factor receptor variant III (EGFRvIII) polypeptide fused to a mesothelin polypeptide (EGFRvIII-mesothelin fusion proteins).

The fusion protein can comprise one or more copies of an EGFRvIII polypeptide. In some embodiments, the fusion protein can comprise one EGFRvIII polypeptide. In other embodiments, the fusion protein can comprise a plurality of EGFRvIII polypeptides. Suitable numbers of copies of the EGFRvIII polypeptide include, but are not limited to, 2, 3, 4, 5, or more copies. In some embodiments, the fusion protein can comprise one copy of the EGFRvIII polypeptide (EGFRvIIIx1). In some embodiments, the fusion protein can comprise two copies of the EGFRvIII polypeptide (EGFRvIIIx2). In some embodiments the fusion protein can comprise three copies of the EGFRvIII polypeptide (EGFRvIIIx3). In some embodiments, the fusion protein can comprise four copies of the EGFRvIII polypeptide (EGFRvIIIx4). In some embodiments, the fusion protein can comprise five copies of the EGFRvIII polypeptide (EGFRvIIIx5).

In some aspects, each of the one or more copies of the EGFRvIII polypeptide can comprise an amino acid sequence that is at least 90% identical, 91% identical, 92% identical, 93% identical, 94% identical, 95% identical, 96% identical, 97% identical, 98% identical, 99% identical, or 100% identical to SEQ ID NO:9. In some embodiments, for example, the EGFRvIII polypeptide can comprise an amino acid sequence at least i) 90% identical, ii) 95% identical, or iii) 99% identical to SEQ ID NO:9. In other embodiments, the EGFRvIII polypeptide can comprise 2, 3, 4, 5, or more copies of an EGFRvIII polypeptide, each copy having an amino acid sequence at least 90% identical to SEQ ID NO:9.

In some aspects, each of the one or more copies of the EGFRvIII polypeptide can consist of an amino acid sequence that is at least 90% identical, 91% identical, 92% identical, 93% identical, 94% identical, 95% identical, 96% identical, 97% identical, 98% identical, 99% identical, or 100% identical to SEQ ID NO:9. In some aspects, each of the one or more copies of the EGFRvIII polypeptide can consist essentially of an amino acid sequence that is at least 90% identical, 91% identical, 92% identical, 93% identical, 94% identical, 95% identical, 96% identical, 97% identical, 98% identical, 99% identical, or 100% identical to SEQ ID NO:9.

In some embodiments, the one or more copies of EGFRvIII polypeptide can comprise, consist, of, or consist essentially of an amino acid sequence at least i) 90% identical, ii) 95% identical, or iii) 99% identical to amino acid residues 6 to 18 of SEQ ID NO:9. In some embodiments, the one or more copies of EGFRvIII polypeptide can comprise, consist, of, or consist essentially of an amino acid sequence at least i) 90% identical, ii) 95% identical, or iii) 99% identical to amino acid residues 6 to 14 of SEQ ID NO:9.

The EGFRvIII polypeptides can be flanked by one or more cleaver sequences at the N-terminus, C-terminus, or both the N- and C-terminus of the EGFRvIII polypeptide. Cleaver sequences are configured to be processed by proteases present in the subject. Where the EGFRvIII polypeptide comprises 2 or more copies of the EGFRvIII polypeptide, cleaver sequences can be present between the individual copies of the EGFRvIII polypeptides. For example, and without intending to be limiting, SEQ ID NO:10 contains 5 copies of the EGFRvIII polypeptide (each copy of the EGFRvIII polypeptide set forth in SEQ ID NO:9) and cleaver sequences (ASKVL/ADGSVKTS (SEQ ID NO:26), ASKVA/GDGSIK (SEQ ID NO:27), LSKVL/ADGSVK (SEQ ID NO:28), ASKVA/GDGSIK (SEQ ID NO:29), and LSKVL/ADGSVK (SEQ ID NO:30); where "/" represents the EGFRvIII polypeptide). These cleaver sequences are exemplary in nature only. Suitable cleaver sequences are described in U.S. patent application Ser. No. 13/988,076 (U.S. Patent Publ. No. 2014/037662); Toes, et al., J. Exp. Med. (2001) 194: 1-12; Lauer et al., Infect. Immun. (2008) 76: 3742-53; and Sinnathamby et al., J. Immunother. (2009) 32: 856-69, each of which are incorporated by reference in its entirety.

The EGFRvIII polypeptide can be N-terminal or C-terminal to the mesothelin polypeptide. In some embodiments, the EGFRvIII polypeptide can be N-terminal to the mesothelin polypeptide.

Suitable mesothelin polypeptides include mesothelin polypeptides having an amino acid sequence that is at least i) 90% identical, ii) 95% identical, or iii) 99% identical to amino acids 35-622 of mesothelin (referred to herein as "mesothelin$_{35-622}$").

In some aspects, the mesothelin polypeptide can comprise an amino acid sequence that is at least 90% identical, 91% identical, 92% identical, 93% identical, 94% identical, 95% identical, 96% identical, 97% identical, 98% identical, 99% identical, or 100% identical to mesothelin$_{35-622}$ as set forth in SEQ ID NO:11. Thus, in some embodiments, the mesothelin polypeptide can comprise an amino acid sequence at least i) 90% identical, ii) 95% identical, or iii) 99% identical to mesothelin$_{35-622}$ as set forth in SEQ ID NO:11. In some aspects, the mesothelin polypeptide can consist of an amino acid sequence that is at least 90% identical, 91% identical, 92% identical, 93% identical, 94% identical, 95% identical, 96% identical, 97% identical, 98% identical, 99% identical, or 100% identical to mesothelin$_{35-622}$ as set forth in SEQ ID NO:11. In some aspects, the mesothelin polypeptide can consist essentially of an amino acid sequence that is at least 90% identical, 91% identical, 92% identical, 93% identical, 94% identical, 95% identical, 96% identical, 97% identical, 98% identical, 99% identical, or 100% identical to mesothelin$_{35-622}$ as set forth in SEQ ID NO:11.

The fusion protein can comprise, consist of, or consist essentially of one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35-622}$ as set forth in SEQ ID NO:11. The fusion protein can comprise, consist of, or consist essentially of an EGFRvIIIx5 polypeptide comprising an amino acid sequence at least i) 90% identical, ii) 95% identical, or iii) 99% identical to EGFRvIIIx5 as set forth in SEQ ID NO:10 and mesothelin polypeptide comprising an amino acid sequence at least i) 90% identical, ii) 95% identical, or iii) 99% identical to mesothelin$_{35-622}$ as set forth in SEQ ID NO:11. In some embodiments, the fusion protein can comprise, consist of, or consist essentially of an amino acid sequence that is at least i) 90% identical, ii) 95% identical, or iii) 99% identical to EGFRvIIIx5-mesothelin$_{35-622}$ as set forth as amino acid residues 89 to 840 of SEQ ID NO:8. For example, in some aspects, the fusion protein can comprise an amino acid sequence that is at least 90% identical, 91% identical, 92% identical, 93% identical, 94% identical, 95% identical, 96% identical, 97% identical, 98% identical, 99% identical, or 100% identical to EGFRvIIIx5-mesothelin$_{35-622}$ as set forth as amino acid residues 89 to 840 of SEQ ID NO:8. In some aspects, the fusion protein can consist of an amino acid sequence that is at least 90% identical, 91% identical, 92% identical, 93% identical, 94% identical, 95% identical, 96% identical, 97% identical, 98% identical, 99% identical, or 100% identical to EGFRvIIIx5-mesothelin$_{35-622}$ as set forth as amino acid residues 89 to 840 of SEQ ID NO:8. In some aspects, the fusion protein can consist essentially of an amino acid sequence that is at least 90% identical, 91% identical, 92% identical, 93% identical, 94% identical, 95% identical, 96% identical, 97% identical, 98% identical, 99% identical, or 100% identical to EGFRvIIIx5-mesothelin$_{35-622}$ as set forth as amino acid residues 89 to 840 of SEQ ID NO:8.

The disclosed fusion proteins can further comprise a signal sequence. In some embodiments, the fusion protein can further comprise a signal sequence, wherein the signal sequence is in translational reading frame with the EGFRvIII polypeptide and the mesothelin polypeptide. Suitable signal sequences include, for example, ActAN100 (as set forth in SEQ ID NO:32), ActAN100* (as set forth in SEQ ID NO:12), LLO441 (as set forth in SEQ ID NO:20), LLO441ΔPEST (as set forth in SEQ ID NO:22), and LLO441Δ26 (as set forth in SEQ ID NO:24). In some embodiments, the signal sequence can comprise an amino acid sequence at least i) 90% identical, ii) 95% identical, or iii) 99% identical to ActAN100 as set forth in SEQ ID NO:32. In some embodiments, the fusion protein can further comprise a signal sequence, wherein the signal sequence comprises an amino acid sequence that is at least i) 90% identical, ii) 95% identical, or iii) 99% identical to ActAN100* signal sequence as set forth in SEQ ID NO:12. Accordingly, the fusion protein can comprise an amino acid sequence that is at least i) 90% identical, ii) 95% identical, or iii) 99% identical to ActAN100*-EGFRvIIIx5-mesothelin$_{35-622}$ as set forth in SEQ ID NO:8 or an immunogenic fragment thereof. In other aspects, the fusion protein can consist of an amino acid sequence that is at least i) 90% identical, ii) 95% identical, or iii) 99% identical to ActAN100*-EGFRvIIIx5-mesothelin$_{35-622}$ as set forth in SEQ ID NO:8 or an immunogenic fragment thereof. In yet other aspects, the fusion protein can consist essentially of an amino acid sequence that is at least i) 90% identical, ii) 95% identical, or iii) 99% identical to ActAN100*-EGFRvIIIx5-mesothelin$_{35-622}$ as set forth in SEQ ID NO:8 or an immunogenic fragment thereof.

The disclosed fusion proteins can be expressed in a number of suitable host cells as disclosed elsewhere herein. In some embodiments, for example, the fusion protein can be expressed in a bacterium, such as *Listeria monocytogenes* or a genetically modified form thereof.

The disclosed fusion proteins can be used as immunogenic polypeptides to elicit a humoral response, an antigen-specific T cell response (CD4+ and/or CD8+), or both in a subject receiving the fusion protein.

Nucleic Acid Molecules

Disclosed herein are nucleic acid molecules encoding EGFRvIII-mesothelin fusion proteins. The disclosed nucleic acid molecules can encode any of the EGFRvIII-mesothelin fusion proteins disclosed herein.

Throughout the disclosure, EGFRvIII-mesothelin fusion proteins comprising, and nucleic acids encoding said fusion proteins that comprise, one or more EGFRvIII polypeptide are described. The EGFRvIII polypeptide can be encoded by any one of the EGFRvIII nucleotide sequences provided in Table 1. Accordingly, throughout the disclosure, when the EGFRvIII polynucleotide is referred as being "at least i) 90% identical, ii) 95% identical, or iii) 99% identical to SEQ ID NO:4" (the consensus sequence in Table 1), it is intended to include: at least i) 90% identical, ii) 95% identical, or iii) 99% identical to SEQ ID NO:13; at least i) 90% identical, ii) 95% identical, or iii) 99% identical to SEQ ID NO:14; at least 90% identical to SEQ ID NO:15; at least i) 90% identical, ii) 95% identical, or iii) 99% identical to SEQ ID NO:16; and/or at least i) 90% identical, ii) 95% identical, or iii) 99% identical to SEQ ID NO:17. Similarly, the nucleotide sequences encoding the various immunogenic fusion proteins can comprise any one of SEQ ID NO:13-17. Therefore, each EGFRvIII-mesothelin fusion protein provided herein can be encoded by a nucleic acid molecule, wherein the nucleic acid molecule comprises one or more polynucleotides that are at least i) 90% identical, ii) 95% identical, or iii) 99% identical to SEQ ID NO:13, at least i) 90% identical, ii) 95% identical, or iii) 99% identical to SEQ ID NO:14, at least i) 90% identical, ii) 95% identical, or iii) 99% identical to SEQ ID NO:15, at least i) 90% identical, ii) 95% identical, or iii) 99% identical to SEQ ID NO:16, and/or at least i) 90% identical, ii) 95% identical, or iii) 99% identical to SEQ ID NO:17.

TABLE 1

| EGFRvIII Nucleotide Sequence(s) | | |
|---|---|---|
| repeat 1 | | 1 ... 63 |
| (SEQ ID NO: 13) | (1) | CCAGCTAGTCGTGCATTAGAGGAGAAAAAGGGGAATTACGTGGTGACGGATCATGGATCGTGT |
| repeat 2 (SEQ ID NO: 14) | (1) | CCTGCATCACGAGCACTTGAAGAGAAAAAGGAAACTATGTTGTGACCGATCATGGTAGCTGC |
| repeat 3 (SEQ ID NO: 15) | (1) | CCAGCATCTAGAGCTTTAGAGGAAAAGAAGGGTAACTATGTCGTAACAGATCATGGAAGTTGT |
| repeat 4 (SEQ ID NO: 16) | (1) | CCAGCTTCTCGCGCATTAGAAGAAAAGAAAGGCAATTATGTTGTAACAGACCATGGTAGTTGT |
| repeat 5 (SEQ ID NO: 17) | (1) | CCGGCTTCTCGTGCGCTAGAAGAGAAGAAAGGAAATTACGTAGTTACAGACCACGGCTCTTGC |
| Consensus (SEQ ID NO: 4) | (1) | CCdGCwwswmGhGCdyTwGArGArAArAArGGnAAyTAyGTnGTdACvGAyCAyGGhwsbTGy |

The nucleic acid molecule can encode an EGFRvIII-mesothelin fusion protein with one or more EGFRvIII polypeptides. In some embodiments, the nucleic acid molecule can encode an EGFRvIII-mesothelin fusion protein with one EGFRvIII polypeptide (EGFRvIIIx1). In other embodiments, the nucleic acid molecule can encode an EGFRvIII-mesothelin fusion protein with a plurality of EGFRvIII polypeptides. Suitable numbers of EGFRvIII polypeptides encoded by the disclosed nucleic acid molecules include, but are not limited to, 2, 3, 4, 5, or more copies. In some embodiments, the nucleic acid molecules can encode an EGFRvIII-mesothelin fusion protein with 2 copies of the EGFRvIII polypeptide (EGFRvIIIx2). In some embodiments, the nucleic acid molecules can encode an EGFRvIII-mesothelin fusion protein with 3 copies of the EGFRvIII polypeptide (EGFRvIIIx3). In some embodiments, the nucleic acid molecules can encode an EGFRvIII-mesothelin fusion protein with 4 copies of the EGFRvIII polypeptide (EGFRvIIIx4). In some embodiments, the nucleic acid molecules can encode an EGFRvIII-mesothelin fusion protein with 5 copies of the EGFRvIII polypeptide (EGFRvIIIx5).

An exemplary nucleic acid sequence of an EGFRvIII polynucleotide which encodes the EGFRvIII polypeptide is set forth in SEQ ID NO:4. In some embodiments, the disclosed nucleic acid molecules can comprise one or more EGFRvIII polynucleotides that are at least i) 90% identical, ii) 95% identical, or iii) 99% identical to the EGFRvIIIx5 polynucleotide as set forth in SEQ ID NO:4. An exemplary nucleic acid sequence of an EGFRvIIIx5 polynucleotide which encodes the EGFRvIIIx5 polypeptide is set forth in SEQ ID NO:5. In some embodiments, the disclosed nucleic acid molecules can comprise an EGFRvIIIx5 polynucleotide that is at least i) 90% identical, ii) 95% identical, or iii) 99% identical to the EGFRvIIIx5 polynucleotide as set forth in SEQ ID NO:5.

Suitable mesothelin polypeptides encoded by the nucleic acid molecules include mesothelin$_{35\text{-}622}$. The nucleic acid sequence of mesothelin$_{35\text{-}622}$ is set forth in SEQ ID NO:6. Accordingly, the disclosed nucleic acid molecules can encode an EGFRvIII-mesothelin fusion protein, wherein the mesothelin polypeptide is encoded by a polynucleotide that is at least i) 90% identical, ii) 95% identical, or iii) 99% identical to the mesothelin$_{35\text{-}622}$ polynucleotide as set forth in SEQ ID NO:6.

In some embodiments, the nucleic acid molecule can comprise one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35\text{-}622}$ polynucleotide as set forth in SEQ ID NO:6. In some embodiments, the nucleic acid molecule can comprise a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the mesothelin$_{35\text{-}622}$ polynucleotide as set forth in SEQ ID NO:6. In some embodiments, the nucleic acid molecule can comprise a EGFRvIIIx5-mesothelin$_{35\text{-}622}$ polynucleotide that is at least i) 90% identical, ii) 95% identical, or iii) 99% identical to SEQ ID NO:7.

The disclosed nucleic acid molecules can further comprise a promoter, signal sequence, or both. Signal sequences can be used to direct the secretion of the encoded fusion proteins from a host cell. Suitable promoters include, for example, actA (as set forth in SEQ ID NO:2) or hly (as set forth in SEQ ID NO:18). In some embodiments, the nucleic acid molecules can further comprise a promoter, wherein the promoter comprises a nucleotide sequence that is at least i) 90% identical, ii) 95% identical, or iii) 99% identical to the actA promoter as set forth in SEQ ID NO:2. In some embodiments, the nucleic acid molecules can further comprise a promoter, wherein the promoter comprises a nucleotide sequence that is at least 90% identical to the hly promoter as set forth in SEQ ID NO:18. In some embodiments, the nucleic acid molecules can further comprise a signal sequence that is in translational frame with the nucleotide sequence encoding the EGFRvIII polypeptide and the nucleotide sequence encoding the mesothelin polypeptide. Signal sequences can be used to direct the secretion of the encoded fusion proteins from a host cell. Suitable signal sequences include, for example, ActAN100 (as set forth in SEQ ID NO:31), ActAN100* (as set forth in SEQ ID NO:3), LLO441 (as set forth in SEQ ID NO:19), LLO441ΔPEST (as set forth in SEQ ID NO:21), and LLO441Δ26 (as set forth in SEQ ID NO:23). In some embodiments, the nucleic acid molecules can further comprise a signal sequence, wherein the signal sequence can comprise a nucleotide sequence that is at least i) 90% identical, ii) 95% identical, or iii) 99% identical to the ActAN100 signal sequence as set forth in SEQ ID NO:31. In some embodiments, the nucleic acid molecules can further comprise a signal sequence, wherein the signal sequence can comprise a nucleotide sequence that is at least i) 90% identical, ii) 95% identical, or iii) 99% identical to the ActAN100* signal sequence as set forth in SEQ ID NO:3. In some embodiments, the nucleic acid molecules can further comprise a signal sequence, wherein the signal sequence can comprise a nucleotide sequence that is at least i) 90% identical, ii) 95% identical, or iii) 99% identical to the LLO441 signal sequence as set forth in SEQ ID NO:19. In some embodiments, the nucleic acid molecules can further comprise a signal sequence, wherein the signal sequence can comprise a nucleotide sequence that is at least i) 90% identical, ii) 95% identical, or iii) 99% identical to the LLO441ΔPEST signal sequence as set forth in SEQ ID NO:21. In some embodiments, the nucleic acid molecules can further comprise a signal sequence, wherein the signal sequence can comprise a nucleotide sequence that is at least i) 90% identical, ii) 95% identical, or iii) 99% identical to the LLO441Δ26 signal sequence as set forth in SEQ ID NO:23. Accordingly, in some embodiments, the nucleic acid molecule can comprise, consist of, or consist essentially of a polynucleotide that is at least i) 90% identical, ii) 95% identical, or iii) 99% identical to base pairs actAp-ActAN100*-EFGRvIIIx5-mesothelin$_{35\text{-}622}$ as set forth in SEQ ID NO:1.

In some embodiments, the nucleic acid molecule can encode an EGFRvIII-mesothelin fusion protein, wherein the fusion protein comprises one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35\text{-}622}$ as set forth in SEQ ID NO:11.

In some embodiments, nucleic acid molecule can encode an EGFRvIII-mesothelin fusion protein, wherein the fusion protein comprises an EGFRvIIIx5 polypeptide comprising an amino acid sequence at least i) 90% identical, ii) 95% identical, or iii) 99% identical to EGFRvIIIx5 as set forth in SEQ ID NO:10 and mesothelin polypeptide comprising an amino acid sequence at least i) 90% identical, ii) 95% identical, or iii) 99% identical to mesothelin$_{35\text{-}622}$ as set forth in SEQ ID NO:11.

In some embodiments, the nucleic acid molecule encodes an EGFRvIII-mesothelin fusion protein, wherein the EGFRvIII-mesothelin fusion protein comprises, consists of, or consists essentially of an amino acid sequence that is at least i) 90% identical, ii) 95% identical, or iii) 99% identical to EGFRvIIIx5-mesothelin$_{35\text{-}622}$ as set forth in amino acid residues 89 to 840 in SEQ ID NO:8.

The nucleic acid molecules can further comprise additional nucleic acid sequences including, but not limited to, restriction endonuclease cleavage sites (cloning linkers). The nucleic acid molecules can be generated using a number of suitable restriction endonucleases, wherein the endonuclease cleavage site(s) may remain in the final nucleic acid molecule. SEQ ID NO:1 includes a BamHI cloning linker (GGATCC) and a MfeI cloning linker (CAATTG). One of skill in the art would know that other cloning linkers may be used in place of BamHI and/or MfeI.

Additional nucleic acid sequences that can be included in the nucleic acid molecules include "cleaver sequences" (as described elsewhere herein) which flank the individual EGFRvIII polynucleotides.

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

Host Cells

Host cells comprising any of the nucleic acid molecules disclosed herein are also provided.

Suitable host cells include, for example, bacterium. Host cells can be attenuated, commensal, and/or killed but metabolically active. In an exemplary embodiment, the host cell can be an attenuated, commensal, and/or killed but metabolically active bacterium. Suitable bacterium include, but are not limited to, *Listeria monocytogenes, Shigella flexneri, Escherichia coli, Yersinia enterocolitica, Salmonella typhimurium, Salmonella typhi* or *mycobacterium* species, or modified forms thereof. In some embodiments, for example, the host cell can be *Listeria monocytogenes* or a modified form thereof. Modifications include mutations, alterations, and other genetic changes/variations, as well as heat-treatment or chemical modification, which reduce the toxicity of the host cell to a subject. The bacterium can be modified, for example, to reduce binding to cells within a subject, reduce spread from one cell to another within a subject, reduce extracellular growth in a subject, or reduce intracellular growth in a subject.

Bacterial strains suitable as host cells include those described in U.S. patent application Ser. No. 13/988,076 (U.S. Patent Publ. No. 2014/037662), herein incorporated by reference in its entirety. For example, the host cell can be a live-attenuated strain of *L. monocytogenes* which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding for an EGFRvIII-mesothelin fusion protein. In some embodiments, the *Listeria monocytogenes* can be an actA deletion (ΔactA) mutant, an actA insertion mutant, an inlB deletion (ΔinlB) mutant, an inlB insertion mutant, or a combination thereof. For example, the *Listeria monocytogenes* can be a ΔactA/ΔinlB mutant.

The host cells can comprise nucleic acid molecules encoding an EGFRvIII-mesothelin fusion protein wherein the nucleic acid molecule is integrated into the host cell genome. The nucleic acid molecules can be integrated into the actA locus, inlB locus or $tRNA^{Arg}$ locus. In some embodiments, the nucleic acid molecule can be integrated into the actA locus. In some embodiments, the nucleic acid molecule can be integrated into the inlB locus. In some embodiments, the nucleic acid molecule can be integrated into the $tRNA^{Arg}$ locus. Such host cells contain nucleic acids that are under the control of host cell expression sequences and thereby do not require eukaryotic transcriptional or translational elements.

The host cells can comprise the nucleic acid molecule encoding an EGFRvIII-mesothelin fusion protein wherein the nucleic acid molecule is within the host cell extrachromosomally. For example the nucleic acid molecule encoding an EGFRvIII-mesothelin fusion protein can be inserted into an expression cassette on an episomal plasmid within the host cell.

Provided herein are recombinant *Listeria* bacterium that are modified to comprise any of the disclosed nucleic acid molecules. The nucleic acid molecule can be present in the *Listeria* extrachromosomally, or may be integrated into the bacterial genome. In some embodiments, for example, the host cell can be a *Listeria monocytogenes* ΔactA/ΔinlB mutant having a nucleic acid molecule encoding an EGFRvIII-mesothelin fusion protein integrated into the $tRNA^{Arg}$ locus. The *Listeria* can be utilized as an expression platform for expressing the disclosed fusion proteins which are heterologous to the host cell. Such expression can lead to, for example, an immune response to the heterologous fusion protein in a subject containing the host cell.

ADU-214 is a live-attenuated strain of Lm (Lm ΔactA/ΔinlB) engineered to express EGFRvIII and mesothelin. Expression of EGFRvIII-hMeso is driven from the Lm actA promoter, which is highly induced when Lm has infected host cells. The actA gene resides in the PrfA regulon, a series of Lm virulence genes whose expression is controlled and induced by PrfA, a transcriptional activator protein that is induced in the context of the infected host cell. The EGFRvIII-mesothelin expression cassette in ADU-214 exclusively utilizes Lm transcription, translation and secretion machinery and it does not contain any mammalian expression elements (such as promoter or terminator regions characteristic of mammalian expression systems). Therefore, unlike plasmid DNA- or viral-based vectors that must utilize the mammalian host cell machinery to express a designated gene of interest, and by definition, where gene transfer is a prerequisite for gene expression, Lm is a "self-contained" free-living organism. Within infected cells of the vaccinated host, the prokaryotic expression machinery of ADU-214 is utilized exclusively to synthesize the EGFRvIII-mesothelin fusion protein within the bacterium, which is subsequently secreted into the host cell cytoplasm for antigen processing and presentation.

The host cells can be combined with a pharmaceutically acceptable excipient.

Also provided herein are vaccines comprising the disclosed host cells and a pharmaceutically acceptable excipient. The vaccines can be administered to a subject in an amount sufficient to elicit an appropriate immune response as disclosed herein.

Method of Eliciting an Immune Response

Also disclosed herein are methods of eliciting an immune response in a subject comprising administering to the subject a composition comprising a host cell, wherein the host cell comprises a nucleic acid molecule encoding an EGFRvIII-mesothelin fusion protein.

The disclosed methods can be carried out using host cells comprising any of the disclosed nucleic acid molecules. In some embodiments, the methods can comprise administering to the subject a composition comprising a host cell, wherein the host cell comprises a nucleic acid molecule encoding an EGFRvIII-mesothelin fusion protein, the nucleic acid molecule comprising a nucleotide sequence that is at least i) 90% identical, ii) 95% identical, or iii) 99% identical to actAp-ActAN100*-EGFRvIII-mesothelin$_{35-622}$ as set forth in SEQ ID NO:1. In some embodiments, the methods can comprise administering to the subject a composition comprising a host cell, wherein the host cell comprises one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the $mesothelin_{35-622}$ polynucleotide as set forth in SEQ ID NO:6. In some embodiments, the methods can comprise administering to the subject a composition comprising a host cell, wherein the host cell comprises a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the $mesothelin_{35-622}$ polynucleotide as set forth in SEQ ID NO:6. In some embodiments, the methods can comprise administering to the subject a composition comprising a host cell, wherein the host cell comprises a EGFRvIIIx5-$mesothelin_{35-622}$ polynucleotide that is at least i) 90% identical, ii) 95% identical, or iii) 99% identical to SEQ ID NO:7.

Any of the host cells disclosed herein are suitable for use in the disclosed methods. For example, the host cell can be a live-attenuated strain of *L. monocytogenes* which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding for an EGFRvIII-mesothelin fusion protein. In some embodiments, the *Listeria monocytogenes* can be an actA deletion mutant, an actA insertion mutant, an inlB deletion mutant, an inlB insertion mutant, or a combination thereof. For example, the *Listeria monocytogenes* can be a ΔactA/ΔinlB mutant.

The host cells administered to the subject can comprise a nucleic acid molecule encoding an EGFRvIII-mesothelin fusion protein wherein the nucleic acid molecule is integrated into the host cell genome. In some embodiments, the nucleic acid molecule can be integrated into the actA locus. In some embodiments, the nucleic acid molecule can be integrated into the inlB locus. In some embodiments, the nucleic acid molecule can be integrated into the $tRNA^{Arg}$ locus. The host cells administered to the subject can comprise a nucleic acid molecule encoding an EGFRvIII-mesothelin fusion protein wherein the nucleic acid molecule is within the host cell extrachromosomally.

Suitable modes of administering the host cell to the subject include, but are not limited to, intravenously, orally, subcutaneously, intradermally, intramuscularly, intraperitoneally, transmucosally, nasal administration, or any combination thereof. In some embodiments, the administering step is performed intravenously.

The host cell can be utilized as an expression platform for expressing the disclosed fusion proteins within the subject, thus eliciting an immune response to the heterologous fusion protein in a subject containing the host cell. For example, the fusion protein can be expressed and secreted from the host cell in the cytosol of an infected cell within the subject. Infected cells include any cell within the subject that can take up the host cell. In some embodiments, the infected cell can be an antigen presenting cell. Antigen presenting cells (APCs) are cells of the immune system used for presenting antigen to T cells. APCs include dendritic cells, monocytes, macrophages, marginal zone Kupffer cells, microglia, Langerhans cells, T cells, and B cells. In some embodiments, the fusion protein can be expressed in one or more cells of the subject.

Any of the disclosed fusion proteins can be used as immunogenic polypeptides to elicit an immune response in a subject. In some embodiments, for example, the methods can comprise administering to the subject a host cell comprising a nucleic acid molecule encoding an EGFRvIII-mesothelin fusion protein, wherein the fusion protein comprises an amino acid sequence that is at least i) 90% identical, ii) 95% identical, or iii) 99% identical to ActAN100*-EGFRvIIIx5-$mesothelin_{35-622}$ as set forth in SEQ ID NO:8 or an immunogenic fragment thereof.

In some embodiments, the methods can comprise administering to the subject a host cell comprising a nucleic acid molecule encoding a EGFRvIII-mesothelin fusion protein, wherein the fusion protein comprises an amino acid sequence that is at least i) 90% identical, ii) 95% identical, or iii) 99% identical to EGFRvIIIx5-$mesothelin_{35-622}$ as set forth as amino acid residues 89 to 840 of SEQ ID NO:8.

In some embodiments, the methods can comprise administering to the subject a host cell comprising a nucleic acid molecule encoding a EGFRvIII-mesothelin fusion protein, wherein the fusion protein comprises one or more EGFRvIII polypeptides each of which comprise an amino acid sequence at least i) 90% identical, ii) 95% identical, or iii) 99% identical to EGFRvIII as set forth in SEQ ID NO:9 and a mesothelin polypeptide comprising an amino acid sequence at least i) 90% identical, ii) 95% identical, or iii) 99% identical to $mesothelin_{35-622}$ as set forth in SEQ ID NO:11.

In some embodiments, for example, the method can comprise administering to the subject a host cell comprising a nucleic acid molecule encoding an EGFRvIII-mesothelin fusion protein, wherein the fusion protein comprises an EGFRvIIIx5 polypeptide comprising an amino acid sequence at least i) 90% identical, ii) 95% identical, or iii) 99% identical to EGFRvIIIx5 as set forth in SEQ ID NO:10 and a mesothelin polypeptide comprising an amino acid sequence at least i) 90% identical, ii) 95% identical, or iii) 99% identical to $mesothelin_{35-622}$ as set forth in SEQ ID NO:11.

The disclosed methods can be used to elicit a mesothelin immune response, an EGFRvIII immune response, immunity against *Listeria*, or any combination thereof. Accordingly, provided are methods of eliciting a mesothelin immune response in a subject comprising administering to the subject a composition comprising a host cell, wherein the host cell comprises a nucleic acid molecule encoding an EGFRvIII-mesothelin fusion protein. Also provided are methods of eliciting an EGFRvIII immune response in a subject comprising administering to the subject a composition comprising a host cell, wherein the host cell comprises a nucleic acid molecule encoding an EGFRvIII-mesothelin fusion protein. Further provided are methods of eliciting immunity against *Listeria* in a subject comprising administering to the subject a composition comprising *Listeria monocytogenes*, wherein the host cell comprises a nucleic acid molecule encoding an EGFRvIII-mesothelin fusion protein.

The disclosed methods can elicit a humoral response, an antigen-specific T cell response (CD4+ and/or CD8+), or both. For example, upon entry of ADU-214 into the cytosol of an infected eukaryotic host cell, the EGFRvIII-mesothelin fusion protein can be expressed and secreted by the host cell and subsequently processed by the infected cell's proteasomal machinery. Protein fragments of the EGFRvIII-mesothelin fusion protein can be presented in the context of MHC Class I and Class II molecules on the surface of APCs, which can result in the induction of systemic EGFRvIII- and mesothelin-specific CD4+ and CD8+ T cell immunity. Additionally, after IV administration, the primary target cells for ADU-214 are believed to be phagocytic cells in the liver and spleen. Infection of these cells can result in the induction of a proinflammatory cytokine cascade initiated by the early production of type I interferons. Importantly, ADU-214 escapes from the phagolysosome into the cytosol of the infected host cells where ADU-214 expresses and secretes the encoded EGFRvIII-mesothelin antigens (in addition to other bacterial products). As a consequence of the immunostimulatory environment and the expression of the EGFRvIII-mesothelin antigens by the host cell, ADU-214 subsequently enables the priming of systemic EGFRvIII-mesothelin-specific T cell immunity.

Method of Increasing Expression of a Mesothelin Polypeptide

Disclosed herein are methods of increasing expression of a mesothelin polypeptide comprising expressing in a host cell a nucleic acid molecule comprising an EGFRvIII polynucleotide and a mesothelin polynucleotide encoding the mesothelin polypeptide.

The disclosed methods can be performed in any host cell that supports, or can be configured to support, transcription of the disclosed nucleic acid molecules and expression of the mesothelin polypeptide including, but not limited to, bacterial cells, viral cells, yeast cells, insect cells, and mammalian cells. The expressing step can be performed by introducing the nucleic acid molecule into a host cell and allowing the host cell machinery to produce the mesothelin polypeptide. Alternatively, the expressing step can be performed by administering the host cell to a cell of interest, wherein the mesothelin polypeptide is produced within said cell of interest. In some embodiments, the expressing step can be performed by infecting a cell of interest with the host cell, wherein the mesothelin polypeptide is produced within the cell of interest. In some embodiments, the expressing step can be performed by administering the host cell to a subject, wherein the mesothelin polypeptide is produced within the subject.

Accordingly, the disclosed methods can be used to increase expression of mesothelin in a subject. The methods can comprise expressing in the subject a nucleic acid molecule comprising an EGFRvIII polynucleotide and a mesothelin polynucleotide encoding the mesothelin polypeptide.

Increasing the expression of mesothelin in a subject can be carried out by administering to the subject a host cell comprising the nucleic acid that encodes the mesothelin polypeptide. Any host cell disclosed herein can be used with the disclosed methods. For example, the host cell can be a live-attenuated bacterial strain, such as *L. monocytogenes*. The *L. monocytogenes* can be genetically modified to comprise an attenuating mutation in actA and/or inlB, and preferably a deletion of all or a portion of actA and inlB (referred to herein as "Lm ΔactA/ΔinlB"), and contain a nucleic acid molecule encoding for an EGFRvIII-mesothelin fusion protein. In some embodiments, the *Listeria monocytogenes* can be an actA deletion mutant, an actA insertion mutant, an inlB deletion mutant, an inlB insertion mutant, or a combination thereof. For example, the *Listeria monocytogenes* can be a ΔactA/ΔinlB mutant.

The host cells can comprise a nucleic acid molecule encoding an EGFRvIII-mesothelin fusion protein wherein the nucleic acid molecule is integrated into the host cell genome. In some embodiments, the nucleic acid molecule can be integrated into the actA locus. In some embodiments, the nucleic acid molecule can be integrated into the inlB locus. In some embodiments, the nucleic acid molecule can be integrated into the $tRNA^{Arg}$ locus. The host cells can comprise a nucleic acid molecule encoding an EGFRvIII-mesothelin fusion protein wherein the nucleic acid molecule is within the host cell extrachromosomally.

Suitable nucleic acid molecules for use in the disclosed methods include those nucleic acid molecules disclosed elsewhere herein. The nucleic acid molecule can comprise a single copy of the EGFRvIII polynucleotide or one or more copies of the EGFRvIII polynucleotide, wherein the EGFRvIII polynucleotide comprises a nucleotide sequence that is at least i) 90% identical, ii) 95% identical, or iii) 99% identical to SEQ ID NO:4. Suitable numbers of copies of the EGFRvIII polynucleotide include, but are not limited to, 2, 3, 4, 5, or more copies. The EGFRvIII polynucleotide(s) can be flanked by one or more nucleotide sequences encoding cleaver sequences.

In some embodiments, the method of increasing expression of a mesothelin polypeptide can comprise expressing in a host cell a nucleic acid molecule comprising a nucleotide sequence that is at least i) 90% identical, ii) 95% identical, or iii) 99% identical to actAp-ActAN100*-EGFRvIII-mesothelin$_{35-622}$ as set forth in SEQ ID NO:1. In some embodiments, the method of increasing expression of a mesothelin polypeptide can comprise expressing in a host cell a nucleic acid molecule comprising one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6. In some embodiments, the method of increasing expression of a mesothelin polypeptide can comprise expressing in a host cell a nucleic acid molecule comprising a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the mesothelin$_{35-622}$ polynucleotide as set forth in SEQ ID NO:6. In some embodiments, the method of increasing expression of a mesothelin polypeptide can comprise expressing in a host cell a nucleic acid molecule comprising a EGFRvIIIx5-mesothelin$_{35-622}$ polynucleotide that is at least i) 90% identical, ii) 95% identical, or iii) 99% identical to SEQ ID NO:7.

The mesothelin polynucleotide can encode for a mesothelin$_{35-622}$ polypeptide. In some embodiments, the mesothelin polypeptide can comprise, consist of, or consist essentially of an amino acid sequence that is at least i) 90% identical, ii) 95% identical, or iii) 99% identical to mesothelin$_{35-622}$ as set forth in SEQ ID NO:11. Accordingly, the disclosed methods can be used to increase the expression level of mesothelin$_{35-622}$.

The nucleic acid molecule can further comprise a signal sequence, a promoter, or both. In some embodiments, the nucleic acid molecule can further comprise a signal sequence, wherein the signal sequence comprises a nucleotide sequence that is at least i) 90% identical, ii) 95% identical, or iii) 99% identical to ActAN100* as set forth in SEQ ID NO:3. In some embodiments, the nucleic acid molecule can further comprise a promoter, wherein the promoter comprises a nucleotide sequence that is at least i) 90% identical, ii) 95% identical, or iii) 99% identical to actA promoter as set forth in SEQ ID NO:2. In some embodiments, the nucleic acid molecule can further comprise a signal sequence and a promoter, where the signal sequence comprises a nucleotide sequence that is at least i) 90% identical, ii) 95% identical, or iii) 99% identical to ActAN100* as set forth in SEQ ID NO:3 and the promoter comprises a nucleotide sequence that is at least i) 90% identical, ii) 95% identical, or iii) 99% identical to actA promoter as set forth in SEQ ID NO:2.

Methods of Treating Cancer in a Subject

The therapeutic concept of cancer vaccines encompasses a broad spectrum of platform technologies intended to induce and enhance a specific adaptive immune response against malignant tumor cells. Multiple vaccine technologies initially developed in relevant nonclinical cancer models have entered into clinical testing in populations of patients with either existing disease or as adjuvant treatments after curative tumor removal. Unfortunately, in NSCLC, the leading cause of cancer-related mortality worldwide, active immunotherapeutic interventions with vaccines have not yet achieved a clinical proof-of-concept by demonstrating a significant benefit with regard to tumor response, delay of tumor recurrence or progression, and ultimately, extension of overall survival (OS). It is believed that this lack of clinical efficacy is primarily due to specific mechanisms of resistance, which enable NSCLC cells to evade immune recognition and to avoid cytotoxic destruction by the antigen-directed T lymphocytes that are induced and activated after therapeutic cancer vaccination. The disclosed methods address these and other problems.

Disclosed herein are methods of treating cancer in a subject in need thereof, said methods comprising administering to the subject a therapeutically effective amount of a composition comprising a host cell, wherein the host cell comprises a nucleic acid molecule encoding an EGFRvIII-mesothelin fusion protein.

EGFRvIII is a unique mutation that is only found in tumor cells, including NSCLC, and not on normal cells in the body. Eliciting a potent and long-lived EGFRvIII-specific T cell and antibody response can both eliminate EGFRvIII-expressing cells and exert immunoselective pressure in favor of those cells not expressing EGFRvIII, potentially facilitating treatment of residual tumor with existing targeted therapeutics. The disclosed methods specifically target only the EGFRvIII neoantigenic region expressed by deletion of exons 2 to 7 of EGFR in tumor cells, not native EGFR, which is required for signal transduction in normal-functioning cell populations. Thus, EGFRvIII-specific immune responses are expected to be restricted to the patient population expressing this EGFR variant. In addition, EGFRvIII can enhance the expression of the mesothelin, a tumor-associated antigen with limited expression on the surface of normal tissues, but highly expressed by several human tumors, including NSCLC. Cytotoxic T lymphocytes (CTLs) induced by immunization with the disclosed compositions are specifically designed to recognize and selectively destroy both host cell-infected cells and tumor cells that over-express EGFRvIII and mesothelin. For example, as a consequence of the immunostimulatory environment and the expression of EGFRvIII and mesothelin by the host cell, an EGFRvIII-mesothelin fusion protein, such as ADU-214, subsequently enables the priming of systemic EGFRvIII- and mesothelin-specific T cell immunity, thereby limiting the growth of antigen-expressing tumors locally. Accordingly, suitable cancers that can be treated with the disclosed methods include mesothelin-expressing cancers, EGFRvIII-expressing cancers, or both. In some embodiments, the cancer can be a mesothelin-expressing cancer. In some aspects, for example, the cancer can have a high level of mesothelin expression. As used herein, "high level of mesothelin expression" refers to an overexpression of the mesothelin protein in the cancerous tissue compared to the level of mesothelin expression in non-cancerous tissue. In some embodiments, the cancer can be an EGFRvIII-expressing cancer. In some embodiments, the cancer can be a mesothelin-expressing cancer and EGFRvIII-expressing cancer.

Preferably, the mesothelin-expressing cancer, EGFRvIII-expressing cancer, or mesothelin-expressing cancer and EGFRvIII-expressing cancer is lung cancer. Lung cancer includes both non-small cell lung cancer (NSCLC) and small cell lung cancer. In a preferred aspect, the disclosed methods can be performed on subjects having NSCLC. NSCLC includes NSCLC adenocarcinoma, NSCLC squamous cell carcinoma, large cell carcinoma, or any combination thereof. In some embodiments, the cancer can be NSCLC adenocarcinoma. In some embodiments, the cancer can be NSCLC squamous cell carcinoma. In some embodiments, the cancer can be large cell carcinoma. In some embodiments, the cancer can be any combination of NSCLC adenocarcinoma, NSCLC squamous cell carcinoma, and large cell carcinoma.

The disclosed methods can be used to treat subjects having advanced (stage Mb) or metastatic (stage IV) NSCLC adenocarcinoma and who have failed standard therapy and/or are progressing. In some embodiments, the lung cancer can be advanced NSCLC adenocarcinoma. In other embodiments, the lung cancer can be metastatic NSCLC adenocarcinoma. Standard therapy for NSCLC includes, but is not limited to, surgery, radiation, chemotherapy, or any combination thereof. Thus, in some aspects, the disclosed methods can be used to treat a subject who had surgery. In other aspects, the disclosed methods can be used to treat a subject who had radiation. In other aspects, the disclosed methods can be used to treat a subject who had chemotherapy. In yet other aspects, the disclosed methods can be used to treat a subject who had any combination of prior surgery, radiation, and chemotherapy.

Any of the host cells disclosed herein are suitable for use in the disclosed methods. For example, the host cell can be *Listeria monocytogenes*. In a preferred aspect, the host cell can be a live-attenuated strain of *Listeria monocytogenes* which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding for an EGFRvIII-mesothelin fusion protein. In some embodiments, the *Listeria monocytogenes* can be an actA deletion (ΔactA) mutant, an actA insertion mutant, an inlB deletion (ΔinlB) mutant, an inlB insertion mutant, or a combination thereof. For example, the *Listeria monocytogenes* can be a ΔactA/ΔinlB mutant.

The host cells administered to the subject can comprise a nucleic acid molecule encoding an EGFRvIII-mesothelin fusion protein wherein the nucleic acid molecule is integrated into the host cell genome. In some embodiments, the nucleic acid molecule can be integrated into the $tRNA^{Arg}$ locus. The host cells administered to the subject can comprise a nucleic acid molecule encoding an EGFRvIII-mesothelin fusion protein wherein the nucleic acid molecule is within the host cell extrachromosomally.

The host cell can be utilized as an expression platform for expressing the EGFRvIII-mesothelin fusion proteins within the subject, thus eliciting an anti-tumor response to EGFRvIII-expressing tumor cells, mesothelin-expressing tumor cells, or both EGFRvIII-expressing and mesothelin-expressing tumor cells. The fusion protein can be expressed and secreted from the host cell in the cytosol of an infected cell within the subject. Infected cells include any cell within the subject that can take up the host cell. In some embodiments, the infected cell can be an antigen presenting cell.

Any of the disclosed fusion proteins can be used as immunogenic polypeptides to elicit an anti-tumor response in a subject. For example, the fusion protein can comprise one or more EGFRvIII polypeptides. In some embodiments, the fusion protein can comprise one EGFRvIII polypeptide. In other embodiments, the fusion protein can comprise a plurality of EGFRvIII polypeptides. Suitable numbers of copies of the EGFRvIII polypeptide include, but are not limited to, 2, 3, 4, 5, or more copies. In some embodiments, for example, the fusion protein can comprise 2, 3, 4, 5, or more copies of the EGFRvIII polypeptide. The EGFRvIII-mesothelin fusion protein can comprise one or more EGFRvIII polypeptide having an amino acid sequence at least i) 90% identical, ii) 95% identical, or iii) 99% identical to SEQ ID NO:9.

Suitable mesothelin polypeptides include mesothelin polypeptides having an amino acid sequence that is at least i) 90% identical, ii) 95% identical, or iii) 99% identical to amino acids 35-622 of mesothelin. For example, the EGFRvIII-mesothelin fusion protein can comprise a mesothelin polypeptide having an amino acid sequence at least i) 90% identical, ii) 95% identical, or iii) 99% identical to mesothelin$_{35-622}$ as set forth in SEQ ID NO:11.

In some embodiments, the methods can comprise administering to the subject a composition comprising a host cell, wherein the host cell comprises a nucleic acid molecule encoding an EGFRvIII-mesothelin fusion protein, wherein the fusion protein comprises, consists of, or consists essentially of an amino acid sequence that is at least i) 90% identical, ii) 95% identical, or iii) 99% identical to EGFRvIIIx5-mesothelin$_{35-622}$ as set forth as amino acid residues 89 to 840 of SEQ ID NO:8. In some aspects, the fusion protein can comprise an amino acid sequence that is at least i) 90% identical, ii) 95% identical, or iii) 99% identical to EGFRvIIIx5-mesothelin$_{35-622}$ as set forth as amino acid residues 89 to 840 of SEQ ID NO:8. In other aspects, the fusion protein can consist of an amino acid sequence that is at least i) 90% identical, ii) 95% identical, or iii) 99% identical to EGFRvIIIx5-mesothelin$_{35-622}$ as set forth as amino acid residues 89 to 840 of SEQ ID NO:8. In yet other aspects, the fusion protein can consist essentially of an amino acid sequence that is at least i) 90% identical, ii) 95% identical, or iii) 99% identical to EGFRvIIIx5-mesothelin$_{35-622}$ as set forth as amino acid residues 89 to 840 of SEQ ID NO:8.

In some embodiments, the methods can comprise administering to the subject a composition comprising a host cell, wherein the host cell comprises a nucleic acid molecule encoding an EGFRvIII-mesothelin fusion protein, wherein the fusion protein comprises, consists of, or consists essentially of one or more EGFRvIII polypeptides each of which comprise an amino acid sequence at least i) 90% identical, ii) 95% identical, or iii) 99% identical to EGFRvIII as set forth in SEQ ID NO:9 and a mesothelin polypeptide comprising an amino acid sequence at least i) 90% identical, ii) 95% identical, or iii) 99% identical to mesothelin$_{35-622}$ as set forth in SEQ ID NO:11. In some embodiments, the methods can comprise administering to the subject a composition comprising a host cell, wherein the host cell comprises a nucleic acid molecule encoding an EGFRvIII-mesothelin fusion protein, wherein the fusion protein comprises, consists of, or consists essentially of an EGFRvIIIx5 polypeptide comprising an amino acid sequence at least i) 90% identical, ii) 95% identical, or iii) 99% identical to EGFRvIIIx5 as set forth in SEQ ID NO:10 and a mesothelin polypeptide comprising an amino acid sequence at least i) 90% identical, ii) 95% identical, or iii) 99% identical to mesothelin$_{35-622}$ as set forth in SEQ ID NO:11.

The disclosed fusion proteins can further comprise a signal sequence. Thus, in some embodiments, the methods can comprise administering to the subject a composition comprising a host cell, wherein the host cell comprises a nucleic acid molecule encoding an EGFRvIII-mesothelin fusion protein, wherein the EGFRvIII-mesothelin fusion protein comprises, consists of, or consists essentially of an amino acid sequence that is at least i) 90% identical, ii) 95% identical, or iii) 99% identical to ActAN100*-EGFRvIIIx5-mesothelin$_{35-622}$ as set forth in SEQ ID NO:8 or an immunogenic fragment thereof.

Suitable nucleic acid molecules for use in the methods include any of those disclosed herein. An exemplary nucleic acid molecule is an EGFRvIIIx5-mesothelin$_{35-622}$ polynucleotide as set forth in SEQ ID NO:7. In some embodiments, for example, the nucleic acid molecule can comprise a nucleotide sequence that it at least i) 90% identical, ii) 95% identical, or iii) 99% identical to EGFRvIIIx5-mesothelin$_{35-622}$ as set forth in SEQ ID NO:7. In some embodiments, the nucleic acid molecule can consist of a nucleotide sequence that it at least i) 90% identical, ii) 95% identical, or iii) 99% identical to EGFRvIIIx5-mesothelin$_{35-622}$ as set forth in SEQ ID NO:7. In some embodiments, the nucleic acid molecule can consist essentially of a nucleotide sequence that it at least i) 90% identical, ii) 95% identical, or iii) 99% identical to EGFRvIIIx5-mesothelin$_{35-622}$ as set forth in SEQ ID NO:7.

In some embodiments, the nucleic acid molecule can comprise, consist of, or consist essentially of one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6. In some embodiments, the nucleic acid molecule can comprise, consist of, or consist essentially of a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the mesothelin$_{35-622}$ polynucleotide as set forth in SEQ ID NO:6.

Suitable nucleic acid molecules can further comprise nucleotide sequences encoding for a promoter, a signal sequence, or both. For example, in some embodiments, the nucleic acid molecule can comprise, consist of, or consist essentially of a nucleotide sequence that is at least i) 90% identical, ii) 95% identical, or iii) 99% identical to actAp-ActAN100*-EGFRvIII-mesothelin$_{35-622}$ as set forth in SEQ ID NO:1. In other embodiments, the nucleic acid molecule can consist of a nucleotide sequence that is at least i) 90% identical, ii) 95% identical, or iii) 99% identical to SEQ ID NO:1. In yet other embodiments, the nucleic acid molecule can consist essentially of a nucleotide sequence that is at least i) 90% identical, ii) 95% identical, or iii) 99% identical to SEQ ID NO:1.

The disclosed methods can further comprise measuring mesothelin levels, detecting EGFRvIII, or both in a biological sample from the subject prior to administering the composition. Methods for measuring mesothelin levels and/or detecting the presence of EGFRvIII in a biological sample from the subject include, but are not limited to, immunohistochemistry (IHC), Western Blotting, microscopy, immunoprecipitation, BCA assays, spectrophotometry, or any combination thereof. Mesothelin levels and/or EGFRvIII can be detected in biological samples including, but are not limited to, blood, lymph fluid, bone marrow, a solid tumor sample, or any combination thereof.

The compositions can further comprise a pharmaceutically acceptable excipient. For example, the host cells can be combined with any suitable buffer, including but not limited to, phosphate-buffered saline (PBS), and glycerol. In an exemplary embodiment, the composition can be formulated in Dulbecco's phosphate-buffered saline (PBS) and glycerol, stored frozen (at or below −60° C.) until administration, and administered by intravenous (IV) infusion in sodium chloride over a suitable period of time. One skilled in the art would know that the period of time for administering the composition depends, in part, on the type of cancer, the severity of the cancer, and the subject's age, weight, etc. Preferably, the composition can be administered over a period of hours. For example, the composition can be administered over a 1-2 hour period. In other embodiments, the composition can be administered in less than 1-2 hours. In yet other embodiments, the composition can be administered in greater than 1-2 hours.

Treatment can include a single dose of the composition or multiple doses of the composition. Thus, the disclosed methods can comprise administering to the subject one or more doses of a composition comprising a host cell, wherein the host cell comprises a nucleic acid molecule encoding an EGFRvIII-mesothelin fusion protein. Factors that can determine the number of doses include, for example, the progression of the cancer, the severity of the cancer symptoms, the frequency of the cancer symptoms, tumor size, or any combination thereof. Without intent to be limiting, the number of doses can increased based upon progression or failure to reduce the progression of the cancer, increased severity or no change in severity of the cancer symptoms, increased frequency or no change in the frequency of the cancer symptoms, increased size or no change in size of the tumor, or any combination thereof. For example, the subject can be administered 1 to 100 doses or more of the composition.

Factors that can determine the dose of the host cell include, for example, the progression of the cancer, the severity of the cancer symptoms, the frequency of the cancer symptoms, tumor size, or any combination thereof. In some embodiments, the composition can comprise about $1\times10^8$ to about $1\times10^9$ colony forming units (CFU) of a host cell. In some aspects, the composition can comprise about $1\times10^8$ CFU of a host cell. In some aspects, the composition can comprise about $1\times10^9$ CFU of a host cell.

The composition can be administered about once every 7 days, about once about every 14 days, about once every 21 days, about once every 28 days, about once every 35 days, about once every 42 days, about once every 49 days, about once every 56 days, about once every 63 days, about once every 70 days, about once every 77 days, about once every 84 days, or about once every 91 days.

Based on the forgoing, those skilled in the art would understand that a subject could be treated for the progression of cancer, the severity of cancer symptoms, the frequency of cancer symptoms, tumor size, or any combination thereof by administering a described dose of any one of the compositions descried herein, where the dosing is repeated at a regular interval as described. Accordingly, in one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 7 days. Furthermore, the compositions described herein could be prepared in a pharmaceutical preparation suitable for such a dose to be administered in this manner. In one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 14 days. Furthermore, the compositions described herein could be prepared in a pharmaceutical preparation suitable for such a dose to be administered in this manner. In one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 21 days. Furthermore, the compositions described herein could be prepared in a pharmaceutical preparation suitable for such a dose to be administered in this manner. In one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 35 days. Furthermore, the compositions described herein could be prepared in a pharmaceutical preparation suitable for such a dose to be administered in this manner. In one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 45 days. Furthermore, the compositions described herein could be prepared in a pharmaceutical preparation suitable for such a dose to be administered in this manner. In one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 60 days. Furthermore, the compositions described herein could be prepared in a pharmaceutical preparation suitable for such a dose to be administered in this manner. In one embodiment a composition may be administered to a subject at a dose of about $1\times10^8$ to about $1\times10^9$ CFU to treat the progression of cancer, the severity of cancer symptoms, the frequency of cancer symptoms, tumor size, or any combination thereof, where the dosing is repeated about once every 90 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 7 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 14 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 21 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 35 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 45 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 60 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 90 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 7 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 14 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 21 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 35 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 45 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 60 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 90 days. Furthermore, the compositions described herein could be prepared in a pharmaceutical preparation suitable for such a dose to be administered in this manner.

Preferably, treatment can include a period of time between doses wherein the composition is not administered to the subject. For example, the methods can comprise administering to the subject a first dose of a composition comprising a host cell, wherein the host cell comprises a nucleic acid molecule encoding an EGFRvIII-mesothelin fusion protein, monitoring the efficacy of the first dose, and, if the first dose is not efficacious, administering to the subject one or more doses of the composition. Factors that can determine the efficacy of the composition include, for example, the progression of the cancer, the severity of the cancer symptoms, the frequency of the cancer symptoms, tumor size, or any combination thereof. Without intent to be limiting, progression or failure to reduce the progression of the cancer, increased severity or no change in severity of the cancer symptoms, increased frequency or no change in the frequency of the cancer symptoms, increased size or no change in size of the tumor, or any combination thereof, can be indications that the first dose of the composition is not efficacious. Suitable periods of time between doses include days, weeks, or months. In some embodiments, the period of time between doses can be about 1 day to about 90 days, about 5 days to about 80 days, about 10 days to about 70 days, about 15 days to about 60 days, about 20 days to about 50 days, or about 25 days to about 40 days. For example, the period between doses can be about 1 day, about 2 days, about 3 days, about 4 days, about 5 days, about 6 days, about 7 days, about 14 days, about 21 days, about 28 days, about 35 days, about 42 days, about 49 days, about 56 days, about 60 days, about 65 days, about 70 days, about 80 days, about 85 days, or about 90 days.

Suitable modes of administering the composition to the subject include, but are not limited to, intravenously, orally, subcutaneously, intradermally, intramuscularly, intraperitoneally, transmucosally, nasal administration, or any combination thereof. In some embodiments, the administering step can be performed intravenously.

Treatment can further comprise administering an antibiotic to the subject after administering the composition. For example, once the final dose of the composition is administered to the patient, and after a suitable interval time, the patient can be given an antibiotic. Thus, in a preferred aspect, the antibiotic is administered after a last dose of the composition. Suitable antibiotics include, but are not limited to, amoxicillin or trimethoprim/sulfamethoxazole in subjects who are allergic to penicillin. One skilled in the art would be able to determine a sufficient dosing and dosing schedule for administering the antibiotic to the subject.

The following examples are provided to further describe some of the embodiments disclosed herein. The examples are intended to illustrate, not to limit, the disclosed embodiments.

EXAMPLES

Methods

Bacterial Strains

The bacterial strains used in the disclosed studies are listed in Table 2.

TABLE 2

| Strain | Alias | Antigen cassette |
|---|---|---|
| Lm11 | Lm ΔactA ΔinlB | none |
| CRS-207 | hMeso38 | $\text{Mesothelin}_{35\text{-}622}$ |
| ADU-214 | PL1304 | $\text{EGFRvIIIx5-Mesothelin}_{35\text{-}622}$ |

Molecular Construction of ADU-214

The 221 base pair (bp) actA promoter and 258 bp modified signal sequence ActAN100* were cloned into a derivative of the pPL2 integration vector as a KpnI-BamHI fragment. A 486 bp sequence encoding 5 copies of EGFRvIII neoantigen junction region (EGFRvIIIx5) were cloned in frame with ActAN100* as a BamHI-MfeI fragment. A 1767 bp sequence encoding amino acids 35-622 of human mesothelin ($\text{Mesothelin}_{35\text{-}622}$) was cloned in-frame as a MfeI-EagI fragment. The entire expression cassette was inserted at the $\text{tRNA}^{Arg}$ locus of the LADD platform strain (Lm11, also referred to as Lm ΔactA ΔinlB) as described in Lauer, P. et al., Construction, Characterization and Use of Two *Listeria monocytogenes* site-specific phage integration vectors. J. Bacteriology (2002) 184(15): 4177-4186), herein incorporated by reference, and vector backbone sequences were removed.

A schematic of ADU-214 and CRS-207 are illustrated in FIG. 1A and FIG. 1B, respectively.

Western Blots from Broth Culture Grown Cell and Intracellular Infections

For broth culture grown Western blots, *Listeria* strains were grown in yeast media to an OD600 of 2.0. Bacteria were removed by centrifugation, and supernatants were TCA precipitated on ice. Supernatants were centrifuged, pellets were acetone washed and resuspended in reducing LDS buffer (Invitrogen). Samples were heated to 95° C. for 10 minutes, and equivalent amounts were run on 4-12% polyacrylamide gels and transferred to nitrocellulose membranes for Western blot analysis. Blots were probed with a polyclonal antibody raised against the mature N-terminus of the ActA protein. Detection was visualized and quantified with a Licor Odyssey IR detection system.

For intracellular Western blots, DC2.4 cells were inoculated with each Lm strain at a multiplicity of infection (MOI) of 10 for 1 hour, and the cells were washed 3 times with PBS and DMEM media supplemented with 50 µg/mL gentamycin. Cells were harvested at 7 hours post infection. Cells were lysed with SDS sample buffer, collected and run on 4-12% polyacrylamide gels and transferred to nitrocellulose membranes for Western blot analysis. Intracellular Western blots utilized a polyclonal antibody raised against the mature N-terminus of the ActA protein and were normalized to p60 expression (an unrelated Lm protein) with an anti-p60 monoclonal antibody. Antigen detection was visualized and quantitated with the Licor Odyssey IR detection system.

Antigen-Specific Immune Responses in Vaccinated Mice

For mesothelin-specific immunogenicity, Balb/c mice (n=5) were vaccinated with $2\times10^6$ cfu ADU-214 intravenously (IV). After seven days, spleens were harvested and immune responses measured by IFNγ ELIspot assay using an overlapping peptide library for mesothelin (153 15mer peptides overlapping by 11 amino acids) or unstimulated media control. For EGFRvIII-specific immunogenicity, C3H/HeN mice (n=4) were vaccinated with $5\times10^6$ cfu ADU-214 IV. After seven days, spleens were harvested and immune responses measured by IFNγ ELIspot assay using the $\text{EGFRvIII}_{26\text{-}33}$—the $K^k$ binding peptide SEQ ID NO: 9 EEKKGNYV.

Protective Immunity to a Wild-Type *Listeria* Challenge

Balb/c mice were vaccinated once with $2\times10^6$ cfu of each Lm strain IV. Forty days later, mice were challenged IV with $5\times10^4$ cfu (2 times $LD_{50}$ dose) of the wild type (WT) Lm strain DP-L4056 (described in Lauer, P. et al., Construction, Characterization and Use of Two *Listeria monocytogenes* site-specific phage integration vectors. J. Bacteriology (2002) 184(15): 4177-4186), herein incorporated by reference,). Three days later, spleens were harvested and homogenized. Dilutions were plated on BHI plates containing 200 µg/mL streptomycin to determine cfu/organ. The limit of detection (LOD) in this assay is 50 CFU.

Tumor Studies

CT26 tumor cells were transfected with a DNA plasmid expressing human mesothelin to produce the stable cell line CT26-hMeso clone 3. Immediately before implantation, an aliquot of frozen tumor cells were thawed and grown to confluency in T cell media. When confluent, cells were harvested and resuspended in HBSS to a concentration of $1\times10^6$ cells/mL for implantation of $2\times10^5$ cells/200 µL dose/mouse. On day 0, Balb/c mice (10 mice per group) were implanted intravenously (IV) with $2\times10^5$ CT26-hMeso cells. On day 3 post-tumor implantation, mice were given by IV: HBSS; $5\times10^6$ cfu, $1\times10^5$ cfu, or $5\times10^3$ cfu of ADU-214; or $5\times10^6$ cfu Lm11 (empty platform strain). Mice were monitored for survival.

Treatment of Cancer

A first in human (FiH), Phase 1, open-label, multicenter study, 2-part study is conducted to evaluate the safety, establish the recommended Phase 2 dose (RP2D), and determine the preliminary clinical efficacy and immunological response of a single agent, ADU-214, in subjects with advanced (Stage Mb) or metastatic (Stage IV) NSCLC (adenocarcinoma) who have failed standard therapy and are progressing at screening. Treatment is administered until confirmed radiographic disease progression, unacceptable toxicity, withdrawal of consent, the investigator decides to stop treatment, the start of subsequent anticancer therapy, or the sponsor ends the study.

Part 1 (Dose Escalation):

is designed to determine the RP2D based on safety and pharmacodynamic assessments. Two doses of ADU-214 (Dose Cohort 1-A: $1\times10^8$ colony forming units (CFU) and Dose Cohort 1-B: $1\times10^9$ CFU) are administered sequentially, applying a modified Toxicity Probability Interval (mTPI) design. After the last subject in each dose cohort has completed treatment in the DLT observation period, the Study Evaluation Team (SET) evaluates all safety data and makes a decision whether to escalate, stay at the current dose, or de-escalate the dose cohort with the second group of subjects treated.

Part 2 (Dose Expansion):

Part 2 is designed to evaluate two expansion cohorts after the RP2D for ADU-214 is determined. Approximately 30 subjects (Cohort 2-A [n=20] and Cohort 2B [n=10]) are enrolled and treated at the RP2D in Part 2. Archived tumor material for a centralized immunohistochemical assessment of mesothelin is available for all subjects in Part 2. Only subjects with tumors that overexpress mesothelin and who have primary tumor or metastatic lesion(s) amenable to tumor core biopsies are enrolled into Cohort 2B. Subjects in Cohort 2B agree to pre- and posttreatment biopsies. Although optional for Cohorts 1A and 1B, and Cohort 2A, pre- and posttreatment biopsies of metastatic lesion(s) are strongly desired to further understand the molecular activity of the study drug. The biopsy procedure is performed using CT or PET CT imaging.

ADU-214 is administered intravenously once every 21 days during the open-label Treatment Period. ADU-214 is administered intravenously over a 1-hour period with the option to increase the duration of the infusion, if necessary. Treatment is administered until confirmed radiographic disease progression, unacceptable toxicity, withdrawal of consent, the investigator decides to stop treatment, the start of subsequent anticancer therapy, or the sponsor ends the study. Safety and efficacy is evaluated.

Study Population—Subjects who are >18 years of age with histologically or cytologically documented NSCLC adenocarcinoma; Stage III b or IV disease; documented tumor progression based on computed tomography (CT) imaging; at least 1 measureable site of disease (Part 2 only) and Eastern Cooperative Oncology Group (ECOG) Performance status score of 0 or 1 are enrolled in this study for Part 1 and Part 2 combined. Subjects must have received at least 2 prior lines of United States Food and Drug Administration (FDA)-approved systemic therapy, of which one therapy has to be a platinum-containing regimen (exception: subjects who refused a second-line regimen after first-line platinum-containing chemotherapy).

Efficacy evaluations—Efficacy assessments are evaluated by the investigator according to the Response Evaluation Criteria in Solid Tumors (V1.1; Eur. J. Cancer 45: 228, 2009) and Immune-Related Response Criteria (Clin. Cancer Res. 15:7412, 2009). Disease response is assessed using CT scans with IV contrast of the neck, chest, abdomen, and pelvis. Subjects who are intolerant of IV CT contrast agents have CT scans performed with oral contrast. Magnetic resonance imaging (MM) may be used to evaluate sites of disease that cannot be adequately imaged using CT. Brain Mill is required only if clinically indicated. All efficacy evaluations, including other sites of disease by radiologic imaging, physical examination, or other procedures as necessary, are performed at the site. These assessments are performed throughout the study at each time point using the same method of assessment used to assess disease at baseline. Data also is collected on subsequent anti-cancer therapies and overall survival in the Posttreatment Follow-up Period.

Results

Expression of ADU-214 in Broth Culture.

Figure 2:
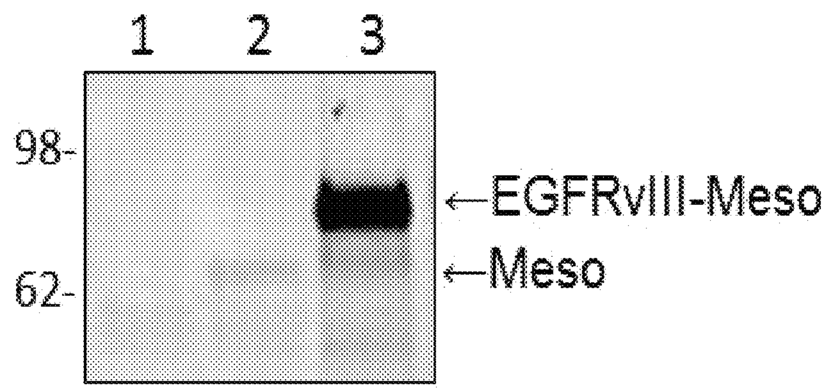
FIG. 2 illustrates the expression of ADU-214 in broth culture. EGFRvIII-Meso=ADU-214 fusion protein; Meso=CRS-207 fusion protein. Lm11 was used as a negative control.

As illustrated in FIG. 2, fusion of EGFRvIII to mesothelin$_{35-622}$ resulted in an increase of approximately 50-fold more protein than CRS-207 in broth culture. The ADU-214 fusion protein is predicted to be approximately 88 kDa (labeled as EGFRvIII-Meso). The CRS-207 protein is predicted to be approximately 72 kDa (labeled as Meso). No band was detected for Lm11, the negative control platform strain.

Expression of ADU-214 in Infected Cells

As illustrated in FIG. 2, fusion of EGFRvIII to mesothelin$_{35-622}$ resulted in an increase of approximately 42-fold more intracellular expression of the protein than CRS-207. The ADU-214 fusion protein is predicted to be approximately 88 kDa. The CRS-207 protein is predicted to be approximately 72 kDa. p60 is a constitutive Lm protein that correlates with bacterial numbers in infected cells and is approximately 60 kDa. The top panel shows the expression of fusion protein detected with the ActA polyclonal antibody. The bottom panel shows p60 expression detected with monoclonal antibody. No band was detected for Lm11, the negative control platform strain.

Antigen-Specific T Cell Immune Responses in Vaccinated Mice

Figure 3:
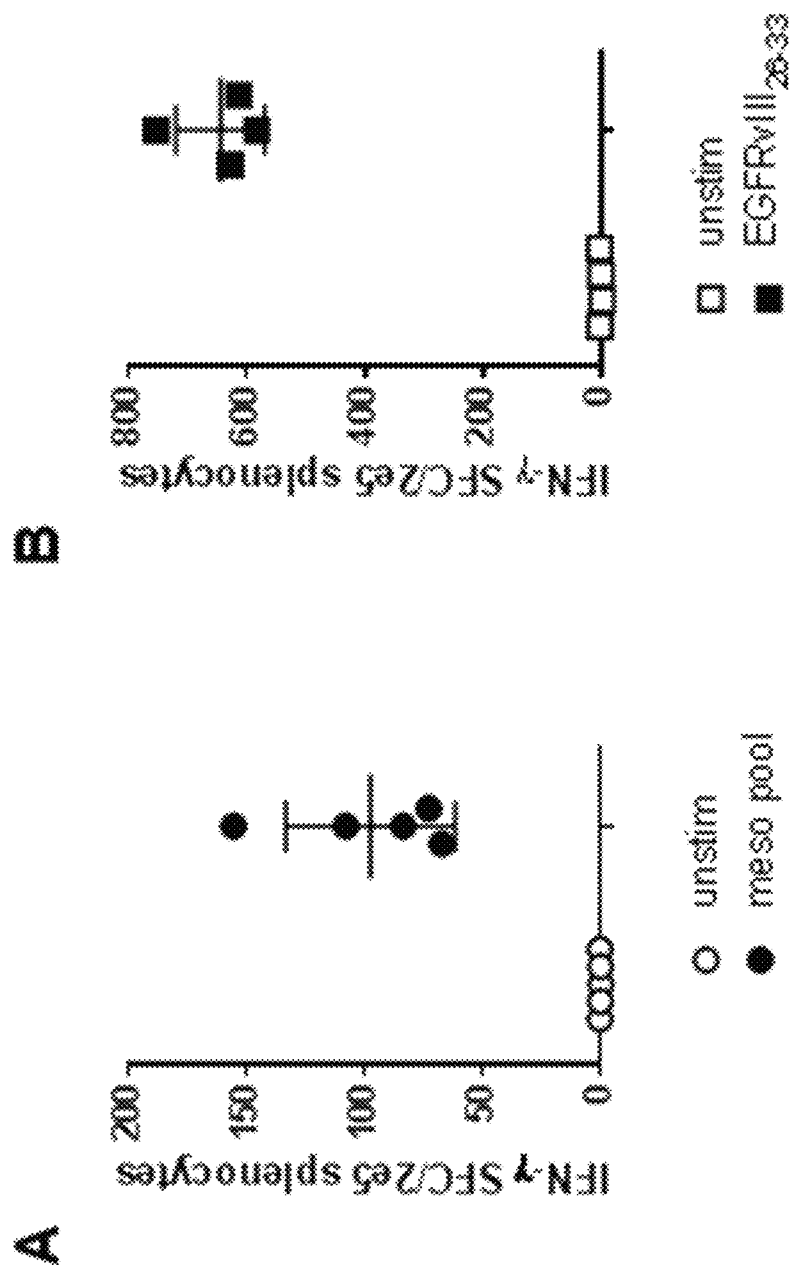
FIG. 3, comprising

ADU-214 induced robust mesothelin-specific T cell mediated immune responses in Balb/c mice (FIG. 4A). ADU-214 induced robust EGFRvIII-specific CD8+ T cell immune responses in C3H/HeN mice (FIG. 3A and FIG. 3B).

Figure 4:
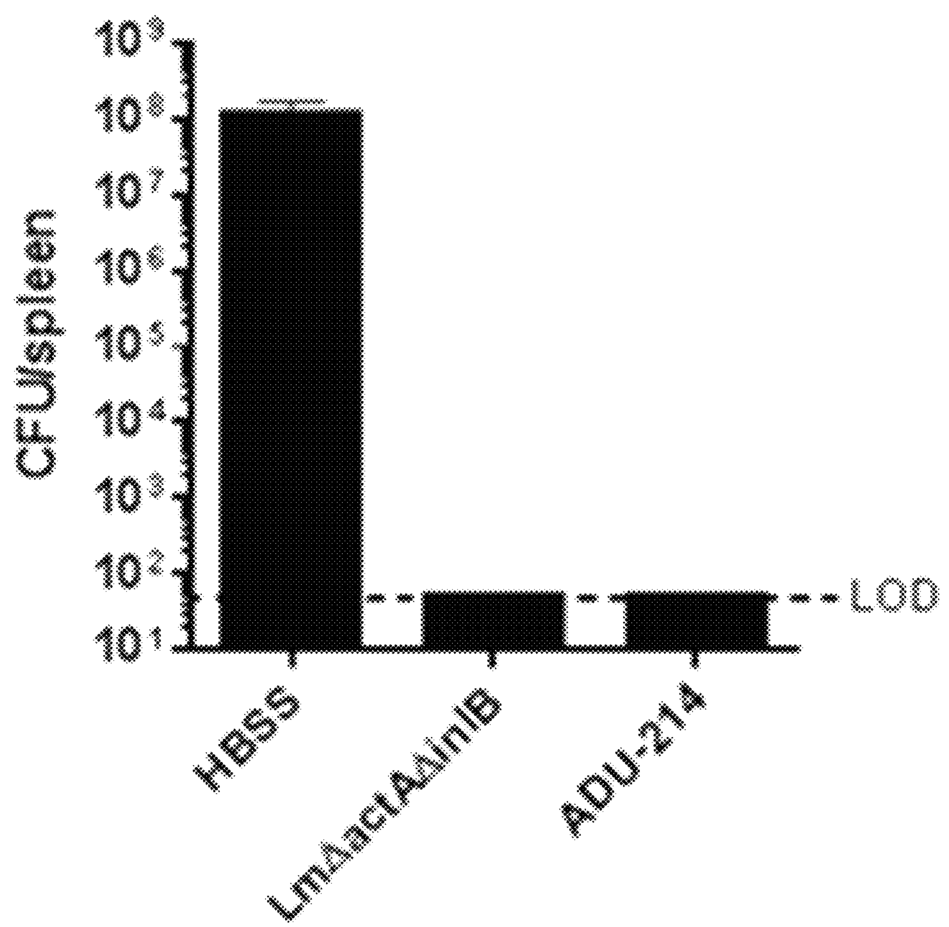
FIG. 4 illustrates the protective immunity of vaccination with ADU-214 against a wild type *Listeria* challenge.

Vaccination with ADU-214 Induces Protective Immunity to a WT *Listeria* Challenge A single vaccination with ADU-214 induced fully protective, long-term immunity to a WT *Listeria* challenge, to comparable levels as the vaccine platform strain Lm11 (FIG. 4). Vaccination with ADU-214 resulted in a greater than 6-log reduction in cfu after WT-Lm challenge. Functional immunity is a combination of magnitude of the antigen-specific immune response and the ability of the immune response to protect from a future challenge. In this case, the functionality was tested with a fully virulent wild-type *Listeria* challenge.

Figure 5:
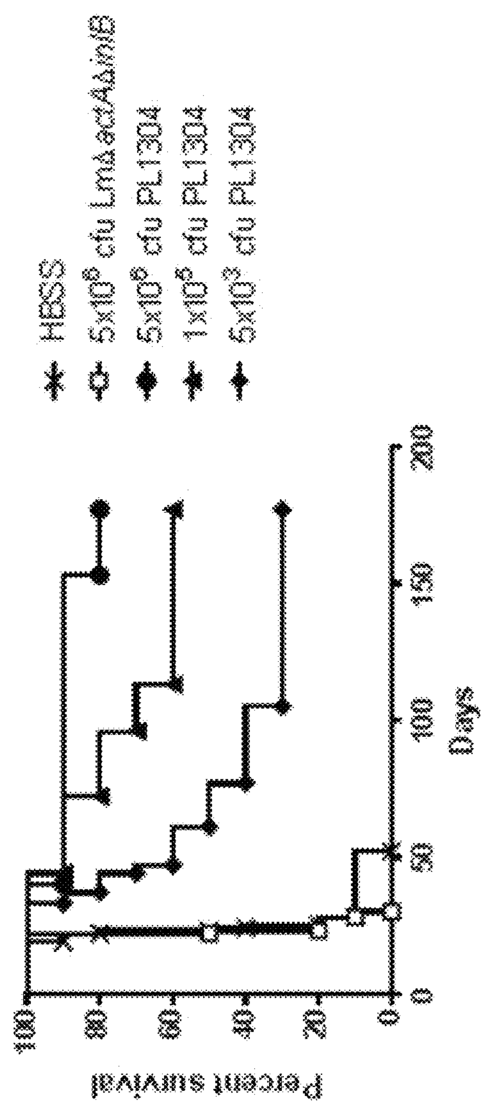
FIG. 5 illustrates a therapeutic vaccination with ADU-214. HBSS and empty platform strain were used as controls.

Therapeutic Vaccination with ADU-214 Results in a Dose-Dependent Anti-Tumor Response In a therapeutic CT26-hMeso lung metastasis model, the anti-tumor efficacy of ADU-214 was determined in BALB/c mice (FIG. 5). Mice were vaccinated IV with different doses of ADU-214, the empty Lm ΔactAΔinlB platform strain (ANZ-100) or Hank's balanced salt solution (HBSS). Consistent with the potent immunogenicity of the vaccine, animals that received ADU-214 had improved survival compared to animals that received either ANZ-100 (referred to as Lm11) or HBSS. Prolonged survival following ADU-214 administration was dose dependent with long term survivors of 70% in the group that received the highest dose ($5\times10^6$ CFU), 60% in the intermediate dose ($1\times10^5$ CFU), and 20% in the lowest dose ($5\times10^3$ CFU).

Those skilled in the art will appreciate that numerous changes and modifications can be made to the preferred embodiments disclosed herein and that such changes and modifications can be made without departing from the spirit of the invention. It is, therefore, intended that the appended claims cover all such equivalent variations as fall within the true spirit and scope of the disclosed compositions and methods.

The disclosures of each patent, patent application, and publication cited or described in this document are hereby incorporated herein by reference, in its entirety.

actAp-ActAN100*-EGFRvIIIx5-mesothelin$_{35-622}$ nucleotide sequence (SEQ ID NO: 1)

gggaagcagttggggttaactgattaacaaatgttagagaaaaattaattctccaagtgatat tcttaaaataattcatgaatatttttttcttatattagctaattaagaagataattaactgctaat ccaatttttaacggaataaattagtgaaaatgaaggccgaattttccttgttctaaaaaggttgtatta gcgtatcacgaggagggagtataaGTGGGATTAAATAGATTTATGCGTGCGATGATGGTAGTTTTC

ATTACTGCCAACTGCATTACGATTAACCCCGACATAATATTTGCAGCGACAGATAGC

GAAGATTCCAGTCTAAACACAGATGAATGGGAAGAAGAATACGAAACTGCACGTGA

AGTAAGTTCACGTGATATTGAGGAACTAGAAAAATCGAATAAAGTGAAAAATACGA

ACAAAGCAGACCAAGATAATAAACGTAAAGCAAAAGCAGAGAAAGGTggatcc*GCAA*

*GCAAAGTATTGCCAGCTAGTCGTGCATTAGAGGAGAAAAAGGGGAATTACGTGGTGACGG*

*ATCATGGATCGTGTGCCGATGGCTCAGTAAAGACTAGTGCGAGCAAAGTGGCCCCTGCAT*

*CACGAGCACTTGAAGAGAAAAAAGGAAACTATGTTGTGACCGATCATGGTAGCTGCGGAG*

*ATGGTTCAATTAAATTATCAAAAGTCTTACCAGCATCTAGAGCTTTAGAGGAAAAGAAGGGT*

*AACTATGTCGTAACAGATCATGGAAGTTGTGCTGACGGAAGTGTTAAAGCGTCGAAAGTAG*

*CTCCAGCTTCTCGCGCATTAGAAGAAAAGAAAGGCAATTATGTTGTAACAGACCATGGTAG*

*TTGTGGTGATGGCTCGATCAAATTGTCAAAAGTTCTACCGGCTTCTCGTGCGCTAGAAGAG*

*AAGAAAGGAAATTACGTAGTTACAGACCACGGCTCTTGCGCGGATGGTTCCGTTAAA*caattg

CGTACATTAGCAGGTGAAACAGGTCAAGAAGCAGCACCACTTGACGGTGTATT

AACGAATCCACCAAATATATCAAGTTTAAGTCCACGTCAATTATTAGGTTTTCC

ATGTGCAGAAGTTTCAGGTTTAAGTACAGAACGTGTCCGTGAGTTAGCAGTTG

CATTAGCACAAAAAAACGTTAAATTATCTACAGAACAGTTACGTTGTTTAGCCC

ATAGATTAAGCGAACCACCAGAAGACTTAGATGCACTTCCTTTAGACCTTCTTT

TATTCTTAAATCCAGATGCATTTTCAGGACCACAAGCATGTACACGTTTTTTTA

GTCGAATTACAAAAGCCAATGTTGATTTATTACCTCGTGGGGCTCCTGAAAGAC

AACGTTTATTACCTGCTGCATTAGCATGCTGGGGTGTTCGCGGTAGCTTATTAA

GTGAAGCCGATGTTCGTGCTTTAGGGGGTTTAGCATGTGATTTACCTGGTCGTT

TCGTTGCAGAATCAGCAGAAGTGTTATTACCGAGATTAGTTTCATGCCCAGGAC

CTTTAGATCAAGATCAACAAGAGGCAGCTAGAGCAGCTCTTCAAGGAGGAGGC

CCACCATATGGCCCACCAAGTACATGGAGTGTTTCTACAATGGATGCGTTAAGA

GGTTTATTACCGGTTTTAGGACAACCAATTATTCGTAGTATTCCACAAGGCATT

GTAGCAGCATGGCGTCAACGTAGTTCTCGTGATCCGTCTTGGCGACAACCAGA

ACGTACAATTCTACGTCCAAGATTTCGTAGAGAAGTAGAAAAAACGGCGTGTC

CTAGTGGCAAAAAAGCACGTGAAATTGATGAAAGTTTAATTTTTTATAAAAAAT

GGGAATTAGAAGCATGTGTCGATGCAGCATTACTAGCTACACAAATGGATCGT

GTTAATGCTATTCCATTCACATATGAACAATTAGATGTTTTAAAGCATAAATTA

GACGAATTATATCCACAAGGTTATCCAGAATCAGTTATTCAACATTTAGGTTAC

TTATTTTTAAAAATGAGTCCAGAAGACATACGCAAATGGAATGTTACAAGTTTA

GAAACATTAAAAGCGCTTTTAGAAGTTAACAAAGGTCATGAAATGAGTCCACAA

GTTGCTACGTTAATTGATAGATTCGTTAAAGGCCGTGGTCAATTAGATAAAGAT

ACTTTAGATACATTAACAGCATTTTATCCTGGCTACTTATGCAGTTTATCACCA

GAAGAATTAAGTTCCGTTCCACCGAGTAGTATCTGGGCAGTTCGTCCGCAAGA

-continued

TTTAGATACATGCGACCCACGTCAATTAGATGTTTTATATCCAAAAGCAAGATT

AGCTTTCCAAAATATGAACGGTAGTGAATATTTCGTAAAAATTCAATCCTTTTT

AGGTGGTGCACCAACTGAAGATCTAAAAGCATTAAGCCAACAAAATGTAAGTA

TGGATTTAGCTACGTTTATGAAATTACGTACAGATGCAGTTCTACCATTAACAG

TTGCAGAAGTTCAAAAATTATTAGGTCCACACGTAGAAGGATTAAAAGCAGAA

GAACGTCACCGTCCAGTTCGCGATTGGATTTTACGTCAACGTCAAGATGATTTA

GATACATTAGGTTTAGGTTTACAAGGCGGTATTCCGAATGGATATTTAGTGTTA

GATTTATCGGTTCAAGAAGCATTAAGTGGTACACCGTGTTTATTAGGTCCAGGT

CCAGTTTTAACAGTGTTAGCATTATTATTAGCCAGTACATTAGCTtaa actA promoter nucleotide sequence (SEQ ID NO: 2)

gggaagcagttggggttaactgattaacaaatgttagagaaaaattaattctccaagtgatattct taaaataattcatgaatatttttttcttatattagctaattaagaagataattaactgctaatccaa tttttaacggaataaattagtgaaaatgaaggccgaattttccttgttctaaaaaggttgtattagc gtatcacgaggagggagtataa ActAN100* nucleotide sequence (SEQ ID NO: 3)

GTGGGATTAAATAGATTTATGCGTGCGATGATGGTAGTTTTCATTACTGCCAACTGC

ATTACGATTAACCCCGACATAATATTTGCAGCGACAGATAGCGAAGATTCCAGTCTA

AACACAGATGAATGGGAAGAAGAATACGAAACTGCACGTGAAGTAAGTTCACGTGA

TATTGAGGAACTAGAAAAATCGAATAAAGTGAAAAATACGAACAAAGCAGACCAA

GATAATAAACGTAAAGCAAAAGCAGAGAAAGGT

EGFRvIII nucleotide sequence (SEQ ID NO: 4)

CCdGCwwswmGhGCdyTwGArGArAArAArGGnAAyTAyGTnGTdACvGAyCAyGGhwsbTGy

EGFRvIIIx5 nucleotide sequence (SEQ ID NO: 5)

*GCAAGCAAAGTATTGCCAGCTAGTCGTGCATTAGAGGAGAAAAAGGGGAATTACGTGGTG*

*ACGGATCATGGATCGTGTGCCGATGGCTCAGTAAAGACTAGTGCGAGCAAAGTGGCCCCT*

*GCATCACGAGCACTTGAAGAGAAAAAAGGAAACTATGTTGTGACCGATCATGGTAGCTGC*

*GGAGATGGTTCAATTAAATTATCAAAAGTCTTACCAGCATCTAGAGCTTTAGAGGAAAAGAA*

*GGGTAACTATGTCGTAACAGATCATGGAAGTTGTGCTGACGGAAGTGTTAAAGCGTCGAA*

*AGTAGCTCCAGCTTCTCGCGCATTAGAAGAAAAGAAAGGCAATTATGTTGTAACAGACCAT*

*GGTAGTTGTGGTGATGGCTCGATCAAATTGTCAAAAGTTCTACCGGCTTCTCGTGCGCTAG*

*AAGAGAAGAAAGGAAATTACGTAGTTACAGACCACGGCTCTTGCGCGGATGGTTCCGTTA*

*AA*

Mesothelin$_{35-622}$ nucleotide sequence (SEQ ID NO: 6)

CGTACATTAGCAGGTGAAACAGGTCAAGAAGCAGCACCACTTGACGGTGTATT

AACGAATCCACCAAATATATCAAGTTTAAGTCCACGTCAATTATTAGGTTTTCC

ATGTGCAGAAGTTTCAGGTTTAAGTACAGAACGTGTCCGTGAGTTAGCAGTTG

CATTAGCACAAAAAAACGTTAAATTATCTACAGAACAGTTACGTTGTTTAGCCC

ATAGATTAAGCGAACCACCAGAAGACTTAGATGCACTTCCTTTAGACCTTCTTT

TATTCTTAAATCCAGATGCATTTTCAGGACCACAAGCATGTACACGTTTTTTTA

GTCGAATTACAAAAGCCAATGTTGATTTATTACCTCGTGGGGCTCCTGAAAGAC

-continued

AACGTTTATTACCTGCTGCATTAGCATGCTGGGGTGTTCGCGGTAGCTTATTAA

GTGAAGCCGATGTTCGTGCTTTAGGGGGTTTAGCATGTGATTTACCTGGTCGTT

TCGTTGCAGAATCAGCAGAAGTGTTATTACCGAGATTAGTTTCATGCCCAGGAC

CTTTAGATCAAGATCAACAAGAGGCAGCTAGAGCAGCTCTTCAAGGAGGAGGC

CCACCATATGGCCCACCAAGTACATGGAGTGTTTCTACAATGGATGCGTTAAGA

GGTTTATTACCGGTTTTAGGACAACCAATTATTCGTAGTATTCCACAAGGCATT

GTAGCAGCATGGCGTCAACGTAGTTCTCGTGATCCGTCTTGGCGACAACCAGA

ACGTACAATTCTACGTCCAAGATTTCGTAGAGAAGTAGAAAAAACGGCGTGTC

CTAGTGGCAAAAAAGCACGTGAAATTGATGAAAGTTTAATTTTTTATAAAAAAT

GGGAATTAGAAGCATGTGTCGATGCAGCATTACTAGCTACACAAATGGATCGT

GTTAATGCTATTCCATTCACATATGAACAATTAGATGTTTTAAAGCATAAATTA

GACGAATTATATCCACAAGGTTATCCAGAATCAGTTATTCAACATTTAGGTTAC

TTATTTTTAAAAATGAGTCCAGAAGACATACGCAAATGGAATGTTACAAGTTTA

GAAACATTAAAAGCGCTTTTAGAAGTTAACAAAGGTCATGAAATGAGTCCACAA

GTTGCTACGTTAATTGATAGATTCGTTAAAGGCCGTGGTCAATTAGATAAAGAT

ACTTTAGATACATTAACAGCATTTTATCCTGGCTACTTATGCAGTTTATCACCA

GAAGAATTAAGTTCCGTTCCACCGAGTAGTATCTGGGCAGTTCGTCCGCAAGA

TTTAGATACATGCGACCCACGTCAATTAGATGTTTTATATCCAAAAGCAAGATT

AGCTTTCCAAAATATGAACGGTAGTGAATATTTCGTAAAAATTCAATCCTTTTT

AGGTGGTGCACCAACTGAAGATCTAAAAGCATTAAGCCAACAAAATGTAAGTA

TGGATTTAGCTACGTTTATGAAATTACGTACAGATGCAGTTCTACCATTAACAG

TTGCAGAAGTTCAAAAATTATTAGGTCCACACGTAGAAGGATTAAAAGCAGAA

GAACGTCACCGTCCAGTTCGCGATTGGATTTTACGTCAACGTCAAGATGATTTA

GATACATTAGGTTTAGGTTTACAAGGCGGTATTCCGAATGGATATTTAGTGTTA

GATTTATCGGTTCAAGAAGCATTAAGTGGTACACCGTGTTTATTAGGTCCAGGT

CCAGTTTTAACAGTGTTAGCATTATTATTAGCCAGTACATTAGCT

EGFRvIIIx5-Mesothelin$_{35-622}$ nucleotide sequence (SEQ ID NO: 7)

*GCAAGCAAAGTATTGCCAGCTAGTCGTGCATTAGAGGAGAAAAAGGGGAATTACGTGGTG*

*ACGGATCATGGATCGTGTGCCGATGGCTCAGTAAAGACTAGTGCGAGCAAAGTGGCCCCT*

*GCATCACGAGCACTTGAAGAGAAAAAGGAAACTATGTTGTGACCGATCATGGTAGCTGC*

*GGAGATGGTTCAATTAAATTATCAAAAGTCTTACCAGCATCTAGAGCTTTAGAGGAAAAGAA*

*GGGTAACTATGTCGTAACAGATCATGGAAGTTGTGCTGACGGAAGTGTTAAAGCGTCGAA*

*AGTAGCTCCAGCTTCTCGCGCATTAGAAGAAAAGAAAGGCAATTATGTTGTAACAGACCAT*

*GGTAGTTGTGGTGATGGCTCGATCAAATTGTCAAAAGTTCTACCGGCTTCTCGTGCGCTAG*

*AAGAGAAGAAAGGAAATTACGTAGTTACAGACCACGGCTCTTGCGCGGATGGTTCCGTTA*

*AA*caattgCGTACATTAGCAGGTGAAACAGGTCAAGAAGCAGCACCACTTGACGGT

GTATTAACGAATCCACCAAATATATCAAGTTTAAGTCCACGTCAATTATTAGGT

TTTCCATGTGCAGAAGTTTCAGGTTTAAGTACAGAACGTGTCCGTGAGTTAGCA

GTTGCATTAGCACAAAAAAACGTTAAATTATCTACAGAACAGTTACGTTGTTTA

GCCCATAGATTAAGCGAACCACCAGAAGACTTAGATGCACTTCCTTTAGACCTT

CTTTTATTCTTAAATCCAGATGCATTTTCAGGACCACAAGCATGTACACGTTTTT

-continued

TTAGTCGAATTACAAAAGCCAATGTTGATTTATTACCTCGTGGGGCTCCTGAAA

GACAACGTTTATTACCTGCTGCATTAGCATGCTGGGGTGTTCGCGGTAGCTTAT

TAAGTGAAGCCGATGTTCGTGCTTTAGGGGGTTTAGCATGTGATTTACCTGGTC

GTTTCGTTGCAGAATCAGCAGAAGTGTTATTACCGAGATTAGTTTCATGCCCAG

GACCTTTAGATCAAGATCAACAAGAGGCAGCTAGAGCAGCTCTTCAAGGAGGA

GGCCCACCATATGGCCCACCAAGTACATGGAGTGTTTCTACAATGGATGCGTT

AAGAGGTTTATTACCGGTTTTAGGACAACCAATTATTCGTAGTATTCCACAAGG

CATTGTAGCAGCATGGCGTCAACGTAGTTCTCGTGATCCGTCTTGGCGACAAC

CAGAACGTACAATTCTACGTCCAAGATTTCGTAGAGAAGTAGAAAAAACGGCG

TGTCCTAGTGGCAAAAAAGCACGTGAAATTGATGAAAGTTTAATTTTTTATAAA

AAATGGGAATTAGAAGCATGTGTCGATGCAGCATTACTAGCTACACAAATGGA

TCGTGTTAATGCTATTCCATTCACATATGAACAATTAGATGTTTTAAAGCATAA

ATTAGACGAATTATATCCACAAGGTTATCCAGAATCAGTTATTCAACATTTAGG

TTACTTATTTTTAAAAATGAGTCCAGAAGACATACGCAAATGGAATGTTACAAG

TTTAGAAACATTAAAAGCGCTTTTAGAAGTTAACAAAGGTCATGAAATGAGTCC

ACAAGTTGCTACGTTAATTGATAGATTCGTTAAAGGCCGTGGTCAATTAGATAA

AGATACTTTAGATACATTAACAGCATTTTATCCTGGCTACTTATGCAGTTTATCA

CCAGAAGAATTAAGTTCCGTTCCACCGAGTAGTATCTGGGCAGTTCGTCCGCA

AGATTTAGATACATGCGACCCACGTCAATTAGATGTTTTATATCCAAAAGCAAG

ATTAGCTTTCCAAAATATGAACGGTAGTGAATATTTCGTAAAAATTCAATCCTT

TTTAGGTGGTGCACCAACTGAAGATCTAAAAGCATTAAGCCAACAAAATGTAAG

TATGGATTTAGCTACGTTTATGAAATTACGTACAGATGCAGTTCTACCATTAAC

AGTTGCAGAAGTTCAAAAATTATTAGGTCCACACGTAGAAGGATTAAAAGCAG

AAGAACGTCACCGTCCAGTTCGCGATTGGATTTTACGTCAACGTCAAGATGATT

TAGATACATTAGGTTTAGGTTTACAAGGCGGTATTCCGAATGGATATTTAGTGT

TAGATTTATCGGTTCAAGAAGCATTAAGTGGTACACCGTGTTTATTAGGTCCAG

GTCCAGTTTTAACAGTGTTAGCATTATTATTAGCCAGTACATTAGCT

ADU-214 fusion protein amino acid sequence (SEQ ID NO: 8)

MGLNRFMRAMMVVFITANCITINPDIIFAATDSEDSSLNTDEWEEEYETAREVSSRDIEEL

EKSNKVKNTNKADQDNKRKAKAEKGGS*ASKVLPASRALEEKKGNYVVTDHGSCADGSVK*

*TISASKVAPASRALEEKKGNYVVTDHGSCGDGSIKLSKVLPASRALEEKKGNYVVTDHGSCADG*

*SVKASKVAPASRALEEKKGNYVVTDHGSCGDGSIKLSKVLPASRALEEKKGNYVVTDHGSCAD*

*GSV*KQLRTLAGETGQEAAPLDGVLTNPPNISSLSPRQLLGFPCAEVSGLSTERVREL

AVALAQKNVKLSTEQLRCLAHRLSEPPEDLDALPLDLLLFLNPDAFSGPQACTRFFS

RITKANVDLLPRGAPERQRLLPAALACWGVRGSLLSEADVRALGGLACDLPGRFV

AESAEVLLPRLVSCPGPLDQDQQEAARAALQGGGPPYGPPSTWSVSTMDALRGLL

PVLGQPIIRSIPQGIVAAWRQRSSRDPSWRQPERTILRPRFRREVEKTACPSGKKAR

EIDESLIFYKKWELEACVDAALLATQMDRVNAIPFTYEQLDVLKHKLDELYPQGYP

ESVIQHLGYLFLKMSPEDIRKVVNVTSLETLKALLEVNKGHEMSPQVATLIDRFVKG

RGQLDKDTLDTLTAFYPGYLCSLSPEELSSVPPSSIWAVRPQDLDTCDPRQLDVLYP

-continued

KARLAFQNMNGSEYFVKIQSFLGGAPTEDLKALSQQNVSMDLATFMKLRTDAVLP

LTVAEVQKLLGPHVEGLKAEERHRPVRDWILRQRQDDLDTLGLGLQGGIPNGYLV

LDLSVQEALSGTPCLLGPGPVLTVLALLLASTLA

EGFRvIII amino acid sequence (SEQ ID NO: 9)

PASRALEEKKGNYVVTDHGSC

EGFRvIIIx5 amino acid sequence (SEQ ID NO: 10)

ASKVLPASRALEEKKGNYVVTDHGSCADGSVKTSASKVAPASRALEEKKGNYVVTDH
GSCGDGSIKLSKVLPASRALEEKKGNYVVTDHGSCADGSVKASKVAPASRALEEKKGN
YVVTDHGSCGDGSIKLSKVLPASRALEEKKGNYVVTDHGSCADGSVK

Mesothelin$_{35\text{-}622}$ amino acid sequence (SEQ ID NO: 11)

RTLAGETGQEAAPLDGVLTNPPNISSLSPRQLLGFPCAEVSGLSTERVRELAVALAQ

KNVKLSTEQLRCLAHRLSEPPEDLDALPLDLLLFLNPDAFSGPQACTRFFSRITKAN

VDLLPRGAPERQRLLPAALACWGVRGSLLSEADVRALGGLACDLPGRFVAESAEV

LLPRLVSCPGPLDQDQQEAARAALQGGGPPYGPPSTWSVSTMDALRGLLPVLGQPI

IRSIPQGIVAAWRQRSSRDPSWRQPERTILRPRFRREVEKTACPSGKKAREIDESLIF

YKKVVELEACVDAALLATQMDRVNAIPFTYEQLDVLKHKLDELYPQGYPESVIQHL

GYLFLKMSPEDIRKVVNVTSLETLKALLEVNKGHEMSPQVATLIDRFVKGRGQLDK

DTLDTLTAFYPGYLCSLSPEELSSVPPSSIWAVRPQDLDTCDPRQLDVLYPKARLAF

QNMNGSEYFVKIQSFLGGAPTEDLKALSQQNVSMDLATFMKLRTDAVLPLTVAEV

QKLLGPHVEGLKAEERHRPVRDWILRQRQDDLDTLGLGLQGGIPNGYLVLDLSVQ

EALSGTPCLLGPGPVLTVLALLLASTLA

ActAN100* amino acid sequence
(BamHI linker gs = underlined)

(SEQ ID NO: 12)

MGLNRFMRAMMVVFITANCITINPDIIFAATDSEDSSLNTDEWEEEYETAREVSSRDIEEL
EKSNKVKNTNKADQDNKRKAKAEKG<u>GS</u>

EGFRvIII nucleotide sequence 1

(SEQ ID NO: 13)

CCAGCTAGTCGTGCATTAGAGGAGAAAAAGGGGAATTACGTGGTGACGGATCATGG
ATCGTGT

EGFRvIII nucleotide sequence 2

(SEQ ID NO: 14)

CCTGCATCACGAGCACTTGAAGAGAAAAAAGGAAACTATGTTGTGACCGATCATGG
TAGCTGC

EGFRvIII nucleotide sequence 3

(SEQ ID NO: 15)

CCAGCATCTAGAGCTTTAGAGGAAAAGAAGGGTAACTATGTCGTAACAGATCATGG
AAGTTGT

EGFRvIII nucleotide sequence 4

(SEQ ID NO: 16)

CCAGCTTCTCGCGCATTAGAAGAAAAGAAAGGCAATTATGTTGTAACAGACCATGG
TAGTTGT

EGFRvIII nucleotide sequence 5

(SEQ ID NO: 17)

CCGGCTTCTCGTGCGCTAGAAGAGAAGAAAGGAAATTACGTAGTTACAGACCACGG
CTCTTGC hly promoter nucleotide sequence (SEQ ID NO: 18)

tcctttgattagtatattcctatcttaaagttacttttatgtggaggcattaacatttgttaatgac gtcaaaaggatagcaagactagaataaagctataaagcaagcatataatattgcgtttcatctttag aagcgaatttcgccaatattataattatcaaaagagaggggtggcaaacggtatttggcattattagg ttaaaaaatgtagaaggagagtgaaaccc -continued LLO441 nucleotide sequence (SEQ ID NO: 19)

ATGAAAAAAATAATGCTAGTTTTTATTACACTTATATTAGTTAGTCTACCAATTGCGC

AACAAACTGAAGCAAAGGATGCATCTGCATTCAATAAAGAAAATTCAATTTCATCC

ATGGCACCACCAGCATCTCCGCCTGCAAGTCCTAAGACGCCAATCGAAAAGAAACA

CGCGGATGAAATCGATAAGTATATACAAGGATTGGATTACAATAAAAACAATGTAT

TAGTATACCACGGAGATGCAGTGACAAATGTGCCGCCAAGAAAAGGTTACAAAGAT

GGAAATGAATATATTGTTGTGGAGAAAAAGAAGAAATCCATCAATCAAAATAATGC

AGACATTCAAGTTGTGAATGCAATTTCGAGCCTAACCTATCCAGGTGCTCTCGTAAA

AGCGAATTCGGAATTAGTAGAAAATCAACCAGATGTTCTCCCTGTAAAACGTGATTC

ATTAACACTCAGCATTGATTTGCCAGGTATGACTAATCAAGACAATAAAATAGTTGT

AAAAAATGCCACTAAATCAAACGTTAACAACGCAGTAAATACATTAGTGGAAAGAT

GGAATGAAAAATATGCTCAAGCTTATCCAAATGTAAGTGCAAAAATTGATTATGAT

GACGAAATGGCTTACAGTGAATCACAATTAATTGCGAAATTTGGTACAGCATTTAAA

GCTGTAAATAATAGCTTGAATGTAAACTTCGGCGCAATCAGTGAAGGGAAAATGCA

AGAAGAAGTCATTAGTTTTAAACAAATTTACTATAACGTGAATGTTAATGAACCTAC

AAGACCTTCCAGATTTTTCGGCAAAGCTGTTACTAAAGAGCAGTTGCAAGCGCTTGG

AGTGAATGCAGAAAATCCTCCTGCATATATCTCAAGTGTGGCGTATGGCCGTCAAGT

TTATTTGAAATTATCAACTAATTCCCATAGTACTAAAGTAAAAGCTGCTTTTGATGCT

GCCGTAAGCGGAAAATCTGTCTCAGGTGATGTAGAACTAACAAATATCATCAAAAA

TTCTTCCTTCAAAGCCGTAATTTACGGAGGTTCCGCAAAAGATGAAGTTCAAATCAT

CGACGGCAACCTCGGAGACTTACGCGATATTTTGAAAAAAGGCGCTACTTTTAATCG

AGAAACACCAGGAGTTCCCATTGCTTATACAACAAACTTCCTAAAAGACAATGAATT

AGCTGTTATTAAAAACAACTCAGAATATATTGAAACAACTTCAAAAGCTTATACAGA

TGGAAAAATTAACATCGATCACTCTGGAGGATACGTTGCTCAATTCAACATTTCTTG

GGATGAAGTAAATTATGAT

LLO441 amino acid sequence (SEQ ID NO: 20)

MKKIMLVFITLILVSLPIAQQTEAKDASAFNKENSISSMAPPASPPASPKTPIEKKHADEID

KYIQGLDYNKNNVLVYHGDAVTNVPPRKGYKDGNEYIVVEKKKKSINQNNADIQVVN

AISSLTYPGALVKANSELVENQPDVLPVKRDSLTLSIDLPGMTNQDNKIVVKNATKSNV

NNAVNTLVERWNEKYAQAYPNVSAKIDYDDEMAYSESQLIAKFGTAFKAVNNSLNVN

FGAISEGKMQEEVISFKQIYYNVNVNEPTRPSRFFGKAVTKEQLQALGVNAENPPAYISS

VAYGRQVYLKL STNSHSTKVKAAFDAAVSGKSVSGDVELTNIIKNSSFKAVIYGGSAKD

EVQIIDGNLGDLRDILKKGATFNRETPGVPIAYTTNFLKDNELAVIKNNSEYIETTSKAYT

DGKINIDHSGGYVAQFNISWDEVNYD

LLO441 ΔPEST nucleotide sequence (SEQ ID NO: 21)

ATGAAAAAAATAATGCTAGTTTTTATTACACTTATATTAGTTAGTCTACCAATTGCGC

AACAAACTGAAGCAAAGGATGCATCTGCATTCAATACGCCAATCGAAAAGAAACAC

GCGGATGAAATCGATAAGTATATACAAGGATTGGATTACAATAAAAACAATGTATT

AGTATACCACGGAGATGCAGTGACAAATGTGCCGCCAAGAAAAGGTTACAAAGATG

GAAATGAATATATTGTTGTGGAGAAAAAGAAGAAATCCATCAATCAAAATAATGCA

GACATTCAAGTTGTGAATGCAATTTCGAGCCTAACCTATCCAGGTGCTCTCGTAAAA

-continued

GCGAATTCGGAATTAGTAGAAAATCAACCAGATGTTCTCCCTGTAAAACGTGATTCA

TTAACACTCAGCATTGATTTGCCAGGTATGACTAATCAAGACAATAAAATAGTTGTA

AAAAATGCCACTAAATCAAACGTTAACAACGCAGTAAATACATTAGTGGAAAGATG

GAATGAAAAATATGCTCAAGCTTATCCAAATGTAAGTGCAAAAATTGATTATGATG

ACGAAATGGCTTACAGTGAATCACAATTAATTGCGAAATTTGGTACAGCATTTAAAG

CTGTAAATAATAGCTTGAATGTAAACTTCGGCGCAATCAGTGAAGGGAAAATGCAA

GAAGAAGTCATTAGTTTTAAACAAATTTACTATAACGTGAATGTTAATGAACCTACA

AGACCTTCCAGATTTTTCGGCAAAGCTGTTACTAAAGAGCAGTTGCAAGCGCTTGGA

GTGAATGCAGAAAATCCTCCTGCATATATCTCAAGTGTGGCGTATGGCCGTCAAGTT

TATTTGAAATTATCAACTAATTCCCATAGTACTAAAGTAAAAGCTGCTTTTGATGCT

GCCGTAAGCGGAAAATCTGTCTCAGGTGATGTAGAACTAACAAATATCATCAAAAA

TTCTTCCTTCAAAGCCGTAATTTACGGAGGTTCCGCAAAAGATGAAGTTCAAATCAT

CGACGGCAACCTCGGAGACTTACGCGATATTTTGAAAAAAGGCGCTACTTTTAATCG

AGAAACACCAGGAGTTCCCATTGCTTATACAACAAACTTCCTAAAAGACAATGAATT

AGCTGTTATTAAAAACAACTCAGAATATATTGAAACAACTTCAAAAGCTTATACAGA

TGGAAAAATTAACATCGATCACTCTGGAGGATACGTTGCTCAATTCAACATTTCTTG

GGATGAAGTAAATTATGAT

LLO441 ΔPEST amino acid sequence (SEQ ID NO: 22)

MKKIMLVFITLILVSLPIAQQTEAKDASAFNTPIEKKHADEIDKYIQGLDYNKNNVLVYH

GDAVTNVPPRKGYKDGNEYIVVEKKKKSINQNNADIQVVNAISSLTYPGALVKANSELV

ENQPDVLPVKRDSLTLSIDLPGMTNQDNKIVVKNATKSNVNNAVNTLVERWNEKYAQ

AYPNVSAKIDYDDEMAYSESQLIAKFGTAFKAVNNSLNVNFGAISEGKMQEEVISFKQI

YYNVNVNEPTRPSRFFGKAVTKEQLQALGVNAENPPAYISSAYGRQVYLKLSTNSHST

KVKAAFDAAVSGKSVSGDVELTNIIKNSSFKAVIYGGSAKDEVQIIDGNLGDLRDILKKG

ATFNRETPGVPIAYTTNFLKDNELAVIKNNSEYIETTSKAYTDGKINIDHSGGYVAQFNIS

WDEVNYD

LLO441 Δ26 nucleotide sequence (SEQ ID NO: 23)

ATGAAAAAAATAATGCTAGTTTTTATTACACTTATATTAGTTAGTCTACCAATTGCGC

AACAAACTGAAGCAAAGGATGCATCTGCATTCAATAAAGAAGAAATCGATAAGTAT

ATACAAGGATTGGATTACAATAAAAACAATGTATTAGTATACCACGGAGATGCAGT

GACAAATGTGCCGCCAAGAAAAGGTTACAAAGATGGAAATGAATATATTGTTGTGG

AGAAAAAGAAGAAATCCATCAATCAAAATAATGCAGACATTCAAGTTGTGAATGCA

ATTTCGAGCCTAACCTATCCAGGTGCTCTCGTAAAAGCGAATTCGGAATTAGTAGAA

AATCAACCAGATGTTCTCCCTGTAAAACGTGATTCATTAACACTCAGCATTGATTTG

CCAGGTATGACTAATCAAGACAATAAAATAGTTGTAAAAAATGCCACTAAATCAAA

CGTTAACAACGCAGTAAATACATTAGTGGAAAGATGGAATGAAAAATATGCTCAAG

CTTATCCAAATGTAAGTGCAAAAATTGATTATGATGACGAAATGGCTTACAGTGAAT

CACAATTAATTGCGAAATTTGGTACAGCATTTAAAGCTGTAAATAATAGCTTGAATG

TAAACTTCGGCGCAATCAGTGAAGGGAAAATGCAAGAAGAAGTCATTAGTTTTAAA

CAAATTTACTATAACGTGAATGTTAATGAACCTACAAGACCTTCCAGATTTTTCGGC

-continued

AAAGCTGTTACTAAAGAGCAGTTGCAAGCGCTTGGAGTGAATGCAGAAAATCCTCC

TGCATATATCTCAAGTGTGGCGTATGGCCGTCAAGTTTATTTGAAATTATCAACTAA

TTCCCATAGTACTAAAGTAAAAGCTGCTTTTGATGCTGCCGTAAGCGGAAAATCTGT

CTCAGGTGATGTAGAACTAACAAATATCATCAAAAATTCTTCCTTCAAAGCCGTAAT

TTACGGAGGTTCCGCAAAAGATGAAGTTCAAATCATCGACGGCAACCTCGGAGACT

TACGCGATATTTTGAAAAAAGGCGCTACTTTTAATCGAGAAACACCAGGAGTTCCCA

TTGCTTATACAACAAACTTCCTAAAAGACAATGAATTAGCTGTTATTAAAAACAACT

CAGAATATATTGAAACAACTTCAAAAGCTTATACAGATGGAAAAATTAACATCGAT

CACTCTGGAGGATACGTTGCTCAATTCAACATTTCTTGGGATGAAGTAAATTATGAT

LLO441 Δ26 amino acid sequence (SEQ ID NO: 24)

MKKIMLVFITLILVSLPIAQQTEAKDASAFNKEEIDKYIQGLDYNKNNVLVYHGDAVTN

VPPRKGYKDGNEYIVVEKKKKSINQNNADIQVVNAISSLTYPGALVKANSELVENQPDV

LPVKRDSLTLSIDLPGMTNQDNKIVVKNATKSNVNNAVNTLVERWNEKYAQAYPNVSA

KIDYDDEMAYSESQLIAKFGTAFKAVNNSLNVNFGAISEGKMQEEVISFKQIYYNVNVN

EPTRPSRFFGKAVTKEQLQALGVNAENPPAYISSVAYGRQVYLKLSTNSHSTKVKAAFD

AAVSGKSVSGDVELTNIIKNSSFKAVIYGGSAKDEVQIIDGNLGDLRDILKKGATFNRETP

GVPIAYTTNFLKDNELAVIKNNSEYIETTSKAYTDGKINIDHSGGYVAQFNISWDEVNYD

ActAN100 nucleotide sequence (SEQ ID NO: 31)

GTGGGATTAAATAGATTTATGCGTGCGATGATGGTAGTTTTCATTACTGCCAACTGC

ATTACGATTAACCCCGACATAATATTTGCAGCGACAGATAGCGAAGATTCCAGTCTA

AACACAGATGAATGGGAAGAAGAAAAAACAGAAGAGCAGCCAAGCGAGGTAAATA

CGGGACCAAGATACGAAACTGCACGTGAAGTAAGTTCACGTGATATTGAGGAACTA

GAAAAATCGAATAAAGTGAAAAATACGAACAAAGCAGACCTAATAGCAATGTTGA

AAGCAAAAGCAGAGAAAGGT

ActAN100 amino acid sequence (SEQ ID NO: 32)

MGLNRFMRAMMVVFITANCITINPDIIFAATDSEDSSLNTDEWEEEKTEEQPSEVNTGPR

YETAREVSSRDIEELEKSNKVKNTNKADLIAMLKAKAEKG

The components of actAp-ActAN100*-EGFRvIIIx5-mesothelin$_{35-622}$-stop (SEQ ID NO:1) are: actA promoter (lowercase); ActAN100* (uppercase); BamHI cloning linker (first underlined); EGFRvIIIx5 (italics); MfeI cloning linker (second underlined); Mesothelin$_{35-622}$ (bold); stop codon (taa).

The components of the ADU-214 fusion protein amino acid sequence (SEQ ID NO:8) are: ActAN100* (normal text); GS: BamHI cloning linker (double underlined); QL: MfeI cloning linker (dotted underlined); EGFRvIIIx5 (italics); Mesothelin35-622 (bold).

In some embodiments, the present invention provides a fusion protein comprising an epidermal growth factor receptor variant III (EGFRvIII) polypeptide fused to a mesothelin polypeptide.

In some embodiments, said EGFRvIII polypeptide comprises an amino acid sequence at least i) 90% identical, ii) 95% identical, or iii) 99% identical to SEQ ID NO:9.

In some embodiments, said fusion protein comprises a plurality of EGFRvIII polypeptides. In one embodiment, said fusion protein comprises five copies of the EGFRvIII polypeptide.

In some embodiments, said EGFRvIII polypeptide is flanked by one or more cleaver sequences. In some embodiments, the EGFRvIII polypeptide is N-terminal to the mesothelin polypeptide.

In some embodiments, the mesothelin polypeptide comprises an amino acid sequence at least i) 90% identical, ii) 95% identical, or iii) 99% identical to mesothelin$_{35-622}$ as set forth in SEQ ID NO:11.

In some embodiments, the fusion protein comprises one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35-622}$ as set forth in SEQ ID NO:11.

In some embodiments, the fusion protein comprises an EGFRvIIIx5 polypeptide comprising an amino acid sequence at least i) 90% identical, ii) 95% identical, or iii) 99% identical to EGFRvIIIx5 as set forth in SEQ ID NO:10 and mesothelin polypeptide comprising an amino acid sequence at least i) 90% identical, ii) 95% identical, or iii) 99% identical to $mesothelin_{35-622}$ as set forth in SEQ ID NO:11.

In some embodiments, the fusion protein comprises an amino acid sequence that is at least i) 90% identical, ii) 95% identical, or iii) 99% identical to EGFRvIIIx5-$mesothelin_{35-622}$ as set forth as amino acid residues 89 to 840 of SEQ ID NO:8.

In some embodiments, the fusion protein further comprises a signal sequence, wherein the signal sequence is in translational reading frame with the EGFRvIII polypeptide and the mesothelin polypeptide. In some embodiments, the signal sequence is at least i) 90% identical, ii) 95% identical, or iii) 99% identical to ActAN100* as set forth in SEQ ID NO:12.

In some embodiments, the fusion protein of any of the preceding embodiments comprises an amino acid sequence that is at least i) 90% identical, ii) 95% identical, or iii) 99% identical to SEQ ID NO:8.

In some embodiments, said fusion protein is expressed in a bacterium. In one embodiment, the bacterium is *Listeria monocytogenes*.

In some embodiments, the present invention provides a nucleic acid molecule encoding the fusion protein of any of the preceding embodiments.

In some embodiments, the nucleic acid molecule comprises one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the $mesothelin_{35-622}$ polynucleotide as set forth in SEQ ID NO:6.

In some embodiments, the nucleic acid molecule comprises a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the $mesothelin_{35-622}$ polynucleotide as set forth in SEQ ID NO:6.

In some embodiments, said nucleic acid molecule is part of an expression cassette.

In some embodiments, the present invention provides a host cell comprising the nucleic acid molecule of any of the preceding embodiments. In some embodiments, the host cell is a bacterium. In one embodiment, the bacterium is *Listeria monocytogenes*. In some embodiments, the *Listeria monocytogenes* is an actA deletion mutant, an actA insertion mutant, an inlB deletion mutant, an inlB insertion mutant, or a combination thereof. In certain embodiments, the *Listeria monocytogenes* is a ΔactA/ΔinlB mutant.

In certain embodiments, the nucleic acid molecule is integrated into the host cell genome. In some embodiments, the nucleic acid molecule is integrated into the $tRNA^{Arg}$ locus.

In some embodiments, the present invention provides a vector comprising the nucleic acid molecule of any of the preceding embodiments.

In some embodiments, the present invention provides a nucleic acid molecule encoding an EGFRvIII-mesothelin fusion protein, wherein the fusion protein comprises one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to $mesothelin_{35-622}$ as set forth in SEQ ID NO:11.

In certain embodiments, the EGFR-mesothelin fusion protein comprising an EGFRvIIIx5 polypeptide comprising an amino acid sequence at least i) 90% identical, ii) 95% identical, or iii) 99% identical to EGFRvIIIx5 as set forth in SEQ ID NO:10 and mesothelin polypeptide comprising an amino acid sequence at least i) 90% identical, ii) 95% identical, or iii) 99% identical to $mesothelin_{35-622}$ as set forth in SEQ ID NO:11

In certain embodiments, the EGFR-mesothelin fusion protein comprises an amino acid sequence that is at least i) 90% identical, ii) 95% identical, or iii) 99% identical to EGFRvIIIx5-$mesothelin_{35-622}$ as set forth in amino acid residues 89 to 840 of SEQ ID NO:8.

In some embodiments, the nucleic acid further comprises a signal sequence, wherein the signal sequence is in translational frame with the nucleotide sequence encoding the EGFRvIII polypeptide and the nucleotide sequence encoding the mesothelin polypeptide. In certain embodiments, the signal sequence is at least i) 90% identical, ii) 95% identical, or iii) 99% identical to ActAN100* as set forth in SEQ ID NO:3. In some embodiments, the nucleic acid further comprises a promoter. In various embodiments, the promoter is at least i) 90% identical, ii) 95% identical, or iii) 99% identical to an actA promoter as set forth in SEQ ID NO:2. In some embodiments, the promoter is at least i) 90% identical, ii) 95% identical, or 99% identical to an My promoter as set forth in SEQ ID NO: 18

In some embodiments, the nucleic acid molecule of any of the preceding embodiments comprises a nucleotide sequence that is at least i) 90% identical, ii) 95% identical, or iii) 99% identical to SEQ ID NO:1.

In some embodiments, the present invention provides a host cell comprising the nucleic acid molecule of any of the preceding embodiments. In certain embodiments, said host cell is a bacterium. In one embodiments, said bacterium is *Listeria monocytogenes*. In various embodiments, the *Listeria monocytogenes* is an actA deletion mutant, an actA insertion mutant, an inlB deletion mutant, an inlB insertion mutant, or a combination thereof. In certain embodiments, the *Listeria monocytogenes* is a ΔactA/ΔinlB mutant. In some embodiments, the nucleic acid molecule is integrated into the host cell genome. For example, the nucleic acid molecule is integrated into the $tRNA^{Arg}$ locus.

In some embodiments, the host cell is in combination with a pharmaceutically acceptable excipient.

In some embodiments, the present invention provides a vaccine comprising the host cell of any of the preceding embodiments and a pharmaceutically acceptable excipient.

In some embodiments, the present invention provides a vector encoding the nucleic acid molecule of any of the preceding embodiments.

In some embodiments, the present invention provides a method of eliciting an immune response in a subject comprising, administering to the subject a composition comprising a host cell, wherein the host cell comprises a nucleic acid molecule encoding an EGFRvIII-mesothelin fusion protein.

In some embodiments, the nucleic acid molecule comprises one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the $mesothelin_{35-622}$ polynucleotide as set forth in SEQ ID NO:6.

In some embodiments, the nucleic acid molecule comprises a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the mesothelin$_{35-622}$ polynucleotide as set forth in SEQ ID NO:6.

In various embodiments, the nucleic acid molecule comprises a nucleotide sequence that is at least i) 90% identical, ii) 95% identical, or iii) 99% identical to SEQ ID NO:1.

In some embodiments, the nucleic acid molecule is integrated into the genome of said host cell. For example, the nucleic acid molecule is integrated into the tRNA$^{Arg}$ locus.

In some embodiments of any of the preceding methods, the host cell is *Listeria monocytogenes*. In certain embodiments, the *Listeria monocytogenes* is an actA deletion mutant, an actA insertion mutant, an inlB deletion mutant, an inlB insertion mutant, or a combination thereof. In one embodiment, the *Listeria monocytogenes* is a ΔactA/ΔinlB mutant.

In some embodiments of any of the preceding methods, the administering step is performed intravenously. In certain embodiments, the fusion protein is expressed and secreted from the host cell in the cytosol of an infected cell within the subject. In one embodiment, the infected cell is an antigen presenting cell.

In some embodiments of any of the preceding methods, the EGFRvIII-mesothelin fusion protein comprises one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35-622}$ as set forth in SEQ ID NO:11.

In some embodiments of any of the preceding methods, the EGFRvIII-mesothelin fusion protein comprises an EGFRvIIIx5 polypeptide comprising an amino acid sequence at least i) 90% identical, ii) 95% identical, or iii) 99% identical to EGFRvIIIx5 as set forth in SEQ ID NO:10 and mesothelin polypeptide comprising an amino acid sequence at least i) 90% identical, ii) 95% identical, or iii) 99% identical to mesothelin$_{35-622}$ as set forth in SEQ ID NO:11.

In some embodiments of any of the preceding methods, the EGFRvIII-mesothelin fusion protein comprises an amino acid sequence that is at least i) 90% identical, ii) 95% identical, or iii) 99% identical to EGFRvIIIx5-mesothelin$_{35-622}$ as set forth in amino acid residues 89 to 840 of SEQ ID NO:8.

In certain embodiments, the present invention provides a method of increasing expression of a mesothelin polypeptide comprising, expressing in a host cell a nucleic acid molecule comprising an EGFRvIII polynucleotide and a mesothelin polynucleotide encoding the mesothelin polypeptide.

In some embodiments, the EGFRvIII polynucleotide is at least i) 90% identical, ii) 95% identical, or iii) 99% identical to SEQ ID NO:4.

In certain embodiments, the nucleic acid molecule comprises a plurality of EGFRvIII polynucleotides, wherein each EGFRvIII polynucleotide comprises a nucleotide sequence that is at least i) 90% identical, ii) 95% identical, or iii) 99% identical to SEQ ID NO:4. In some embodiments, the nucleic acid molecule comprises five copies of the EGFRvIII polynucleotide, wherein the EGFRvIII polynucleotide is at least i) 90% identical, ii) 95% identical, or iii) 99% identical to SEQ ID NO:5.

In various embodiments, the mesothelin polypeptide comprises an amino acid sequence that is at least i) 90% identical, ii) 95% identical, or iii) 99% identical to mesothelin$_{35-622}$ as set forth in SEQ ID NO:11. In certain embodiments, the nucleic acid molecule comprises one or more EGFRvIII polynucleotides that are at least i) 90% identical, ii) 95% identical, or iii) 99% identical to the EGFRvIII polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6. In some embodiments, the nucleic acid molecule comprise a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the mesothelin$_{35-622}$ polynucleotide as set forth in SEQ ID NO:6.

In certain embodiments, the nucleic acid molecule further comprises a signal sequence, a promoter, or both, wherein the promoter, signal sequence, or both are operably linked with the nucleotide sequence encoding the EGFRvIII polypeptide and the nucleotide sequence encoding the mesothelin polypeptide.

In some embodiments, the nucleic acid molecule comprises a nucleotide sequence that is at least i) 90% identical, ii) 95% identical, or iii) 99% identical to SEQ ID NO: 1. In some embodiments of any of the preceding methods, the host cell is *Listeria monocytogenes.*

In some embodiments of any of the preceding methods, said expressing step comprises infecting a cell of interest with the host cell. In some embodiments, said expressing step comprises administering the host cell to a subject.

In some embodiments, the present invention provides a method of treating cancer in a subject in need thereof, said methods comprising administering to the subject a therapeutically effective amount of a composition comprising a host cell, wherein the host cell comprises a nucleic acid molecule encoding an EGFRvIII-mesothelin fusion protein. In some embodiments, the cancer is a mesothelin-expressing cancer, an EGFRvIII-expressing cancer, or both. In some embodiments, the cancer has a high level of mesothelin expression. In certain embodiments, the cancer is lung cancer. In various embodiments, the lung cancer is non-small cell lung cancer (NSCLC) adenocarcinoma, NSCLC squamous cell carcinoma, large cell carcinoma, or any combination thereof. In some embodiments, the lung cancer is advanced NSCLC adenocarcinoma or metastatic NSCLC adenocarcinoma. In one embodiment, the subject has failed standard therapy. In some embodiments, the subject had surgery, radiation, chemotherapy, or any combination thereof.

In some embodiments, the EGFRvIII-mesothelin fusion protein comprises an EGFRvIII polypeptide having an amino acid sequence at least i) 90% identical, ii) 95% identical, or iii) 99% identical to SEQ ID NO:9, In certain embodiments, the fusion protein comprises a plurality of EGFRvIII polypeptides. In one embodiment, the fusion protein comprises five copies of the EGFRvIII polypeptide.

In certain embodiments, the EGFRvIII-mesothelin fusion protein comprises a mesothelin polypeptide having an amino acid sequence at least i) 90% identical, ii) 95% identical, or iii) 99% identical to mesothelin$_{35-622}$ as set forth in SEQ II) NO:11.

In some embodiments, the EGFRvIII-mesothelin fusion protein comprises one or more EGFRvIII polypeptides each of which comprising an amino acid sequence at least i) 90% identical, ii) 95% identical, or iii) 99% identical to EGFRvIII as set forth in SEQ ID NO:9 and mesothelin polypeptide comprising an amino acid sequence at least i) 90% identical, ii) 95% identical, or iii) 99% identical to mesothelin$_{35-622}$ as set forth in SEQ ID NO:11.

In some embodiments, the EGFRvIII-mesothelin fusion protein comprises an amino acid sequence at least i) 90% identical, ii) 95% identical, or iii) 99% identical to EGFRvIIIx5 as set forth in SEQ ID NO:10 and mesothelin polypeptide comprising an amino acid sequence at least i) 90% identical, ii) 95% identical, or iii) 99% identical to mesothelin$_{35-622}$ as set forth in SEQ NO:11.

In some embodiments, the fusion protein comprises an amino acid sequence that is at least i) 90% identical, ii) 95% identical, or iii) 99% identical to EGFRvIIIx5-mesothelin$_{35-622}$ as set forth as amino acid residues 89 to 840 of SEQ ID NO:8.

In some embodiments, the EGFRvIII-mesothelin fusion protein comprises an amino acid sequence that is at least i) 90% identical, ii) 95% identical, or iii) 99% identical to EGFRvIIIx5-mesothelin$_{35-622}$ as set forth in SEQ ID NO:8.

In certain embodiments, the nucleic acid molecule comprises one or more EGFRvIII polynucleotides that are at least i) 90% identical, ii) 95% identical, or iii) 99% identical to the EGFR viii polynucleotide as set forth in SEQ ID NO:4 and a mesothelin polynucleotide that is at least i) 90% identical, ii) 95% identical, or iii) 99% identical to the mesothelin$_{35-622}$ polynucleotide as set forth in SEQ ID NO:6.

In some embodiments, the nucleic acid molecule comprises a polynucleotide that is at least i) 90% identical, ii) 95% identical, or iii) 99% identical to the EGFRvIIIx5 polynucleotide as set forth in SEQ ID NO:5 and a polynucleotide that is at least i) 90% identical, ii) 95% identical, or iii) 99% identical to the mesothelin$_{35-622}$ polynucleotide as set forth in SEQ ID NO:6.

In some embodiments, the nucleic acid molecule comprises a nucleotide sequence that is at least i) 90% identical, ii) 95% identical, or iii) 99% identical to actAp-ActAN100*-EGFRvIII-mesothelin$_{35-622}$ as set forth in SEQ ID NO: 1.

In some embodiments, the nucleic acid molecule comprises a nucleotide sequence that it at least i) 90% identical, ii) 95% identical, or iii) 99% identical to EGFRvIIIx5-mesothelin$_{35-622}$ as set forth in SEQ ID NO:7.

In certain embodiments, said nucleic acid molecule is integrated into the host cell genome. In one embodiment, the nucleic acid molecule is integrated into the $tRNA^{Arg}$ locus. In certain embodiments, the host cell is *Listeria monocytogenes*. In certain embodiments, the *Listeria monocytogenes* is an actA deletion (ΔactA) mutant, an actA insertion mutant, an inlB deletion (ΔinlB) mutant, an inlB insertion mutant, or a combination thereof. In some embodiments, the *Listeria monocytogenes* is a ΔactA/ΔinlB mutant.

In various embodiments, the fusion protein is expressed and secreted from the host cell in the cytosol of an infected cell within the subject. In some embodiments, the infected cell is an antigen presenting cell. In some embodiments, the method further comprises measuring mesothelin levels, detecting EGFRvIII, or both in a biological sample from the subject prior to administering the composition.

In some embodiments of any of the preceding methods, the composition further comprises a pharmaceutically acceptable excipient. In certain embodiments, the pharmaceutically acceptable excipient comprises phosphate-buffered saline (PBS) and glycerol. In certain embodiments, the administering step is performed intravenously. In some embodiments, the method further comprises administering an antibiotic to the subject after administering the composition. In some embodiments, the antibiotic is administered after a last dose of the composition. In certain embodiments, the antibiotic is amoxicillin or trimethoprim/sulfamethoxazole.

In certain embodiments, the nucleic acid molecule of the host cell of any of the preceding embodiments is inserted into an expression cassette on an episomal plasmid within the host cell.

In some embodiments, the fusion protein of any of the preceding embodiments and which further comprise a signal sequence, wherein the signal sequence is in translational reading frame with the EGFRvIII polypeptide and the mesothelin polypeptide: the signal sequence is at least i) 90% identical, ii) 95% identical, or iii) 99% identical to an LLO441 signal sequence as set forth in SEQ ID NO:20, at least i) 90% identical, ii) 95% identical, or iii) 99% identical to an LLO441ΔPEST signal sequence as set forth in SEQ ID NO:22, or at least i) 90% identical, ii) 95% identical, or iii) 99% identical to an LLO441Δ26 signal sequence as set forth in SEQ ID NO:24.

In some embodiments, the nucleic acid of any of the preceding embodiments, and which further comprise a signal sequence, wherein the signal sequence is in translational frame with the nucleotide sequence encoding the EGFRvIII polypeptide and the nucleotide sequence encoding the mesothelin polypeptide: the signal sequence is at least i) 90% identical, ii) 95% identical, or iii) 99% identical to an LLO441 signal sequence as set forth in SEQ NO:20, at least i) 90% identical, ii) 95% identical, or iii) 99% identical to an LLO441ΔPEST signal sequence as set forth in SEQ NO:22, or at least i) 90% identical, ii) 95% identical, or iii) 99% identical to an LLO441Δ26 signal sequence as set forth in SEQ ID NO:24.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A fusion protein comprising an epidermal growth factor receptor variant III (EGFRvIII) polypeptide fused to a mesothelin polypeptide, wherein said fusion protein polypeptide comprises the amino acid sequence of SEQ ID NO: 8.

2. The fusion protein of claim 1, wherein said fusion protein is expressed by a bacterium.

3. The fusion protein of claim 2, wherein the bacterium is *Listeria monocytogenes*.

4. A nucleic acid molecule encoding the fusion protein of claim 1.

5. The nucleic acid molecule of claim 4, said nucleic acid molecule being part of an expression cassette.

6. A host cell comprising the nucleic acid molecule of claim 5.

7. The host cell of claim 6, wherein the host cell is a bacterium.

8. A vector comprising the nucleic acid molecule of claim 5.

9. A vaccine comprising the host cell of claim 6 and a pharmaceutically acceptable excipient.

10. A method of eliciting an immune response in a subject, said method comprising administering to the subject a composition comprising a host cell, wherein the host cell comprises a nucleic acid molecule encoding a polypeptide of SEQ ID NO: 8.

11. The method of claim 10, wherein the host cell is a *Listeria monocytogenes*.

12. A method of expression of a mesothelin polypeptide, in a *Listeria monocytogenes* host cell, said method comprising expressing in the *Listeria monocytogenes* host cell a nucleic acid molecule encoding a polypeptide comprising the sequence of SEQ ID NO: 8.

13. A method of treating cancer in a subject that has cancer, said method comprising administering to the subject a therapeutically effective amount of a composition comprising a *Listeria monocytogenes* host cell, wherein the *Listeria monocytogenes* host cell comprises a nucleic acid molecule encoding a polypeptide comprising SEQ ID NO: 8, and wherein the cancer is a mesothelin-expressing cancer, an EGFRvIII-expressing cancer, or both.

14. The method of claim 13, wherein the cancer is a mesothelin-expressing cancer.

15. The method of claim 13, wherein the cancer has a high level of mesothelin expression.

16. The method of claim 13, wherein the cancer is lung cancer.

17. The method of claim 16, wherein the lung cancer is non-small cell lung cancer (NSCLC) adenocarcinoma, NSCLC squamous cell carcinoma, large cell carcinoma, or any combination thereof.

18. The method of claim 16, wherein the lung cancer is advanced NSCLC adenocarcinoma or metastatic NSCLC adenocarcinoma.

19. The host cell of claim 7, wherein the bacterium is a *Listeria monocytogenes*.

20. A method of treating cancer in a subject that has cancer characterized as expressing human mesothelin in a subject, said method comprising administering to the subject a therapeutically effective amount of a composition comprising live-attenuated *Listeria monocytogenes* host cells expressing a nucleic acid molecule encoding a fusion protein comprising the amino acid sequence of SEQ ID NO: 8 to elicit in the subject immune responses directed against cancer cells expressing human mesothelin in the subject, thereby treating the cancer in the subject.

* * * * *